(12) United States Patent
Mercanzini et al.

(10) Patent No.: US 10,065,031 B2
(45) Date of Patent: *Sep. 4, 2018

(54) DEEP BRAIN STIMULATION LEAD

(71) Applicant: ALEVA NEUROTHERAPEUTICS, Lausanne (CH)

(72) Inventors: Andre Mercanzini, Saint Sulpice (CH); Alain Jordan, Denges (CH); Alexandre Michalis, Le Grand-Saconnex (CH); Marc Boers, Cully (CH); Alain Dransart, Rolle (CH)

(73) Assignee: ALEVA NEUROTHERAPEUTICS, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/281,468

(22) Filed: Sep. 30, 2016

(65) Prior Publication Data

US 2017/0028191 A1 Feb. 2, 2017

Related U.S. Application Data

(63) Continuation of application No. 14/470,423, filed on Aug. 27, 2014, now Pat. No. 9,474,894.

(51) Int. Cl.
| | |
|---|---|
| *A61B 6/12* | (2006.01) |
| *A61B 1/05* | (2006.01) |
| *A61B 5/04* | (2006.01) |
| *A61N 1/05* | (2006.01) |
| *A61B 5/00* | (2006.01) |
| *H05K 1/11* | (2006.01) |

(52) U.S. Cl.
CPC ........ *A61N 1/0534* (2013.01); *A61B 5/04001* (2013.01); *A61N 1/0551* (2013.01); *A61B 5/04* (2013.01); *A61B 5/6868* (2013.01); *A61B 6/12* (2013.01); *H05K 1/118* (2013.01)

(58) Field of Classification Search
CPC ..................................................... A61N 1/0534
USPC ....................... 600/300, 377–378; 607/2, 45
See application file for complete search history.

(56) References Cited

U.S. PATENT DOCUMENTS

| | | | |
|---|---|---|---|
| 4,245,645 | A | 1/1981 | Arseneault et al. |
| 4,550,733 | A | 11/1985 | Liss et al. |

(Continued)

FOREIGN PATENT DOCUMENTS

| | | |
|---|---|---|
| EP | 0 677 743 A2 | 10/1995 |
| EP | 0 743 839 | 11/1996 |

(Continued)

OTHER PUBLICATIONS

US 8,388,533, 03/2013, Hafezi et al. (withdrawn)

(Continued)

*Primary Examiner* — Carl H Layno
*Assistant Examiner* — Jon Eric C Morales
(74) *Attorney, Agent, or Firm* — Foley & Lardner LLP; James De Vellis

(57) ABSTRACT

The present disclosure discusses a system and methods for a deep brain stimulation lead. More particularly, the disclosure discusses a stimulation lead that includes one or more silicon based barrier layers within a MEMS film. The silicon based barrier layers can improve device reliability and durability. The silicon based barrier layers can also improve adhesion between the layers of the MEMS film.

19 Claims, 51 Drawing Sheets

(56) References Cited

U.S. PATENT DOCUMENTS

| | | | |
|---|---|---|---|
| 4,837,049 | A | 6/1989 | Byers et al. |
| 4,917,093 | A | 4/1990 | Dufresne et al. |
| 4,928,297 | A | 5/1990 | Tsutsui et al. |
| 4,969,468 | A | 11/1990 | Byers et al. |
| 4,989,617 | A | 2/1991 | Memberg et al. |
| 5,095,905 | A | 3/1992 | Klepinski |
| 5,215,088 | A | 6/1993 | Normann et al. |
| 5,391,250 | A | 2/1995 | Cheney et al. |
| 5,400,784 | A | 3/1995 | Durand et al. |
| 5,419,777 | A | 5/1995 | Hofling |
| 5,458,629 | A | 10/1995 | Baudino et al. |
| 5,496,369 | A | 3/1996 | Howard, III |
| 5,524,338 | A | 6/1996 | Martyniuk et al. |
| 5,628,317 | A | 5/1997 | Starkebaum et al. |
| 5,643,330 | A | 7/1997 | Holsheimer et al. |
| 5,679,355 | A | 10/1997 | Alexander et al. |
| 5,683,422 | A | 11/1997 | Rise |
| 5,697,651 | A | 12/1997 | Fernandes |
| 5,697,975 | A | 12/1997 | Howard et al. |
| 5,702,429 | A | 12/1997 | King |
| 5,713,922 | A | 2/1998 | King |
| 5,713,923 | A | 2/1998 | Ward et al. |
| 5,716,377 | A | 2/1998 | Rise et al. |
| 5,727,552 | A | 3/1998 | Ryan |
| 5,752,979 | A | 5/1998 | Benabid |
| 5,755,759 | A | 5/1998 | Cogan |
| 5,782,798 | A | 7/1998 | Rise |
| 5,792,186 | A | 8/1998 | Rise |
| 5,797,970 | A | 8/1998 | Pouvreau |
| 5,800,474 | A | 9/1998 | Benabid et al. |
| 5,800,535 | A | 9/1998 | Howard, III |
| 5,814,092 | A | 9/1998 | King |
| 5,824,029 | A | 10/1998 | Weijand et al. |
| 5,833,709 | A | 11/1998 | Rise et al. |
| 5,833,714 | A | 11/1998 | Loeb |
| 5,843,148 | A | 12/1998 | Gijsbers et al. |
| 5,893,883 | A | 4/1999 | Torgerson et al. |
| 5,913,882 | A | 6/1999 | King |
| 5,921,924 | A | 7/1999 | Avitall |
| 5,927,277 | A | 7/1999 | Baudino et al. |
| 5,941,906 | A | 8/1999 | Barreras et al. |
| 5,957,958 | A | 9/1999 | Schulman et al. |
| 5,975,085 | A | 11/1999 | Rise |
| 5,978,702 | A | 11/1999 | Ward et al. |
| 5,991,668 | A | 11/1999 | Leinders et al. |
| 6,011,996 | A | 1/2000 | Gielen et al. |
| 6,018,682 | A | 1/2000 | Rise |
| 6,024,095 | A | 2/2000 | Stanley, III |
| 6,033,403 | A | 3/2000 | Tu et al. |
| 6,038,480 | A | 3/2000 | Hrdlicka et al. |
| 6,050,992 | A | 4/2000 | Nichols |
| 6,094,598 | A | 7/2000 | Elsberry et al. |
| 6,104,960 | A | 8/2000 | Duysens et al. |
| 6,109,269 | A | 8/2000 | Rise et al. |
| 6,125,300 | A | 9/2000 | Weijand et al. |
| 6,128,537 | A | 10/2000 | Rise |
| 6,129,685 | A | 10/2000 | Howard, III |
| 6,161,047 | A | 12/2000 | King et al. |
| 6,205,359 | B1 | 3/2001 | Boveja |
| 6,205,361 | B1 | 3/2001 | Kuzma et al. |
| 6,216,043 | B1 | 4/2001 | Swanson et al. |
| 6,227,203 | B1 | 5/2001 | Rise et al. |
| 6,253,109 | B1 | 6/2001 | Gielen |
| 6,253,110 | B1 | 6/2001 | Brabec et al. |
| 6,263,237 | B1 | 7/2001 | Rise |
| 6,266,564 | B1 | 7/2001 | Hill et al. |
| 6,295,476 | B1 | 9/2001 | Schaenzer |
| 6,301,492 | B1 | 10/2001 | Zonenshayn |
| 6,319,241 | B1 | 11/2001 | King et al. |
| 6,330,466 | B1 | 12/2001 | Hofmann et al. |
| 6,337,997 | B1 | 1/2002 | Rise |
| 6,343,226 | B1 | 1/2002 | Sunde et al. |
| 6,353,762 | B1 | 3/2002 | Baudino et al. |
| 6,356,784 | B1 | 3/2002 | Lozano et al. |
| 6,356,786 | B1 | 3/2002 | Rezai et al. |
| 6,356,787 | B1 | 3/2002 | Rezai et al. |
| 6,364,875 | B1 | 4/2002 | Stanley, III |
| 6,366,813 | B1 | 4/2002 | DiLorenzo |
| 6,374,140 | B1 | 4/2002 | Rise |
| 6,375,666 | B1 | 4/2002 | Mische |
| 6,379,353 | B1 | 4/2002 | Nichols |
| 6,415,187 | B1 | 7/2002 | Kuzma et al. |
| 6,434,431 | B1 | 8/2002 | Camps et al. |
| 6,479,999 | B1 | 11/2002 | Demeester et al. |
| 6,484,059 | B2 | 11/2002 | Gielen |
| 6,493,590 | B1 | 12/2002 | Wessman et al. |
| 6,510,347 | B2 | 1/2003 | Borkan |
| 6,529,774 | B1 | 3/2003 | Greene |
| 6,538,443 | B2 | 3/2003 | Morich et al. |
| 6,549,812 | B1 | 4/2003 | Smits |
| 6,556,873 | B1 | 4/2003 | Smits |
| 6,560,472 | B2 | 5/2003 | Hill et al. |
| 6,560,486 | B1 | 5/2003 | Osorio et al. |
| 6,581,046 | B1 | 6/2003 | Ahissar |
| 6,587,733 | B1 | 7/2003 | Cross et al. |
| 6,591,128 | B1 | 7/2003 | Wu et al. |
| 6,594,524 | B2 | 7/2003 | Esteller et al. |
| 6,597,953 | B2 | 7/2003 | Boling |
| 6,643,552 | B2 | 11/2003 | Edell et al. |
| 6,671,544 | B2 | 12/2003 | Baudino |
| 6,675,046 | B2 | 1/2004 | Holsheimer |
| 6,687,538 | B1 | 2/2004 | Hrdlicka et al. |
| 6,690,973 | B2 | 2/2004 | Hill et al. |
| 6,708,064 | B2 | 3/2004 | Rezai |
| 6,718,208 | B2 | 4/2004 | Hill et al. |
| 6,718,211 | B2 | 4/2004 | Smits |
| 6,741,893 | B2 | 5/2004 | Smits |
| 6,745,079 | B2 | 6/2004 | King |
| 6,757,970 | B1 | 7/2004 | Kuzma et al. |
| 6,795,737 | B2 | 9/2004 | Gielen et al. |
| 6,804,552 | B2 | 10/2004 | Thompson et al. |
| 6,818,396 | B1 | 11/2004 | Bloch et al. |
| 6,829,498 | B2 | 12/2004 | Kipke et al. |
| 6,850,802 | B2 | 2/2005 | Holsheimer |
| 6,871,098 | B2 | 3/2005 | Nuttin et al. |
| 6,882,881 | B1 | 4/2005 | Lesser et al. |
| 6,892,097 | B2 | 5/2005 | Holsheimer |
| 6,892,438 | B1 | 5/2005 | Hill et al. |
| 6,904,306 | B1 | 6/2005 | Wu et al. |
| 6,909,920 | B2 | 6/2005 | Lokhoff et al. |
| 6,920,359 | B2 | 7/2005 | Meadows et al. |
| 6,928,320 | B2 | 8/2005 | King |
| 6,950,706 | B2 | 9/2005 | Rodriguez et al. |
| 6,950,709 | B2 | 9/2005 | Baudino |
| 6,978,171 | B2 | 12/2005 | Goetz et al. |
| 6,978,178 | B2 | 12/2005 | Sommer et al. |
| 6,999,819 | B2 | 2/2006 | Swoyer et al. |
| 7,006,859 | B1 | 2/2006 | Osorio et al. |
| 7,010,351 | B2 | 3/2006 | Firlik et al. |
| 7,010,356 | B2 | 3/2006 | Jog et al. |
| 7,024,246 | B2 | 4/2006 | Acosta et al. |
| 7,035,690 | B2 | 4/2006 | Goetz |
| 7,047,082 | B1 | 5/2006 | Schrom et al. |
| 7,047,084 | B2 | 5/2006 | Erickson et al. |
| 7,050,856 | B2 | 5/2006 | Stypulkowski |
| 7,051,419 | B2 | 5/2006 | Schrom et al. |
| 7,061,240 | B2 | 6/2006 | Ham et al. |
| 7,063,767 | B1 | 6/2006 | Tyson et al. |
| 7,076,292 | B2 | 7/2006 | Forsberg |
| 7,077,822 | B1 | 7/2006 | Howard, III |
| 7,107,104 | B2 | 9/2006 | Keravel et al. |
| 7,133,718 | B2 | 11/2006 | Bakken et al. |
| 7,146,222 | B2 | 12/2006 | Boling |
| 7,151,961 | B1 | 12/2006 | Whitehurst et al. |
| 7,174,219 | B2 | 2/2007 | Wahlstrand et al. |
| 7,177,701 | B1 | 2/2007 | Pianca |
| 7,181,288 | B1 | 2/2007 | Rezai et al. |
| 7,184,829 | B2 | 2/2007 | Hill et al. |
| 7,187,978 | B2 | 3/2007 | Malek et al. |
| 7,191,016 | B2 | 3/2007 | Marshall et al. |
| 7,191,018 | B2 | 3/2007 | Gielen et al. |
| 7,200,439 | B2 | 4/2007 | Zdeblick et al. |
| 7,203,548 | B2 | 4/2007 | Whitehurst et al. |
| 7,204,798 | B2 | 4/2007 | Zdeblick et al. |

(56) References Cited

U.S. PATENT DOCUMENTS

| | | |
|---|---|---|
| 7,204,833 B1 | 4/2007 | Osorio et al. |
| 7,209,787 B2 | 4/2007 | Dilorenzo |
| 7,212,851 B2 | 5/2007 | Donoghue et al. |
| 7,212,867 B2 | 5/2007 | Van Venroo et al. |
| 7,214,189 B2 | 5/2007 | Zdeblick |
| 7,216,000 B2 | 5/2007 | Sieracki et al. |
| 7,216,001 B2 | 5/2007 | Hacker et al. |
| 7,231,256 B2 | 6/2007 | Wahlstrand et al. |
| 7,236,822 B2 | 6/2007 | Dobak, III |
| 7,242,984 B2 | 7/2007 | Dilorenzo |
| 7,276,061 B2 | 10/2007 | Schaer et al. |
| 7,280,867 B2 | 10/2007 | Frei et al. |
| 7,282,030 B2 | 10/2007 | Frei et al. |
| 7,282,050 B2 | 10/2007 | Starkebaum et al. |
| 7,286,878 B2 | 10/2007 | Stypulkowski |
| 7,286,882 B2 | 10/2007 | Cole |
| 7,288,066 B2 | 10/2007 | Drew |
| 7,289,851 B2 | 10/2007 | Gunderson et al. |
| 7,289,852 B2 | 10/2007 | Helfinstine et al. |
| 7,295,880 B2 | 11/2007 | Gielen |
| 7,298,143 B2 | 11/2007 | Jaermann et al. |
| 7,307,223 B2 | 12/2007 | Tyson et al. |
| 7,313,430 B2 | 12/2007 | Urquhart et al. |
| 7,313,440 B2 | 12/2007 | Miesel |
| 7,315,759 B2 | 1/2008 | Markowitz et al. |
| 7,317,947 B2 | 1/2008 | Wahlstrand et al. |
| 7,317,948 B1 | 1/2008 | King et al. |
| 7,319,899 B2 | 1/2008 | Keizer |
| 7,319,904 B2 | 1/2008 | Cross et al. |
| 7,321,798 B2 | 1/2008 | Muhlenberg et al. |
| 7,321,837 B2 | 1/2008 | Osorio et al. |
| 7,322,832 B2 | 1/2008 | Kronich et al. |
| 7,328,057 B2 | 2/2008 | Freas et al. |
| 7,328,068 B2 | 2/2008 | Spinelli et al. |
| 7,328,069 B2 | 2/2008 | Gerber |
| 7,330,760 B2 | 2/2008 | Heruth et al. |
| 7,337,010 B2 | 2/2008 | Howard et al. |
| 7,343,206 B2 | 3/2008 | Sage et al. |
| 7,346,395 B2 | 3/2008 | Lozano et al. |
| 7,356,369 B2 | 4/2008 | Phillips et al. |
| 7,359,837 B2 | 4/2008 | Drew |
| 7,366,572 B2 | 4/2008 | Heruth et al. |
| 7,367,956 B2 | 5/2008 | King |
| 7,369,891 B2 | 5/2008 | Augustijn et al. |
| 7,369,893 B2 | 5/2008 | Gunderson |
| 7,369,894 B2 | 5/2008 | Gerber |
| 7,385,443 B1 | 6/2008 | Denison |
| 7,388,378 B2 | 6/2008 | Gray et al. |
| 7,389,147 B2 | 6/2008 | Wahlstrand et al. |
| 7,390,311 B2 | 6/2008 | Hildebrand et al. |
| 7,391,257 B1 | 6/2008 | Denison et al. |
| 7,392,089 B2 | 6/2008 | Wahlstrand et al. |
| 7,395,113 B2 | 7/2008 | Heruth et al. |
| 7,400,927 B1 | 7/2008 | Litvin |
| 7,403,820 B2 | 7/2008 | DiLorenzo |
| 7,406,351 B2 | 7/2008 | Wesselink |
| 7,418,292 B2 | 8/2008 | Shafer |
| 7,421,297 B2 | 9/2008 | Giftakis et al. |
| 7,427,280 B2 | 9/2008 | Gerber |
| 7,429,938 B1 | 9/2008 | Corndorf |
| 7,433,734 B2 | 10/2008 | King |
| 7,442,183 B2 | 10/2008 | Baudino et al. |
| 7,447,545 B2 | 11/2008 | Heruth et al. |
| 7,450,996 B2 | 11/2008 | MacDonald et al. |
| 7,463,917 B2 | 12/2008 | Martinez |
| 7,463,928 B2 | 12/2008 | Lee et al. |
| 7,474,247 B1 | 1/2009 | Heinks et al. |
| 7,479,910 B1 | 1/2009 | Heinks et al. |
| 7,483,748 B2 | 1/2009 | Torgerson et al. |
| 7,489,966 B2 | 2/2009 | Leinders et al. |
| 7,489,970 B2 | 2/2009 | Lee et al. |
| 7,491,181 B2 | 2/2009 | Heruth et al. |
| 7,497,844 B2 | 3/2009 | Spear et al. |
| 7,497,863 B2 | 3/2009 | Solar et al. |
| 7,502,217 B2 | 3/2009 | Zhao et al. |
| 7,505,815 B2 | 3/2009 | Lee et al. |
| 7,505,869 B2 | 3/2009 | Hartlaub |
| 7,515,961 B2 | 4/2009 | Germanson et al. |
| 7,519,431 B2 | 4/2009 | Goetz et al. |
| 7,519,432 B2 | 4/2009 | Bolea et al. |
| 7,520,890 B2 | 4/2009 | Phillips |
| 7,526,339 B2 | 4/2009 | Lahti et al. |
| 7,526,340 B2 | 4/2009 | Drew |
| 7,526,341 B2 | 4/2009 | Goetz et al. |
| 7,529,582 B1 | 5/2009 | Dilorenzo |
| 7,529,586 B2 | 5/2009 | Wahlstrand et al. |
| 7,542,803 B2 | 6/2009 | Heruth et al. |
| 7,546,164 B2 | 6/2009 | King |
| 7,546,166 B2 | 6/2009 | Michels et al. |
| 7,548,775 B2 | 6/2009 | Kipke et al. |
| 7,548,786 B2 | 6/2009 | Lee et al. |
| 7,551,951 B1 | 6/2009 | Osorio et al. |
| 7,551,960 B2 | 6/2009 | Forsberg et al. |
| 7,555,345 B2 | 6/2009 | Wahlstrand et al. |
| 7,561,921 B2 | 7/2009 | Phillips et al. |
| 7,563,141 B2 | 7/2009 | Alexander et al. |
| 7,563,541 B2 | 7/2009 | Howard et al. |
| 7,578,819 B2 | 8/2009 | Bleich et al. |
| 7,580,756 B2 | 8/2009 | Schulte et al. |
| 7,582,387 B2 | 9/2009 | Howard et al. |
| 7,590,451 B2 | 9/2009 | Tronnes et al. |
| 7,590,453 B2 | 9/2009 | Heruth et al. |
| 7,590,455 B2 | 9/2009 | Heruth et al. |
| 7,591,970 B2 | 9/2009 | Olson |
| 7,594,828 B2 | 9/2009 | Alexander et al. |
| 7,594,889 B2 | 9/2009 | St. Ores et al. |
| 7,596,399 B2 | 9/2009 | Singhal et al. |
| 7,596,408 B2 | 9/2009 | Singhal et al. |
| 7,596,415 B2 | 9/2009 | Brabec et al. |
| 7,599,730 B2 | 10/2009 | Hunter et al. |
| 7,603,161 B2 | 10/2009 | Wurmfeld et al. |
| 7,603,177 B2 | 10/2009 | Sieracki et al. |
| 7,604,629 B2 | 10/2009 | Gerber et al. |
| 7,604,644 B2 | 10/2009 | Schulte et al. |
| 7,608,458 B2 | 10/2009 | Soykan et al. |
| 7,610,083 B2 | 10/2009 | Drew et al. |
| 7,611,483 B2 | 11/2009 | Gerber et al. |
| 7,614,743 B2 | 11/2009 | Geiger |
| 7,615,015 B2 | 11/2009 | Coleman |
| 7,616,998 B2 | 11/2009 | Nuttin et al. |
| 7,617,002 B2 | 11/2009 | Goetz |
| 7,620,454 B2 | 11/2009 | Dinsmoor et al. |
| 7,622,303 B2 | 11/2009 | Soykan et al. |
| 7,622,988 B2 | 11/2009 | Denison et al. |
| 7,623,053 B2 | 11/2009 | Terry et al. |
| 7,623,918 B2 | 11/2009 | Goetz |
| 7,623,919 B2 | 11/2009 | Goetz et al. |
| 7,623,923 B2 | 11/2009 | Gerber et al. |
| 7,623,930 B2 | 11/2009 | Zeijlemaker et al. |
| 7,624,293 B2 | 11/2009 | Osorio et al. |
| 7,628,780 B2 | 12/2009 | Bonner et al. |
| 7,631,415 B2 | 12/2009 | Phillips et al. |
| 7,632,225 B2 | 12/2009 | Stypulkowski |
| 7,635,541 B2 | 12/2009 | Scott et al. |
| 7,637,867 B2 | 12/2009 | Zdeblick |
| 7,640,059 B2 | 12/2009 | Forsberg et al. |
| 7,640,060 B2 | 12/2009 | Zdeblick |
| 7,641,992 B2 | 1/2010 | Howard et al. |
| 7,642,013 B2 | 1/2010 | Howard et al. |
| 7,647,111 B2 | 1/2010 | Ries et al. |
| 7,647,116 B2 | 1/2010 | Bauhahn |
| 7,647,117 B2 | 1/2010 | Bauhahn |
| 7,647,121 B2 | 1/2010 | Wahlstrand et al. |
| 7,650,291 B2 | 1/2010 | Rosenfeld et al. |
| 7,653,433 B2 | 1/2010 | Lozano et al. |
| 7,657,318 B2 | 2/2010 | King et al. |
| 7,657,319 B2 | 2/2010 | Goetz et al. |
| 7,660,620 B2 | 2/2010 | Zeijlemaker et al. |
| 7,660,630 B2 | 2/2010 | Dudding et al. |
| 7,662,140 B2 | 2/2010 | Heruth et al. |
| 7,662,509 B2 | 2/2010 | Howard et al. |
| 7,663,066 B2 | 2/2010 | Tyson et al. |
| 7,664,551 B2 | 2/2010 | Cigaina |
| 7,664,552 B2 | 2/2010 | Wahlstrand et al. |

(56) References Cited

U.S. PATENT DOCUMENTS

| | | |
|---|---|---|
| 7,668,601 B2 | 2/2010 | Hegland et al. |
| 7,671,594 B2 | 3/2010 | Gray |
| 7,676,271 B2 | 3/2010 | Wahlstrand et al. |
| 7,676,273 B2 | 3/2010 | Goetz et al. |
| 7,676,274 B2 | 3/2010 | Hung et al. |
| 7,680,540 B2 | 3/2010 | Jensen et al. |
| 7,682,355 B2 | 3/2010 | Gerber et al. |
| 7,682,745 B2 | 3/2010 | Howard et al. |
| 7,684,860 B2 | 3/2010 | Wahlstrand et al. |
| 7,684,866 B2 | 3/2010 | Fowler et al. |
| 7,684,873 B2 | 3/2010 | Gerber |
| 7,689,289 B2 | 3/2010 | King |
| 7,697,972 B2 | 4/2010 | Verard et al. |
| 7,697,995 B2 | 4/2010 | Cross et al. |
| 7,706,124 B2 | 4/2010 | Zhao et al. |
| 7,706,889 B2 | 4/2010 | Gerber et al. |
| 7,711,421 B2 | 5/2010 | Shafer et al. |
| 7,711,428 B2 | 5/2010 | Janzig et al. |
| 7,711,436 B2 | 5/2010 | Stone |
| 7,713,194 B2 | 5/2010 | Zdeblick |
| 7,713,195 B2 | 5/2010 | Zdeblick |
| 7,720,548 B2 | 5/2010 | King |
| 7,729,768 B2 | 6/2010 | White et al. |
| 7,729,780 B2 | 6/2010 | Vardiman |
| 7,738,958 B2 | 6/2010 | Zdeblick et al. |
| 7,742,823 B2 | 6/2010 | King et al. |
| 7,756,588 B2 | 7/2010 | Jog et al. |
| 7,765,012 B2 | 7/2010 | Gerber |
| 7,769,472 B2 | 8/2010 | Gerber |
| 7,797,029 B2 | 9/2010 | Gibson et al. |
| 7,822,482 B2 | 10/2010 | Gerber |
| 7,822,483 B2 | 10/2010 | Stone et al. |
| 7,853,303 B2 | 12/2010 | Nikumb et al. |
| 7,877,149 B2 | 1/2011 | Zdeblick |
| 7,899,539 B2 | 3/2011 | Whitehurst et al. |
| 7,925,329 B2 | 4/2011 | Zdeblick et al. |
| 7,930,035 B2 | 4/2011 | Dilorenzo |
| 7,935,056 B2 | 5/2011 | Zdeblick |
| 7,941,202 B2 | 5/2011 | Hetke et al. |
| 7,945,329 B2 | 5/2011 | Bedenbaugh |
| 7,945,336 B2 | 5/2011 | Sauter-Starace et al. |
| 7,969,161 B2 | 6/2011 | Behzadi et al. |
| 7,974,705 B2 | 7/2011 | Zdeblick et al. |
| 7,978,064 B2 | 7/2011 | Zdeblick et al. |
| 7,979,105 B2 | 7/2011 | Kipke et al. |
| 7,983,751 B2 | 7/2011 | Zdeblick et al. |
| 7,991,481 B2 | 8/2011 | Benabid et al. |
| 8,000,794 B2 | 8/2011 | Lozano |
| 8,000,808 B2 | 8/2011 | Hegland et al. |
| 8,010,202 B2 | 8/2011 | Shah et al. |
| 8,024,022 B2 | 9/2011 | Schulman et al. |
| 8,032,224 B2 | 10/2011 | Miesel et al. |
| 8,036,737 B2 | 10/2011 | Goetz et al. |
| 8,036,743 B2 | 10/2011 | Savage et al. |
| 8,036,748 B2 | 10/2011 | Zdeblick et al. |
| 8,055,334 B2 | 11/2011 | Savage et al. |
| 8,055,353 B2 | 11/2011 | Kreidler et al. |
| 8,090,450 B2 | 1/2012 | Swoyer et al. |
| 8,099,170 B2 | 1/2012 | Jensen et al. |
| 8,108,049 B2 | 1/2012 | King |
| 8,114,021 B2 | 2/2012 | Robertson et al. |
| 8,115,618 B2 | 2/2012 | Robertson et al. |
| 8,121,687 B2 | 2/2012 | Jensen et al. |
| 8,121,702 B2 | 2/2012 | King |
| 8,123,684 B2 | 2/2012 | Zdeblick |
| 8,170,676 B2 | 5/2012 | Greenberg et al. |
| 8,171,621 B2 | 5/2012 | Swanson et al. |
| 8,172,762 B2 | 5/2012 | Robertson |
| 8,187,161 B2 | 5/2012 | Li et al. |
| 8,195,308 B2 | 6/2012 | Frank et al. |
| 8,204,586 B2 | 6/2012 | Zdeblick |
| 8,224,417 B2 | 7/2012 | Vetter |
| 8,244,377 B1 | 8/2012 | Pianca et al. |
| 8,258,962 B2 | 9/2012 | Robertson et al. |
| 8,261,428 B2 | 9/2012 | Fang et al. |
| 8,271,094 B1 | 9/2012 | Moffitt et al. |
| 8,280,514 B2 | 10/2012 | Lozano et al. |
| 8,295,943 B2 | 10/2012 | Eggen et al. |
| 8,315,686 B2 | 11/2012 | Llinas et al. |
| 8,321,025 B2 | 11/2012 | Bedenbaugh |
| 8,332,020 B2 | 12/2012 | Zdeblick |
| 8,332,046 B2 | 12/2012 | Anderson et al. |
| 8,355,768 B2 | 1/2013 | Masmanidis et al. |
| 8,374,703 B2 | 2/2013 | Imran |
| 8,412,347 B2 | 4/2013 | Zdeblick |
| 8,463,353 B2 | 6/2013 | Seymour et al. |
| 8,463,398 B2 | 6/2013 | Jackson et al. |
| 8,467,877 B2 | 6/2013 | Imran |
| 8,473,061 B2 | 6/2013 | Moffitt et al. |
| 8,473,069 B2 | 6/2013 | Bi et al. |
| 8,489,203 B2 | 7/2013 | Ortmann |
| 8,509,872 B2 | 8/2013 | Lee et al. |
| 8,509,920 B2 | 8/2013 | Wahlstrand et al. |
| 8,560,085 B2 | 10/2013 | Moffitt et al. |
| 8,565,894 B2 | 10/2013 | Vetter et al. |
| 8,571,665 B2 | 10/2013 | Moffitt et al. |
| 8,583,253 B1 | 11/2013 | Shi et al. |
| 8,620,452 B2 | 12/2013 | King et al. |
| 8,626,312 B2 | 1/2014 | King et al. |
| 8,634,934 B2 | 1/2014 | Kokones et al. |
| 8,644,903 B1 | 2/2014 | Osa et al. |
| 8,649,879 B2 | 2/2014 | Digiore et al. |
| 8,666,509 B2 | 3/2014 | Howard et al. |
| 8,694,105 B2 | 4/2014 | Martens et al. |
| 8,694,123 B2 | 4/2014 | Wahlstrand et al. |
| 8,694,127 B2 | 4/2014 | Pianca et al. |
| 8,731,673 B2 | 5/2014 | Vetter et al. |
| 8,738,154 B2 | 5/2014 | Zdeblick et al. |
| 8,744,596 B2 | 6/2014 | Howard |
| 8,755,906 B2 | 6/2014 | Moffitt et al. |
| 8,762,065 B2 | 6/2014 | Dilorenzo |
| 8,774,891 B1 | 7/2014 | Osa et al. |
| 8,788,056 B2 | 7/2014 | King et al. |
| 8,788,063 B2 | 7/2014 | Chen |
| 8,788,064 B2 | 7/2014 | Mercanzini et al. |
| 8,792,993 B2 | 7/2014 | Pianca et al. |
| 8,800,140 B2 | 8/2014 | Hetke et al. |
| 8,825,175 B2 | 9/2014 | King |
| 8,831,739 B2 | 9/2014 | Mccreery et al. |
| 8,831,742 B2 | 9/2014 | Pianca et al. |
| 8,849,369 B2 | 9/2014 | Cogan et al. |
| 8,849,415 B2 | 9/2014 | Bedenbaugh |
| 8,862,242 B2 | 10/2014 | Pianca |
| 8,874,232 B2 | 10/2014 | Chen |
| 8,875,391 B2 | 11/2014 | Pianca et al. |
| 8,897,891 B2 | 11/2014 | Romero |
| 8,923,982 B2 | 12/2014 | Howard |
| 8,938,300 B2 | 1/2015 | Rosero |
| 8,938,308 B2 | 1/2015 | Meadows |
| 8,958,862 B2 | 2/2015 | Hetke et al. |
| 8,977,335 B2 | 3/2015 | Putz |
| 8,989,864 B2 | 3/2015 | Funderburk et al. |
| 9,014,796 B2 | 4/2015 | Kipke et al. |
| 9,044,590 B2 | 6/2015 | Greenberg et al. |
| 9,061,134 B2 | 6/2015 | Askin et al. |
| 9,079,013 B2 | 7/2015 | Digiore et al. |
| 9,089,689 B2 | 7/2015 | Govea |
| 9,089,690 B2 | 7/2015 | Greenberg et al. |
| 9,095,267 B2 | 8/2015 | Halpern et al. |
| 9,149,630 B2 | 10/2015 | Howard et al. |
| 9,211,402 B2 | 12/2015 | Moffitt et al. |
| 9,220,897 B2 | 12/2015 | Perryman et al. |
| 9,227,050 B2 | 1/2016 | Romero |
| 9,248,272 B2 | 2/2016 | Romero |
| 9,248,275 B2 | 2/2016 | Digiore et al. |
| 9,283,375 B2 | 3/2016 | Moffitt et al. |
| 9,289,596 B2 | 3/2016 | Leven |
| 9,295,830 B2 | 3/2016 | Pianca |
| 9,314,614 B2 | 4/2016 | Bedenbaugh |
| 9,364,659 B1 | 6/2016 | Rao |
| 9,381,347 B2 | 7/2016 | Howard et al. |
| 9,381,348 B2 | 7/2016 | Romero et al. |
| 9,381,356 B2 | 7/2016 | Parker et al. |
| 9,427,567 B2 | 8/2016 | Romero |

(56) References Cited

U.S. PATENT DOCUMENTS

| | | |
|---|---|---|
| 9,474,894 B2 * | 10/2016 | Mercanzini .......... A61N 1/0534 |
| 9,474,895 B2 | 10/2016 | Digiore et al. |
| 9,498,620 B2 | 11/2016 | Romero et al. |
| 9,592,377 B2 | 3/2017 | Greenberg et al. |
| 9,604,051 B2 | 3/2017 | Vetter et al. |
| 9,700,715 B2 | 7/2017 | Dou |
| 9,775,983 B2 | 10/2017 | Digiore et al. |
| 9,775,988 B2 | 10/2017 | Govea et al. |
| 9,827,413 B2 | 11/2017 | Barker et al. |
| 9,833,611 B2 | 12/2017 | Govea et al. |
| 9,855,428 B2 | 1/2018 | Henry et al. |
| 9,861,288 B2 | 1/2018 | Ma et al. |
| 9,925,368 B2 | 3/2018 | Ryu et al. |
| 2002/0062143 A1 | 5/2002 | Baudino et al. |
| 2003/0004553 A1 | 1/2003 | Grill et al. |
| 2003/0023282 A1 | 1/2003 | Barrett et al. |
| 2003/0036780 A1 | 2/2003 | Barrett et al. |
| 2003/0060822 A1 | 3/2003 | Schaer et al. |
| 2003/0083724 A1 | 5/2003 | Jog et al. |
| 2003/0100823 A1 | 5/2003 | Kipke et al. |
| 2003/0135253 A1 | 7/2003 | Kokones et al. |
| 2003/0176892 A1 | 9/2003 | Shalev |
| 2004/0002635 A1 | 1/2004 | Hargrove et al. |
| 2004/0015205 A1 | 1/2004 | Whitehurst et al. |
| 2004/0039434 A1 | 2/2004 | Schrom et al. |
| 2004/0098074 A1 | 5/2004 | Erickson et al. |
| 2004/0102828 A1 | 5/2004 | Lowry et al. |
| 2004/0122335 A1 | 6/2004 | Sackellares et al. |
| 2004/0133390 A1 | 7/2004 | Osorio et al. |
| 2004/0138517 A1 | 7/2004 | Osorio et al. |
| 2004/0138536 A1 | 7/2004 | Frei et al. |
| 2004/0138720 A1 | 7/2004 | Naisberg et al. |
| 2004/0138722 A1 | 7/2004 | Carroll et al. |
| 2004/0152958 A1 | 8/2004 | Frei et al. |
| 2004/0172089 A1 | 9/2004 | Whitehurst et al. |
| 2004/0193021 A1 | 9/2004 | Zdeblick et al. |
| 2004/0215288 A1 | 10/2004 | Lee et al. |
| 2004/0220637 A1 | 11/2004 | Zdeblick et al. |
| 2004/0225335 A1 | 11/2004 | Whitehurst et al. |
| 2004/0243011 A1 | 12/2004 | Plaza |
| 2004/0249417 A1 | 12/2004 | Ransbury et al. |
| 2004/0254483 A1 | 12/2004 | Zdeblick et al. |
| 2005/0004627 A1 | 1/2005 | Gibson et al. |
| 2005/0008660 A1 | 1/2005 | Kipke et al. |
| 2005/0010261 A1 | 1/2005 | Luders et al. |
| 2005/0021103 A1 | 1/2005 | Dilorenzo |
| 2005/0027284 A1 | 2/2005 | Lozano et al. |
| 2005/0033136 A1 | 2/2005 | Govari et al. |
| 2005/0038489 A1 | 2/2005 | Grill |
| 2005/0049655 A1 | 3/2005 | Boveja et al. |
| 2005/0070971 A1 | 3/2005 | Fowler et al. |
| 2005/0075681 A1 | 4/2005 | Rezai et al. |
| 2005/0113882 A1 | 5/2005 | Cameron et al. |
| 2005/0137647 A1 | 6/2005 | Wallace et al. |
| 2005/0143790 A1 | 6/2005 | Kipke et al. |
| 2005/0154425 A1 | 7/2005 | Boveja et al. |
| 2005/0171558 A1 | 8/2005 | Abovitz et al. |
| 2005/0182455 A1 | 8/2005 | Thrope et al. |
| 2005/0209511 A1 | 9/2005 | Heruth et al. |
| 2005/0209513 A1 | 9/2005 | Heruth et al. |
| 2005/0209643 A1 | 9/2005 | Heruth et al. |
| 2005/0222642 A1 | 10/2005 | Przybyszewski et al. |
| 2005/0240242 A1 | 10/2005 | Dilorenzo |
| 2005/0245988 A1 | 11/2005 | Miesel |
| 2006/0004422 A1 | 1/2006 | De Ridder |
| 2006/0030897 A1 | 2/2006 | Gilmer et al. |
| 2006/0041295 A1 | 2/2006 | Osypka |
| 2006/0049957 A1 | 3/2006 | Surgenor et al. |
| 2006/0058588 A1 | 3/2006 | Zdeblick |
| 2006/0058727 A1 | 3/2006 | Bernabei |
| 2006/0058855 A1 | 3/2006 | Gill |
| 2006/0095105 A1 | 5/2006 | Jog et al. |
| 2006/0116581 A1 | 6/2006 | Zdeblick et al. |
| 2006/0129203 A1 | 6/2006 | Garabedian et al. |
| 2006/0135877 A1 | 6/2006 | Giftakis et al. |
| 2006/0149336 A1 | 7/2006 | Meadows |
| 2006/0149337 A1 | 7/2006 | John |
| 2006/0167497 A1 | 7/2006 | Armstrong et al. |
| 2006/0173263 A1 | 8/2006 | He et al. |
| 2006/0173510 A1 | 8/2006 | Besio et al. |
| 2006/0178709 A1 | 8/2006 | Foster et al. |
| 2006/0195154 A1 | 8/2006 | Jaax et al. |
| 2006/0200206 A1 | 9/2006 | Firlik et al. |
| 2006/0212090 A1 | 9/2006 | Lozano et al. |
| 2006/0241717 A1 | 10/2006 | Whitehurst et al. |
| 2006/0258951 A1 | 11/2006 | Bleich et al. |
| 2006/0264777 A1 | 11/2006 | Drew |
| 2006/0276866 A1 | 12/2006 | McCreery |
| 2006/0282014 A1 | 12/2006 | Kipke et al. |
| 2006/0293720 A1 | 12/2006 | Dilorenzo |
| 2006/0293721 A1 | 12/2006 | Tarver et al. |
| 2007/0027498 A1 | 2/2007 | Maschino et al. |
| 2007/0027500 A1 | 2/2007 | Maschino et al. |
| 2007/0027514 A1 | 2/2007 | Gerber |
| 2007/0043268 A1 | 2/2007 | Russell |
| 2007/0060974 A1 | 3/2007 | Lozano |
| 2007/0067002 A1 | 3/2007 | Lozano |
| 2007/0067003 A1 | 3/2007 | Sanchez et al. |
| 2007/0088403 A1 | 4/2007 | Wyler et al. |
| 2007/0088404 A1 | 4/2007 | Wyler et al. |
| 2007/0093870 A1 | 4/2007 | Maschino |
| 2007/0100389 A1 | 5/2007 | Jaax et al. |
| 2007/0100392 A1 | 5/2007 | Maschino et al. |
| 2007/0100393 A1 | 5/2007 | Whitehurst et al. |
| 2007/0100398 A1 | 5/2007 | Sloan |
| 2007/0106143 A1 | 5/2007 | Flaherty |
| 2007/0123765 A1 | 5/2007 | Hetke et al. |
| 2007/0123944 A1 | 5/2007 | Zdeblick |
| 2007/0135721 A1 | 6/2007 | Zdeblick |
| 2007/0142872 A1 | 6/2007 | Mickle et al. |
| 2007/0150024 A1 | 6/2007 | Leyde et al. |
| 2007/0173890 A1 | 7/2007 | Armstrong |
| 2007/0173896 A1 | 7/2007 | Zdeblick |
| 2007/0173897 A1 | 7/2007 | Zdeblick |
| 2007/0173901 A1 | 7/2007 | Reeve |
| 2007/0173908 A1 | 7/2007 | Begnaud |
| 2007/0179558 A1 | 8/2007 | Gliner et al. |
| 2007/0179569 A1 | 8/2007 | Zdeblick |
| 2007/0185537 A1 | 8/2007 | Zdeblick |
| 2007/0185544 A1 | 8/2007 | Dawant et al. |
| 2007/0185548 A1 | 8/2007 | Zdeblick |
| 2007/0185549 A1 | 8/2007 | Zdeblick |
| 2007/0197892 A1 | 8/2007 | Shen et al. |
| 2007/0203537 A1 | 8/2007 | Goetz et al. |
| 2007/0203546 A1 | 8/2007 | Stone et al. |
| 2007/0208394 A1 | 9/2007 | King et al. |
| 2007/0213784 A1 | 9/2007 | Pless |
| 2007/0213785 A1 | 9/2007 | Osorio et al. |
| 2007/0213786 A1 | 9/2007 | Sackellares et al. |
| 2007/0219591 A1 | 9/2007 | Zdeblick et al. |
| 2007/0225674 A1 | 9/2007 | Molnar et al. |
| 2007/0225773 A1 | 9/2007 | Shen et al. |
| 2007/0225774 A1 | 9/2007 | Eskandar et al. |
| 2007/0233192 A1 | 10/2007 | Craig |
| 2007/0249953 A1 | 10/2007 | Frei et al. |
| 2007/0249954 A1 | 10/2007 | Virag et al. |
| 2007/0250133 A1 | 10/2007 | Carlson et al. |
| 2007/0255323 A1 | 11/2007 | Werder et al. |
| 2007/0255338 A1 | 11/2007 | Wahlstrand |
| 2007/0255374 A1 | 11/2007 | Kolafa et al. |
| 2007/0255531 A1 | 11/2007 | Drew |
| 2007/0265683 A1 | 11/2007 | Ehrlich |
| 2007/0282389 A1 | 12/2007 | Moxon et al. |
| 2007/0293908 A1 | 12/2007 | Cowan et al. |
| 2008/0021514 A1 | 1/2008 | Pless |
| 2008/0021517 A1 | 1/2008 | Dietrich |
| 2008/0027289 A1 | 1/2008 | Zdeblick |
| 2008/0027487 A1 | 1/2008 | Patel et al. |
| 2008/0027503 A1 | 1/2008 | Marrosu et al. |
| 2008/0027504 A1 | 1/2008 | Bedenbaugh |
| 2008/0027540 A1 | 1/2008 | Cumming |
| 2008/0039895 A1 | 2/2008 | Fowler et al. |
| 2008/0046012 A1 | 2/2008 | Covalin et al. |
| 2008/0046013 A1 | 2/2008 | Lozano |

(56) References Cited

U.S. PATENT DOCUMENTS

| | | |
|---|---|---|
| 2008/0058630 A1 | 3/2008 | Robertson |
| 2008/0077186 A1 | 3/2008 | Thompson et al. |
| 2008/0077191 A1 | 3/2008 | Morrell |
| 2008/0103547 A1 | 5/2008 | Okun et al. |
| 2008/0103548 A1 | 5/2008 | Fowler et al. |
| 2008/0103578 A1 | 5/2008 | Gerber |
| 2008/0114417 A1 | 5/2008 | Leyde |
| 2008/0119900 A1 | 5/2008 | Dilorenzo |
| 2008/0139870 A1 | 6/2008 | Gliner et al. |
| 2008/0140152 A1 | 6/2008 | Imran et al. |
| 2008/0154328 A1 | 6/2008 | Thompson et al. |
| 2008/0154331 A1 | 6/2008 | John et al. |
| 2008/0161881 A1 | 7/2008 | Firlik et al. |
| 2008/0161896 A1 | 7/2008 | Sauter-Starace et al. |
| 2008/0172103 A1 | 7/2008 | Kao et al. |
| 2008/0177196 A1 | 7/2008 | Burdick et al. |
| 2008/0188905 A1 | 8/2008 | Swartz |
| 2008/0195166 A1 | 8/2008 | Sun et al. |
| 2008/0195227 A1 | 8/2008 | Boling et al. |
| 2008/0208283 A1 | 8/2008 | Vetter et al. |
| 2008/0208287 A1 | 8/2008 | Palermo et al. |
| 2008/0215125 A1 | 9/2008 | Farah et al. |
| 2008/0221642 A1 | 9/2008 | Humayun et al. |
| 2008/0242976 A1 | 10/2008 | Robertson et al. |
| 2008/0255439 A1 | 10/2008 | Tang et al. |
| 2008/0255629 A1 | 10/2008 | Jenson et al. |
| 2008/0255647 A1 | 10/2008 | Jensen et al. |
| 2008/0269835 A1 | 10/2008 | Carlson et al. |
| 2008/0269842 A1 | 10/2008 | Giftakis et al. |
| 2008/0269854 A1 | 10/2008 | Hegland et al. |
| 2008/0275526 A1 | 11/2008 | Lozano |
| 2008/0284599 A1 | 11/2008 | Zdeblick et al. |
| 2008/0294218 A1 | 11/2008 | Savage et al. |
| 2008/0300652 A1 | 12/2008 | Lim et al. |
| 2008/0306394 A1 | 12/2008 | Zdeblick et al. |
| 2008/0312726 A1 | 12/2008 | Frank et al. |
| 2008/0316020 A1 | 12/2008 | Robertson et al. |
| 2009/0027504 A1 | 1/2009 | Lim et al. |
| 2009/0062879 A1 | 3/2009 | Li et al. |
| 2009/0082645 A1 | 3/2009 | Hafezi et al. |
| 2009/0105784 A1 | 4/2009 | Massoud-Ansari et al. |
| 2009/0118806 A1 | 5/2009 | Vetter et al. |
| 2009/0132042 A1 | 5/2009 | Hetke et al. |
| 2009/0171416 A1 | 7/2009 | Firlik et al. |
| 2009/0177144 A1 | 7/2009 | Masmanidis et al. |
| 2009/0187196 A1 | 7/2009 | Vetter |
| 2009/0204183 A1 | 8/2009 | Kreidler et al. |
| 2009/0240314 A1 | 9/2009 | Kong et al. |
| 2009/0248122 A1 | 10/2009 | Pianca |
| 2009/0253977 A1 | 10/2009 | Kipke et al. |
| 2009/0256702 A1 | 10/2009 | Robertson et al. |
| 2009/0292325 A1 | 11/2009 | Cederna et al. |
| 2009/0299174 A1 | 12/2009 | Wright et al. |
| 2009/0306728 A1 | 12/2009 | Wright et al. |
| 2009/0306729 A1 | 12/2009 | Doerr |
| 2009/0312770 A1 | 12/2009 | Kozai et al. |
| 2009/0318824 A1 | 12/2009 | Nishida et al. |
| 2009/0325424 A1 | 12/2009 | Aarts et al. |
| 2010/0014541 A1 | 1/2010 | Harriman |
| 2010/0015274 A1 | 1/2010 | Fill |
| 2010/0030298 A1 | 2/2010 | Martens et al. |
| 2010/0036468 A1 | 2/2010 | Decre et al. |
| 2010/0069717 A1 | 3/2010 | Hafezi et al. |
| 2010/0076536 A1 | 3/2010 | Merz et al. |
| 2010/0087853 A1 | 4/2010 | Kipke et al. |
| 2010/0100152 A1 | 4/2010 | Martens et al. |
| 2010/0106178 A1 | 4/2010 | Obermiller et al. |
| 2010/0114193 A1 | 5/2010 | Lozano et al. |
| 2010/0114234 A1 | 5/2010 | Zdeblick |
| 2010/0114250 A1 | 5/2010 | Zdeblick |
| 2010/0130844 A1 | 5/2010 | Williams et al. |
| 2010/0145216 A1 | 6/2010 | He et al. |
| 2010/0145414 A1 | 6/2010 | Decre et al. |
| 2010/0152747 A1 | 6/2010 | Padiy et al. |
| 2010/0184495 A1 | 7/2010 | Levy et al. |
| 2010/0198315 A1 | 8/2010 | Martens et al. |
| 2010/0249883 A1 | 9/2010 | Zdeblick |
| 2010/0274305 A1 | 10/2010 | Gliner et al. |
| 2010/0292602 A1 | 11/2010 | Worrell et al. |
| 2010/0298908 A1 | 11/2010 | Vardiman |
| 2010/0298917 A1 | 11/2010 | Vardiman |
| 2010/0298918 A1 | 11/2010 | Vardiman |
| 2010/0312188 A1 | 12/2010 | Robertson et al. |
| 2010/0312228 A1 | 12/2010 | Zdeblick et al. |
| 2010/0318163 A1 | 12/2010 | Zdeblick |
| 2010/0331807 A1 | 12/2010 | Whitehurst et al. |
| 2011/0001488 A1 | 1/2011 | Behzadi et al. |
| 2011/0022124 A1 | 1/2011 | Zdeblick et al. |
| 2011/0034964 A1 | 2/2011 | Bi et al. |
| 2011/0034970 A1 | 2/2011 | Barker |
| 2011/0040203 A1 | 2/2011 | Savage et al. |
| 2011/0071766 A1 | 3/2011 | Dolan et al. |
| 2011/0130809 A1 | 6/2011 | Zdeblick |
| 2011/0152988 A1 | 6/2011 | Whitehurst et al. |
| 2011/0154655 A1 | 6/2011 | Hetke et al. |
| 2011/0184495 A1 | 7/2011 | Wang et al. |
| 2011/0190860 A1 | 8/2011 | Harberts et al. |
| 2011/0196454 A1 | 8/2011 | Strand et al. |
| 2011/0208225 A1 | 8/2011 | Martens et al. |
| 2011/0213382 A1 | 9/2011 | Decre et al. |
| 2011/0218417 A1 | 9/2011 | Boogaard et al. |
| 2011/0224757 A1 | 9/2011 | Zdeblick et al. |
| 2011/0224765 A1 | 9/2011 | Harberts et al. |
| 2011/0224766 A1 | 9/2011 | Tol et al. |
| 2011/0282179 A1 | 11/2011 | Zdeblick |
| 2012/0004520 A1 | 1/2012 | Whitworth et al. |
| 2012/0004527 A1 | 1/2012 | Thompson et al. |
| 2012/0004716 A1 | 1/2012 | Langhammer et al. |
| 2012/0007734 A1 | 1/2012 | Berkman et al. |
| 2012/0022341 A1 | 1/2012 | Zdeblick |
| 2012/0035684 A1 | 2/2012 | Thompson et al. |
| 2012/0053344 A1 | 3/2012 | Lagos Gonzalez |
| 2012/0059444 A1 | 3/2012 | Pardoel et al. |
| 2012/0062379 A1 | 3/2012 | Hafezi et al. |
| 2012/0095355 A1 | 4/2012 | Zdeblick |
| 2012/0109262 A1 | 5/2012 | Martens |
| 2012/0109599 A1 | 5/2012 | Martens |
| 2012/0116188 A1 | 5/2012 | Frank et al. |
| 2012/0136420 A1 | 5/2012 | Pardoel et al. |
| 2012/0150256 A1 | 6/2012 | Martens |
| 2012/0184837 A1 | 7/2012 | Martens et al. |
| 2012/0253442 A1 | 10/2012 | Gliner et al. |
| 2012/0277821 A1 | 11/2012 | Martens et al. |
| 2012/0296444 A1 | 11/2012 | Greenberg et al. |
| 2012/0303088 A1 | 11/2012 | Van Kaam et al. |
| 2012/0303089 A1 | 11/2012 | Martens et al. |
| 2012/0303107 A1 | 11/2012 | Decre et al. |
| 2012/0316630 A1 | 12/2012 | Firlik et al. |
| 2013/0009691 A1 | 1/2013 | Blanken et al. |
| 2013/0030366 A1 | 1/2013 | Robertson et al. |
| 2013/0046356 A1 | 2/2013 | Jensen et al. |
| 2013/0060102 A1 | 3/2013 | Zdeblick |
| 2013/0085361 A1 | 4/2013 | Mercanzini et al. |
| 2013/0131754 A1 | 5/2013 | Sarvazyan |
| 2013/0144132 A1 | 6/2013 | Hafezi et al. |
| 2013/0172716 A1 | 7/2013 | Lozano et al. |
| 2013/0193950 A1 | 8/2013 | Hafezi et al. |
| 2013/0204318 A1 | 8/2013 | Young |
| 2013/0223028 A1 | 8/2013 | Arne et al. |
| 2013/0231188 A1 | 9/2013 | Berberich et al. |
| 2013/0282090 A1 | 10/2013 | Decre et al. |
| 2013/0345780 A1 | 12/2013 | Tabada et al. |
| 2013/0345789 A1 | 12/2013 | Havel et al. |
| 2014/0039578 A1 | 2/2014 | Whitehurst et al. |
| 2015/0051678 A1 | 2/2015 | Reed et al. |
| 2015/0142090 A1 | 5/2015 | Duijsens et al. |
| 2015/0151111 A1 | 6/2015 | Pianca et al. |
| 2015/0209578 A1 | 7/2015 | Kast et al. |
| 2015/0290452 A1 | 10/2015 | Kokones et al. |
| 2015/0360023 A1 | 12/2015 | Howard et al. |
| 2016/0008592 A1 | 1/2016 | Romero et al. |
| 2016/0023003 A1 | 1/2016 | Perryman et al. |
| 2016/0074651 A1 | 3/2016 | Moffitt et al. |
| 2016/0331953 A1 | 11/2016 | Reed et al. |

(56) References Cited

U.S. PATENT DOCUMENTS

| | | |
|---|---|---|
| 2016/0331975 A1 | 11/2016 | Henry et al. |
| 2016/0361535 A1 | 12/2016 | Perryman et al. |
| 2017/0007813 A1 | 1/2017 | Negi et al. |
| 2017/0049345 A1 | 2/2017 | Single |
| 2017/0266432 A1 | 9/2017 | Seeley et al. |
| 2017/0296808 A1 | 10/2017 | Greenberg et al. |
| 2017/0361101 A1 | 12/2017 | Single |

FOREIGN PATENT DOCUMENTS

| | | |
|---|---|---|
| EP | 0 892 654 | 1/1999 |
| EP | 0 895 483 B1 | 2/1999 |
| EP | 0 959 942 B1 | 12/1999 |
| EP | 1 048 319 B1 | 11/2000 |
| EP | 1 062 973 B1 | 12/2000 |
| EP | 1 102 607 B1 | 5/2001 |
| EP | 1 257 320 B1 | 11/2002 |
| EP | 1 446 189 B1 | 8/2004 |
| EP | 1 514 576 B1 | 3/2005 |
| EP | 1 750 798 | 2/2007 |
| EP | 1 890 764 | 2/2008 |
| EP | 1 931 419 | 6/2008 |
| EP | 1 985 579 A2 | 10/2008 |
| EP | 1 993 665 B1 | 11/2008 |
| EP | 2 046 441 | 4/2009 |
| EP | 2 066 396 B1 | 6/2009 |
| EP | 2 069 003 | 6/2009 |
| EP | 2 131 916 | 12/2009 |
| EP | 2 167 188 | 3/2010 |
| EP | 2 320 221 | 5/2011 |
| EP | 2 341 979 | 7/2011 |
| EP | 2 389 975 B1 | 11/2011 |
| EP | 2 456 513 A1 | 5/2012 |
| EP | 2 542 303 A1 | 1/2013 |
| EP | 2 559 454 A1 | 2/2013 |
| EP | 2 604 313 A1 | 6/2013 |
| EP | 2 620 179 A1 | 7/2013 |
| EP | 2 623 154 A1 | 8/2013 |
| EP | 2 626 108 A1 | 8/2013 |
| EP | 2 626 109 A1 | 8/2013 |
| EP | 2 626 110 A1 | 8/2013 |
| EP | 2 626 111 A1 | 8/2013 |
| EP | 2 656 875 A1 | 10/2013 |
| EP | 2 656 876 A1 | 10/2013 |
| EP | 2 674 193 A1 | 12/2013 |
| WO | WO-98/10010 | 3/1998 |
| WO | WO-02/068042 | 9/2002 |
| WO | WO-03/022354 A2 | 3/2003 |
| WO | WO-03/028521 A2 | 4/2003 |
| WO | WO-03/066152 A2 | 8/2003 |
| WO | WO-03/066153 A2 | 8/2003 |
| WO | WO-03/066157 A2 | 8/2003 |
| WO | WO-2004/043536 A1 | 5/2004 |
| WO | WO-2018/068013 A1 | 5/2004 |
| WO | WO-2004/045707 A1 | 6/2004 |
| WO | WO-2005/002467 A2 | 1/2005 |
| WO | WO-2005/067792 A1 | 7/2005 |
| WO | WO-2005/112216 A2 | 11/2005 |
| WO | WO-2006/047625 | 5/2006 |
| WO | WO-2006/104432 A1 | 10/2006 |
| WO | WO-2007/002144 A2 | 1/2007 |
| WO | WO-2007/009070 A2 | 1/2007 |
| WO | WO-2007/011611 A2 | 1/2007 |
| WO | WO-2007/025356 A1 | 3/2007 |
| WO | WO-2007/028003 A2 | 3/2007 |
| WO | WO-2007/042999 A2 | 4/2007 |
| WO | WO-2007/092330 A1 | 8/2007 |
| WO | WO-2007/100428 A1 | 9/2007 |
| WO | WO-2007/108718 A1 | 9/2007 |
| WO | WO-2008/003318 A1 | 1/2008 |
| WO | WO-2008/005478 A2 | 1/2008 |
| WO | WO-2008/016881 A2 | 2/2008 |
| WO | WO-2008/035285 A2 | 3/2008 |
| WO | WO-2008/035344 A2 | 3/2008 |
| WO | WO-2008/051463 A2 | 5/2008 |
| WO | WO-2008/064269 A2 | 5/2008 |
| WO | WO-2008/068759 A2 | 6/2008 |
| WO | WO-2008/075294 A1 | 6/2008 |
| WO | WO-2008/077440 A1 | 7/2008 |
| WO | WO-2008/089726 A1 | 7/2008 |
| WO | WO-2008/107822 A1 | 9/2008 |
| WO | WO-2008/109298 A2 | 9/2008 |
| WO | WO-2008/133616 A1 | 11/2008 |
| WO | WO-2008/133683 A1 | 11/2008 |
| WO | WO-2008/138305 A1 | 11/2008 |
| WO | WO-2010/014686 A1 | 2/2010 |
| WO | WO-2010/055421 A1 | 5/2010 |
| WO | WO-2011/000791 A1 | 1/2011 |
| WO | WO-2011/115999 A1 | 9/2011 |
| WO | WO-2013/014206 A1 | 1/2013 |
| WO | WO-2016/030823 | 3/2016 |

OTHER PUBLICATIONS

US 8,469,885, 06/2013, Hafezi et al. (withdrawn)
U.S. Appl. No. 07/151,961, filed Feb. 3, 1988, Masahiko Okunuki et al.
Australian Patent Examination Report No. 1 dated Jan. 30, 2014 in corresponding Australian Application No. 2010326613, 2 pages.
Australian Patent Examination Report No. 1 dated Jan. 31, 2014 in corresponding Australian Application No. 2009315316, 3 pages.
Benabid, et al. "Combined (Thalamotomy and Stimulation) Stereotactic Surgery of the VIM Thalamic Nucleus for Bilateral Parkinson Disease", Proceedings of the Meeting of the American Society for Stereotactic and Functional Neurosurgery, Montreal 1987 Appl. Neurophysiol. 50: 344-346.
Canadian Office Action for Application No. 2,743,575 dated Sep. 25, 2014, 3 pages.
Cogan, S., et al. "Plasma-enhanced chemical vapor deposited silicon carbide as an implantable dielectric coating." Journal of Biomedical Materials Research Part A 67.3 (2003): 856-867.
Communication from the European Patent Office in Application No. 09795810.2 dated Sep. 14, 2011.
Decision of Rejection and Decision for Dismissal of Amendment in JP Patent Application No. 2011-543841 dated May 15, 2014.
Decision of Rejection for Japanese Appl. Ser. No. 2012-541491 dated Oct. 26, 2015.
EIC Biomedical, "Thin-film Encapsulation for Neural Recording and Stimulation Electrodes", Silicon carbide and oxycarbide, Apr. 2008: pp. 1-2.
English translation of Notice of Reasons for Rejection in JP application No. 2011-543841 dated Oct. 21, 2013.
European Communication and Search Report for Application No. 09795810.2 dated Sep. 25, 2013.
European Communication dated May 22, 2013 including search report for EP application No. 12198290.4-1652.
European Search Report for Appl. Ser. No. 09803534.8 dated Jul. 21, 2011.
European Search Report for Appl. Ser. No. 13169272.5 dated Aug. 30, 2013.
European Search Report for application No. EP 14172592 dated Aug. 28, 2014, 8 pages.
Examination Report for EP09795810.2 dated Jun. 22, 2012.
Examination Report from European Patent Office in 09 795 810.2 dated May 8, 2014.
Examination Report in AU Patent Application No. 2009276603 dated Mar. 3, 2014.
Examination report in AU Patent Application No. 2011234422 dated Feb. 11, 2014.
Examination Report in EP Patent Application No. 11 711 884.4 dated Mar. 28, 2014.
Fierce Medical Devices, "Medtronic Announces First U.S. Implant of World's Smallest, Minimally Invasive Cardiac Pacemaker", Feb. 20, 2014, pp. 1-3.
Gibney, "St. Jude places its Nanostim leadless pacemaker in a U.K. patient", Fierce Medical Devices, Jan. 27, 2014, pp. 1-3.
International Preliminary Report on Patentability for PCT/EP2010/068658 dated Jun. 5, 2012.

(56) References Cited

OTHER PUBLICATIONS

International Preliminary Report on Patentability for PCT/IB2009/007715 dated May 17, 2011.
International Preliminary Report on Patentability for PCT/US2009/052077 dated Feb. 1, 2011.
International Search Report and Written Opinion for PCT Appl. Ser. No. PCT/IB2015/053610 dated Jul. 20, 2015.
International Search Report and Written Opinion for PCT Appl. Ser. No. PCT/IB2015/056437 dated Nov. 5, 2015.
International Search Report and Written Opinion for PCT Appl. Ser. No. PCT/IB2015/056438 dated Nov. 5, 2015.
International Search Report and Written Opinion for PCT/EP2010/068658 dated Mar. 21, 2011.
International Search Report and Written Opinion in Application No. PCT/EP2011/055045 dated Jul. 18, 2011.
International Search Report and Written Opinion in PCT/US09/52077 dated Sep. 25, 2009.
International Search Report for PCT/IB2009/007715 dated Apr. 22, 2010.
Notice of Allowance for U.S. Appl. No. 14/287,917 dated Apr. 15, 2015.
Notice of Allowance on U.S. Appl. No. 14/470,423 dated Jun. 15, 2016.
Notice of Reasons for Rejection for Japanese Patent Application No. 2011-543841 dated May 30, 2013.
Notice of Reasons for Rejection in JP Patent Application No. 2011-521276 dated Mar. 3, 2014.
Notice of Reasons for Rejection in JP Patent Application No. 2011-521276 dated May 30, 2013.
Notice of Reasons for Rejections for Japanese Patent Appl. Ser. No. 2012-541491 dated Aug. 28, 2014, 8 pages.
Office Action for Canadian Appl. Ser. No. 2732309 dated Dec. 7, 2015.
Office Action for Canadian Appl. Ser. No. 2743575 dated Jan. 21, 2015 (4 pages).
Office Action for Canadian Appl. Ser. No. 2743575 dated Jun. 11, 2015.
Office Action for Canadian Appl. Ser. No. 2743575 dated Sep. 14, 2015.
Office Action for EPO Appl. Ser. No. 10787404.2 dated May 6, 2015.
Office Action for EPO Appl. Ser. No. 14172592.9 dated Aug. 20, 2015.
Office Action for European Application No. 10787404.2 dated Mar. 26, 2013.
Office Action for Japanese Appl. Ser. No. 2013-501857 dated Jun. 1, 2015.
Office Action for Japanese Appl. Ser. No. 2013-501857 dated Sep. 17, 2014.
Office Action on U.S. Appl. No. 15/194,033 dated Aug. 22, 2016.
Pollak, et al. "Effets de la Stimulation du Noyau Sous-Thalamique Dans La Maladie De Parkinson", Rev. Neurol (Paris),149, 3, 175-176. Mason, Paris, 1993.
Rousche, et al., "Flexible polyimide-based intracortical electrode arrays with bioactive capability," IEEE Transactions on Biomedical Engineering 48(3): 361-371 (Mar. 2001).
Second Notice of Reasons for Rejection for Japanese Application No. 2012-541491 dated Apr. 8, 2015.
Sepulveda et al., "Finite Element Analysis of Current Pathways with Implanted Electrodes", J. Biomed. Eng. 1983, vol. 5, pp. 41-48.
U.S. Corrected Notice of Allowability for U.S. Appl. No. 14/470,356 dated May 18, 2016.
U.S. Notice of Allowance for U.S. Appl. No. 14/287,917 dated Jul. 20, 2015.
U.S. Notice of Allowance for U.S. Appl. No. 14/309,491 dated May 11, 2016.
U.S. Notice of Allowance for U.S. Appl. No. 14/316,154 dated Apr. 20, 2015.
U.S. Notice of Allowance for U.S. Appl. No. 14/470,356 dated Apr. 13, 2016.
U.S. Notice of Allowance for U.S. Appl. No. 14/470,356 dated Mar. 18, 2016.
U.S. Notice of Allowance for U.S. Appl. No. 13/512,936 dated Feb. 20, 2014.
U.S. Notice of Allowance for U.S. Appl. No. 13/512,936 dated Nov. 25, 2013.
U.S. Notice of Allowance for U.S. Appl. No. 13/056,261 dated May 8, 2014.
U.S. Notice of Allowance in U.S. Appl. No. 13/128,821 dated Dec. 24, 2013.
U.S. Notice of Allowance in U.S. Appl. No. 13/128,821 dated Mar. 25, 2014.
U.S. Office Action for U.S. Appl. No. 13/128,821 dated Nov. 14, 2013.
U.S. Office Action for U.S. Appl. No. 13/638,435 dated Feb. 10, 2016.
U.S. Office Action for U.S. Appl. No. 13/638,435 dated Jun. 30, 2015.
U.S. Office Action for U.S. Appl. No. 13/638,435 dated Mar. 12, 2015.
U.S. Office Action for U.S. Appl. No. 14/309,491 dated Jul. 28, 2015.
U.S. Office Action for U.S. Appl. No. 14/309,491 dated Mar. 3, 2016.
U.S. Office Action for U.S. Appl. No. 14/470,423 dated Jan. 21, 2016.
U.S. Office Action for U.S. Appl. No. 13/128,821 dated Dec. 14, 2012.
U.S. Office Action for U.S. Appl. No. 13/128,821 dated Apr. 24, 2012.
U.S. Office Action for U.S. Appl. No. 14/316,154 dated Dec. 18, 2014.
U.S. Office Action for U.S. Appl. No. 13/512,936 dated Aug. 14, 2013.
U.S. Office Action for U.S. Appl. No. 13/056,261 dated Jan. 9, 2014.
U.S. Office Action in U.S. Appl. No. 13/056,261 dated Aug. 7, 2013.
U.S. Office Action on U.S. Appl. No. 14/287,917 dated Sep. 26, 2014.
Written Opinion for PCT/EP2010/068658 dated Jun. 1, 2012.
Written Opinion for Singapore Application No. 201103393-3 dated May 2, 2012.
Written Opinion of the International Search Authority for PCT/IB2009/07715 dated May 12, 2011.
International Search Report and Written Opinion for PCT/IB2017/050551 dated Mar. 29, 2017.
Notice of Allowance on U.S. Appl. No. 15/426,816 dated Oct. 12, 2017.
Search Report for EP 16190439.6 dated Jul. 27, 2017.
US Notice of Allowance on U.S. Appl. No. 15/422,393 dated Aug. 14, 2017.
US Notice of Allowance on U.S. Appl. No. 15/422,393 dated Jul. 11, 2017.
US Notice of Allowance on U.S. Appl. No. 15/422,393 dated Oct. 25, 2017.

* cited by examiner

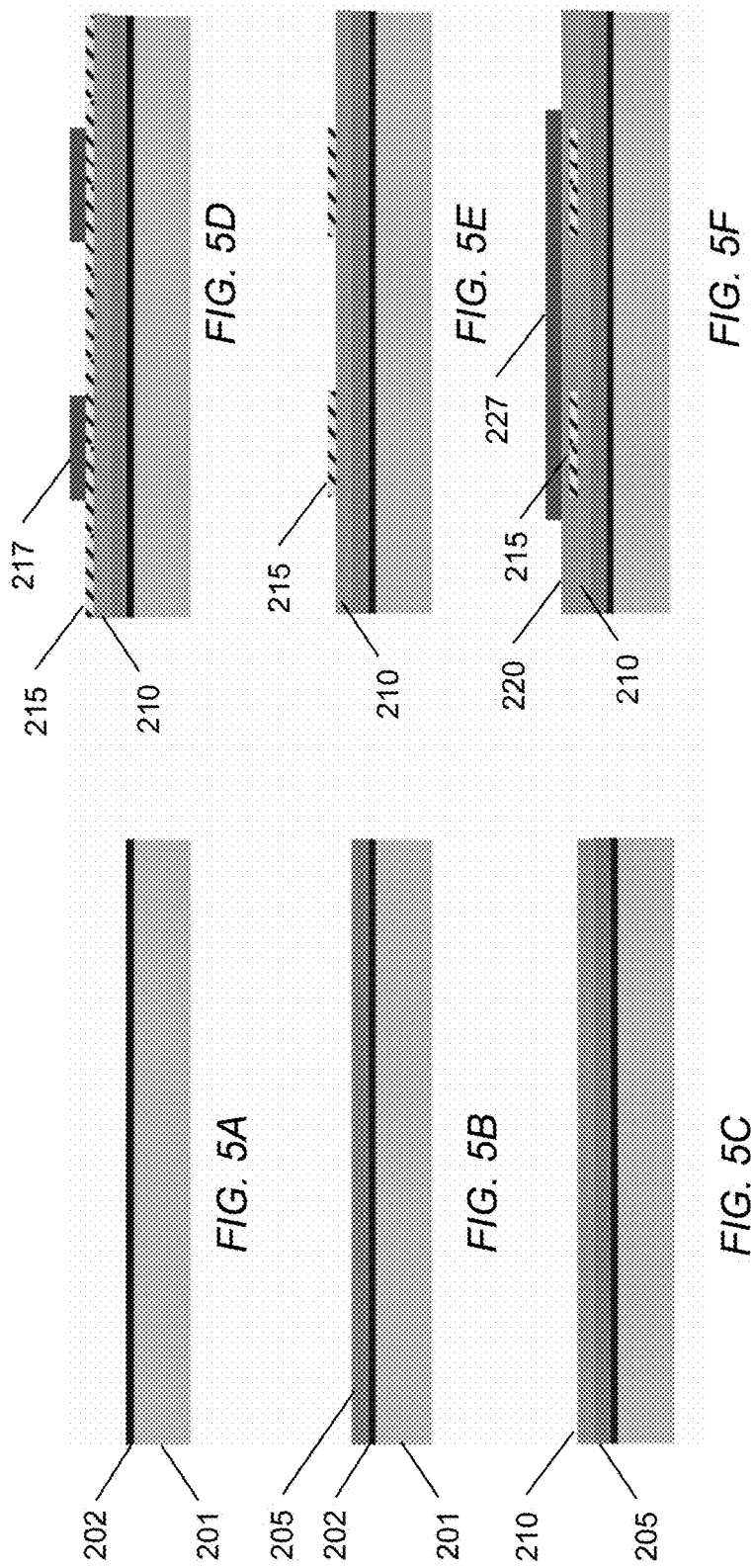

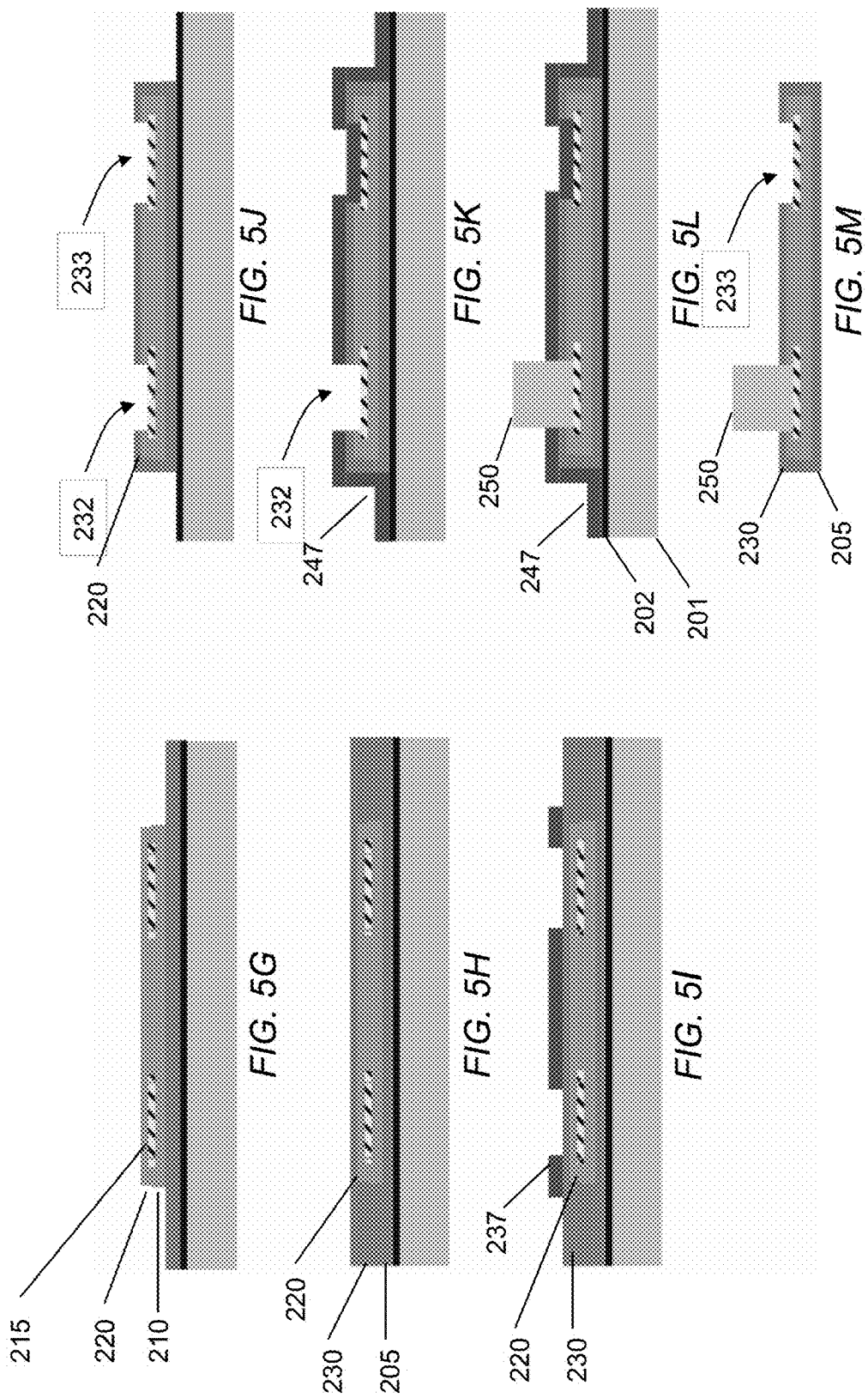

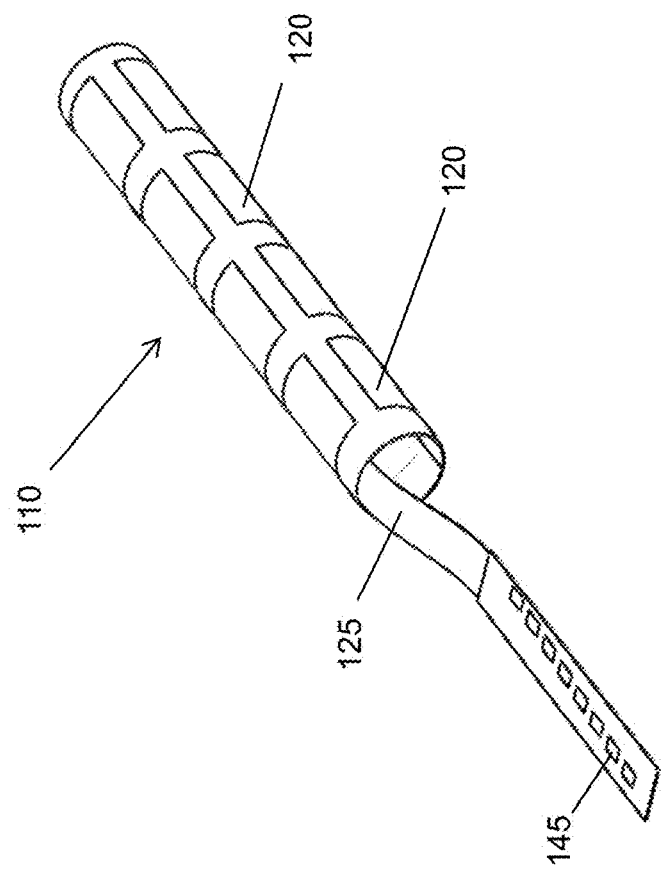
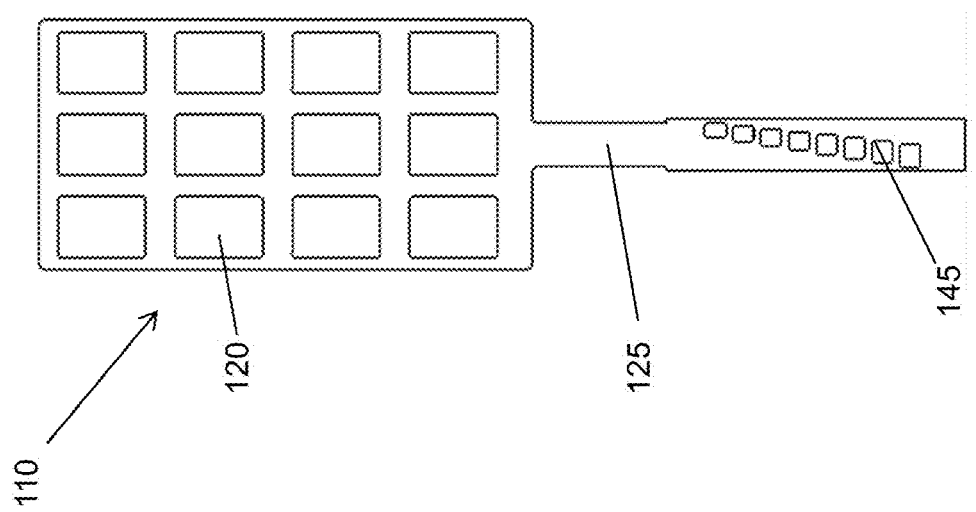
FIG. 6B
FIG. 6A

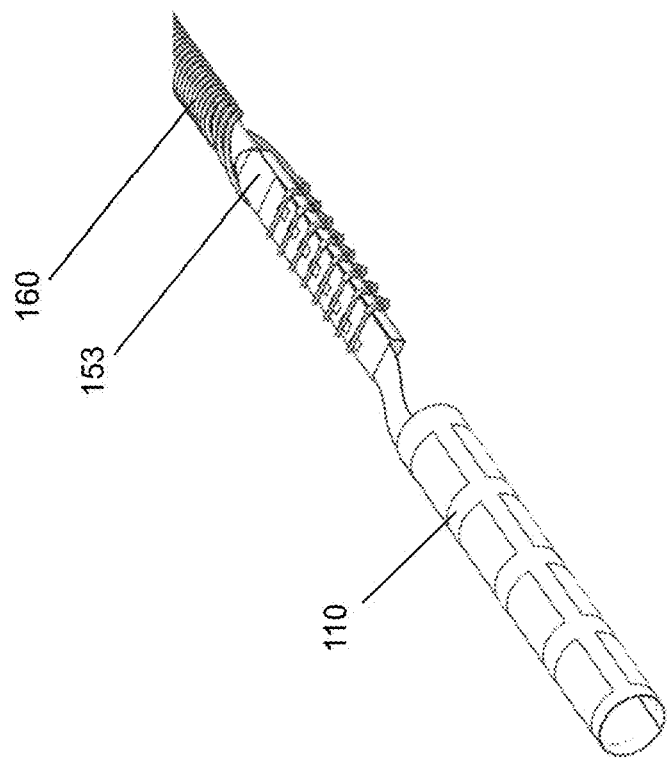
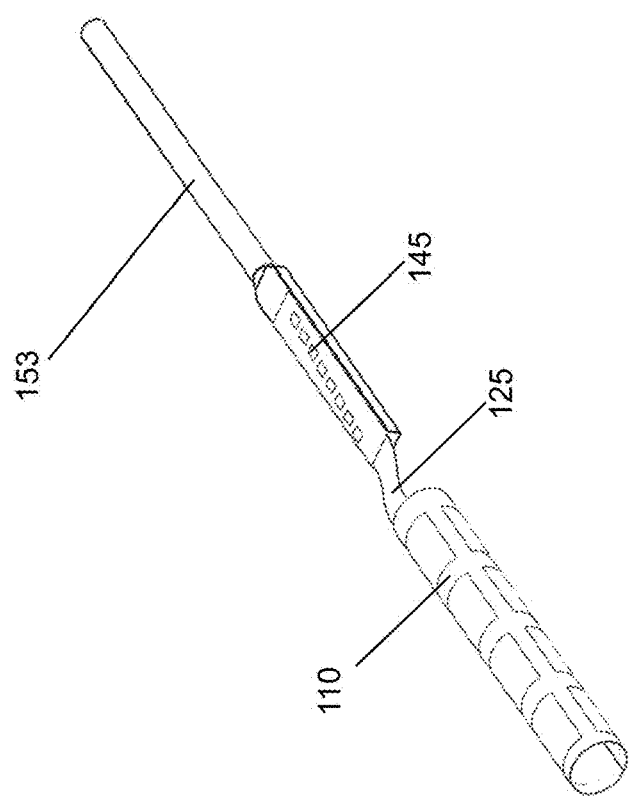
FIG. 7A
FIG. 7B

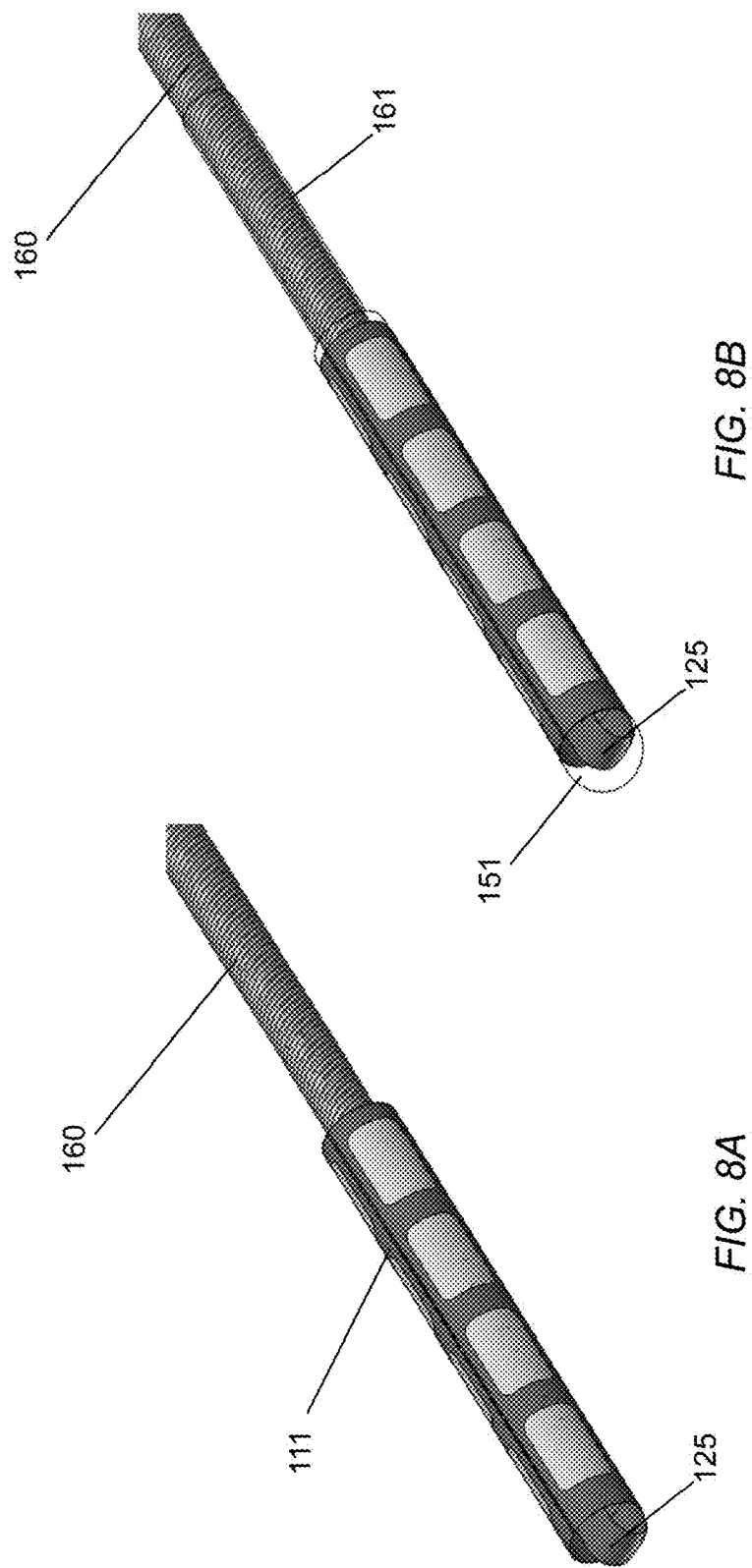

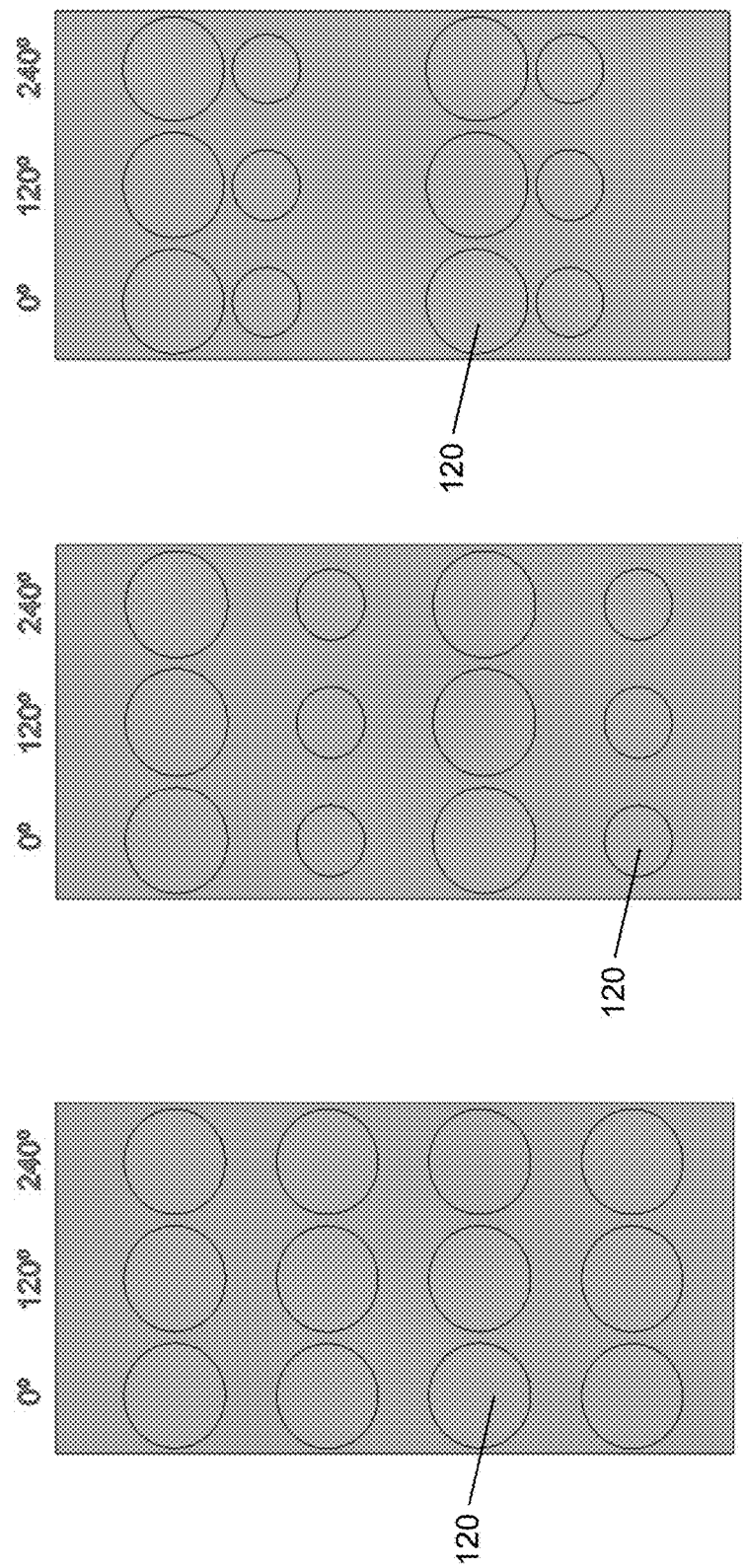

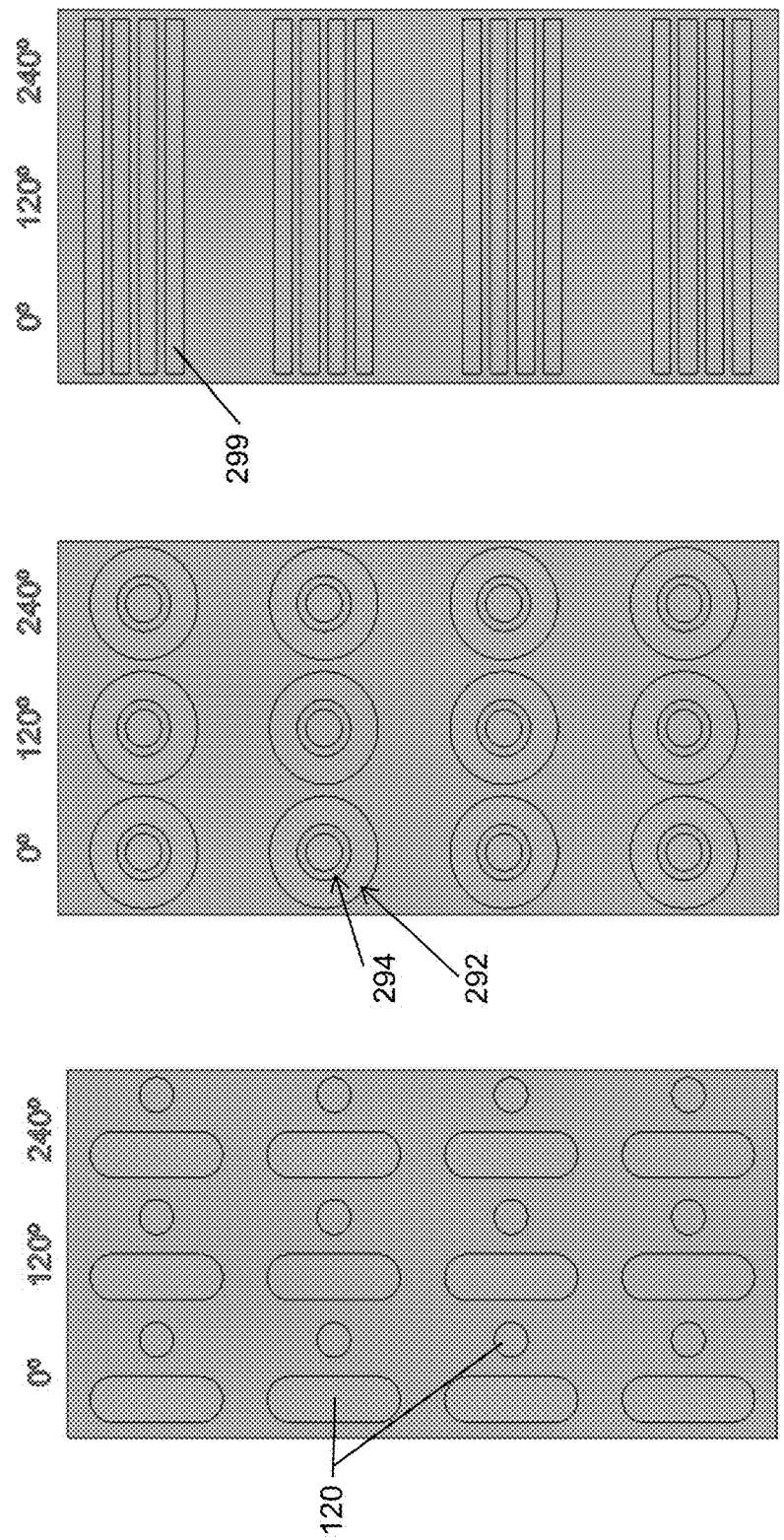

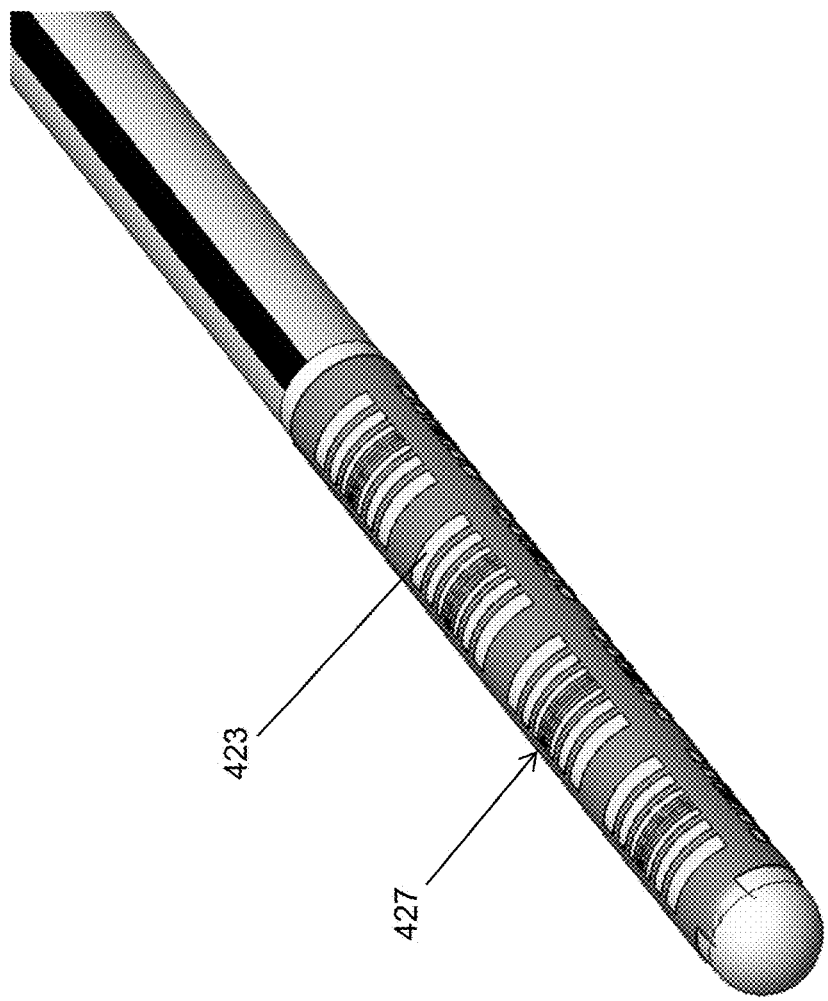

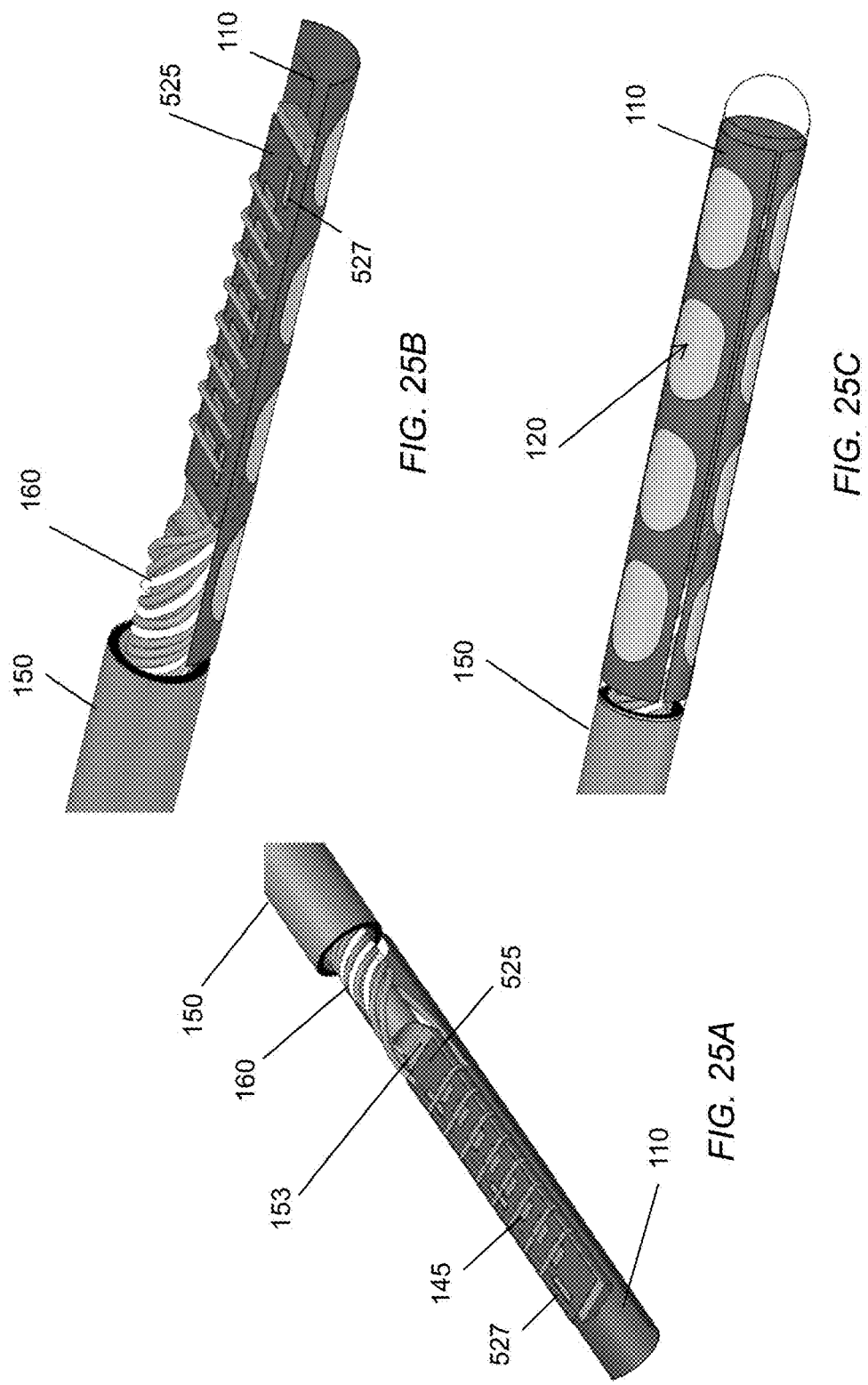

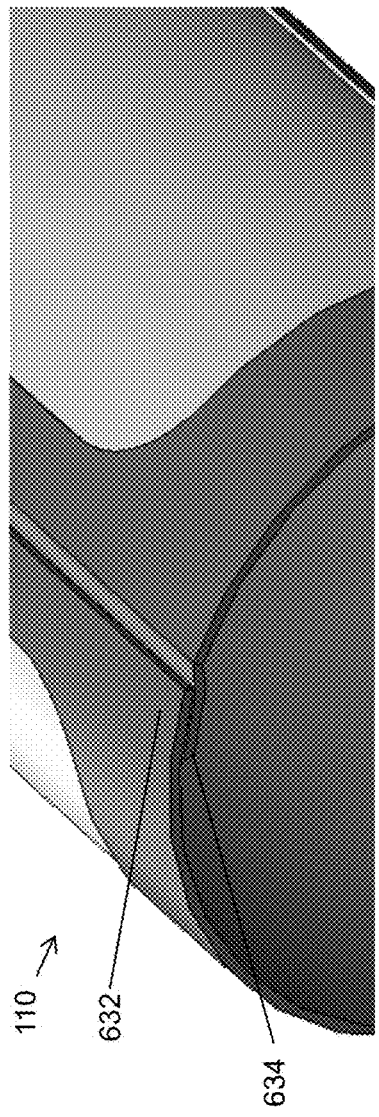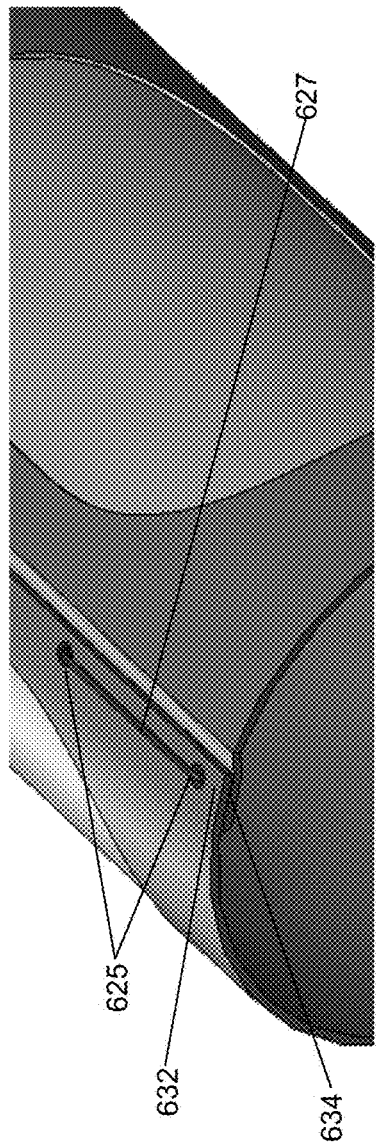

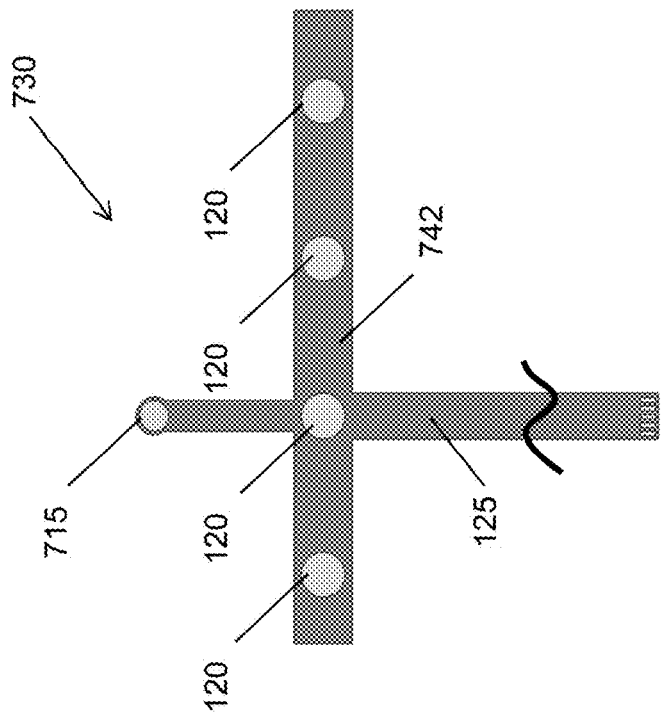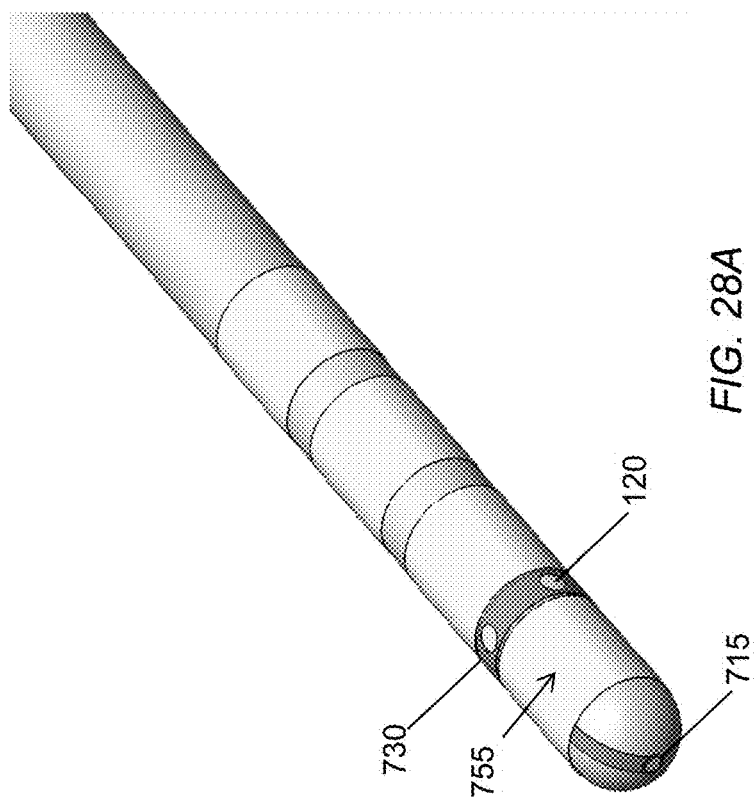

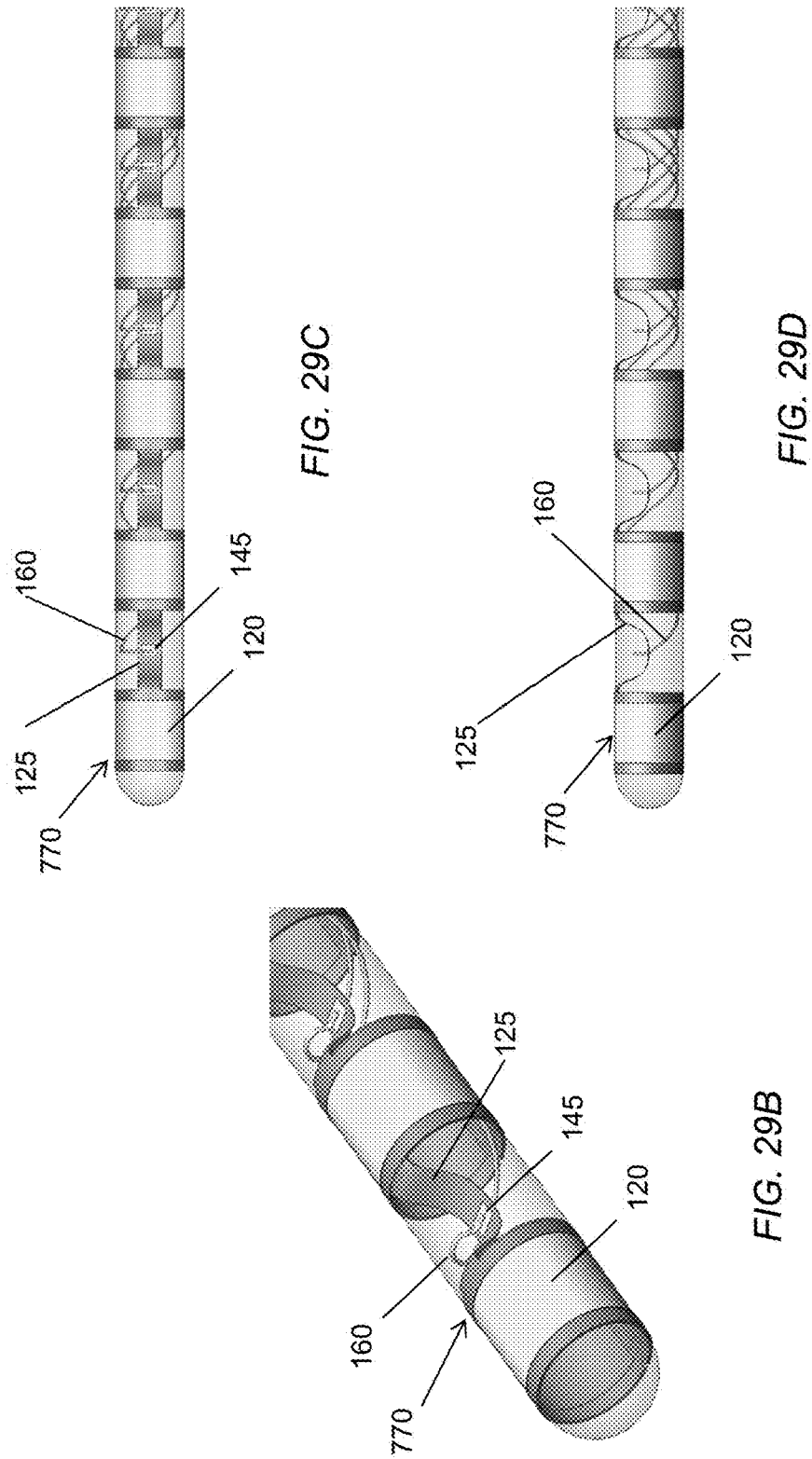

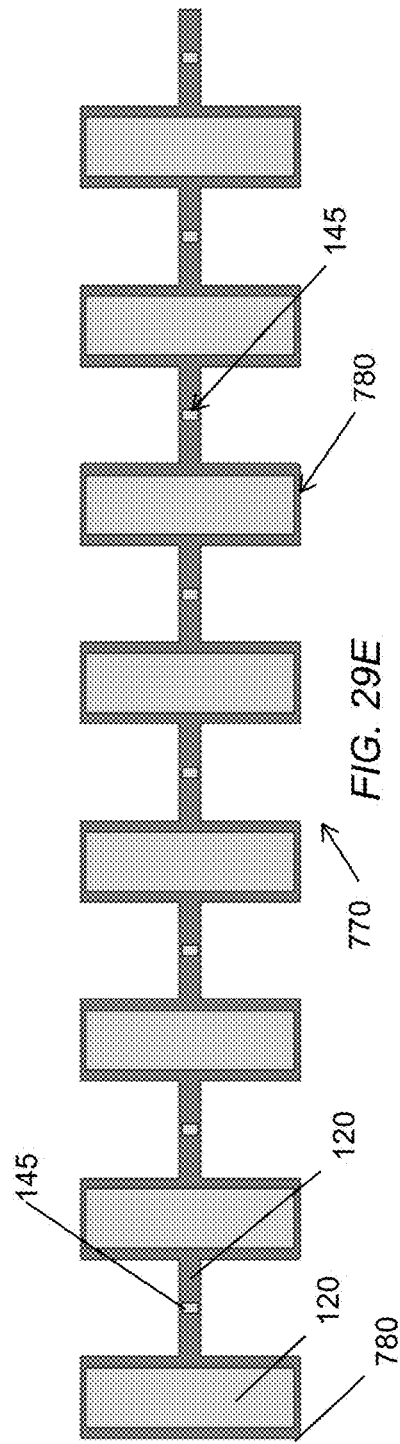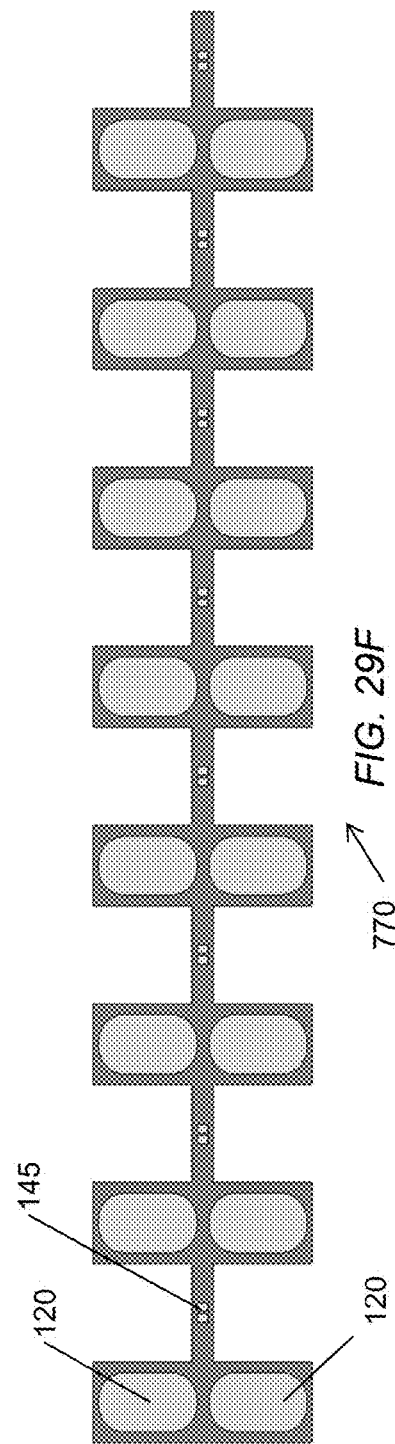

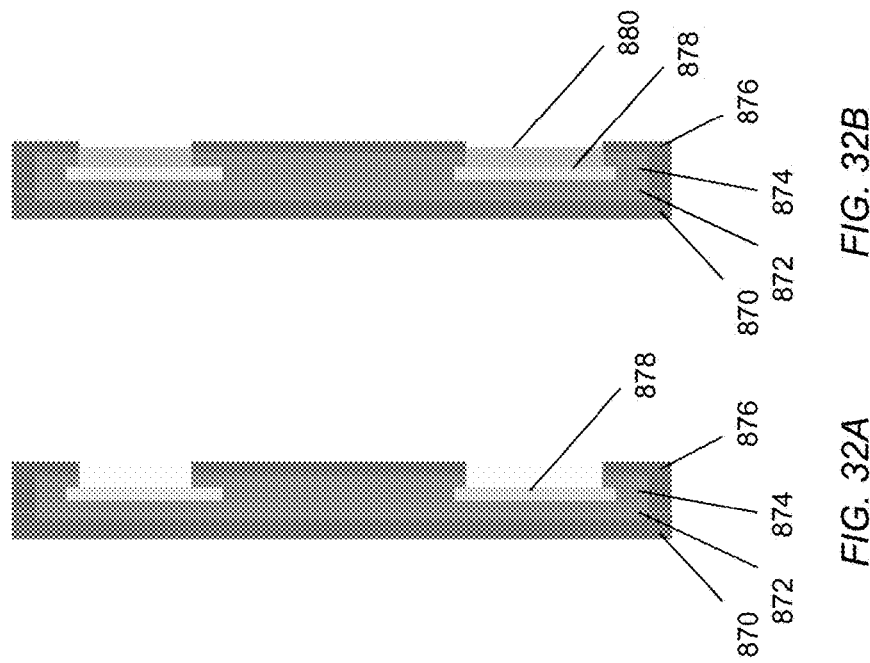
FIG. 32A
FIG. 32B
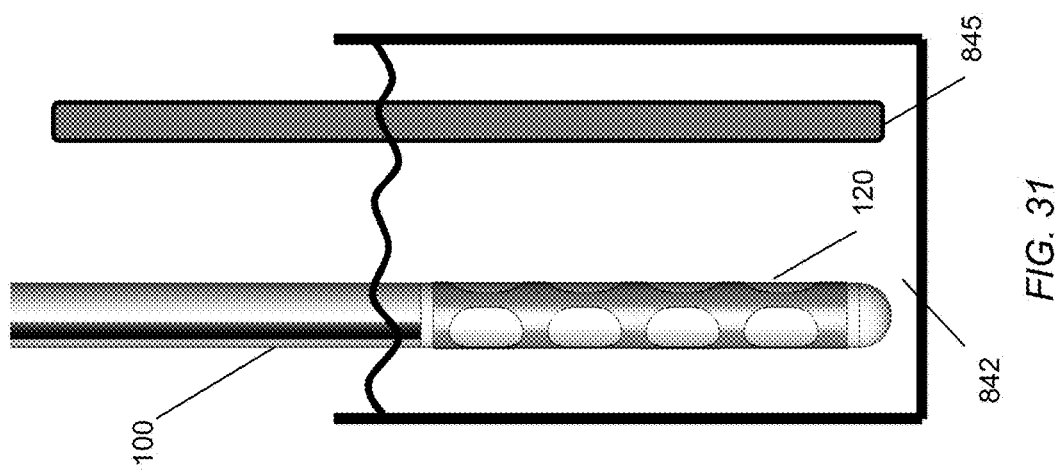
FIG. 31

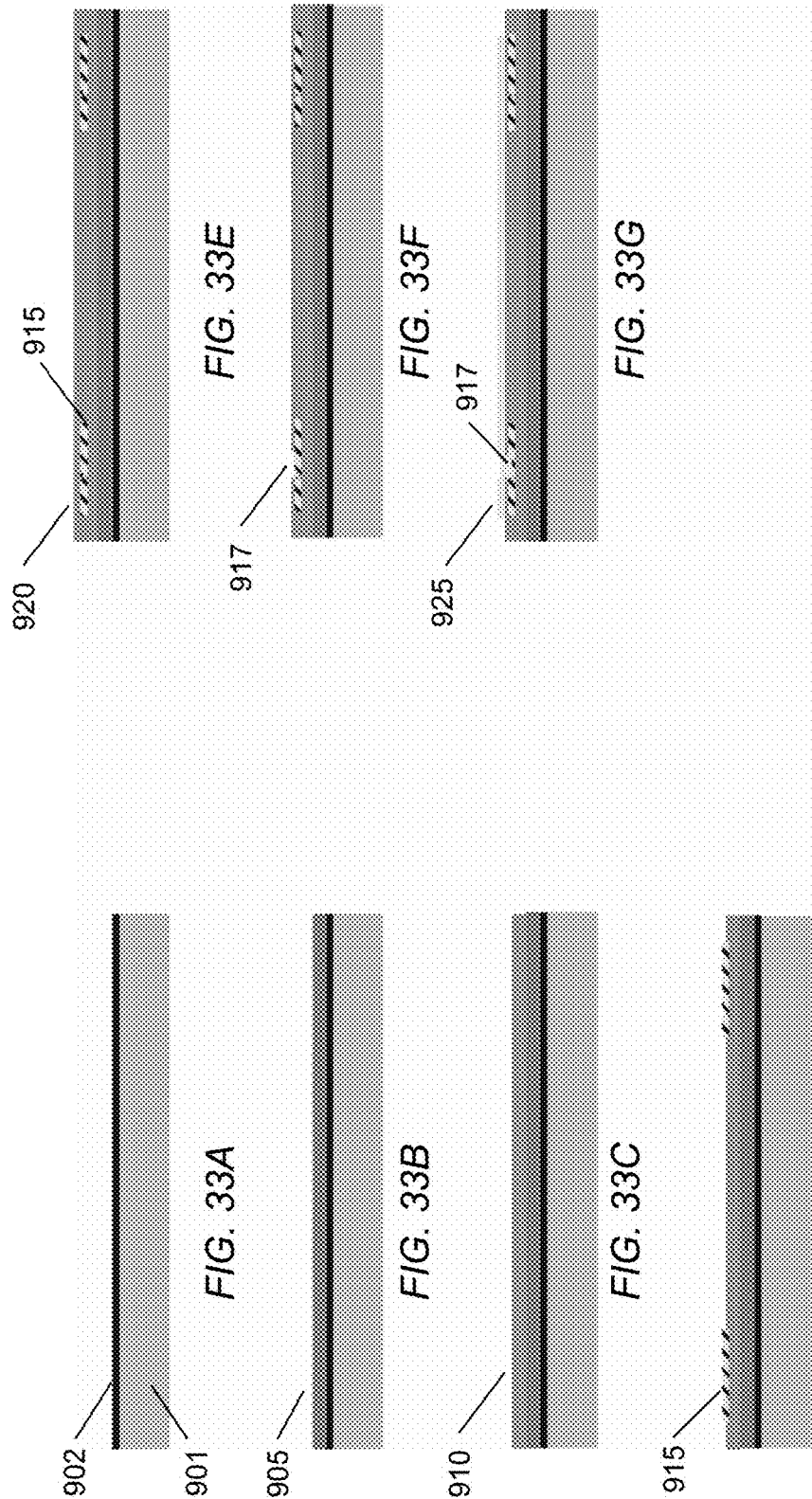

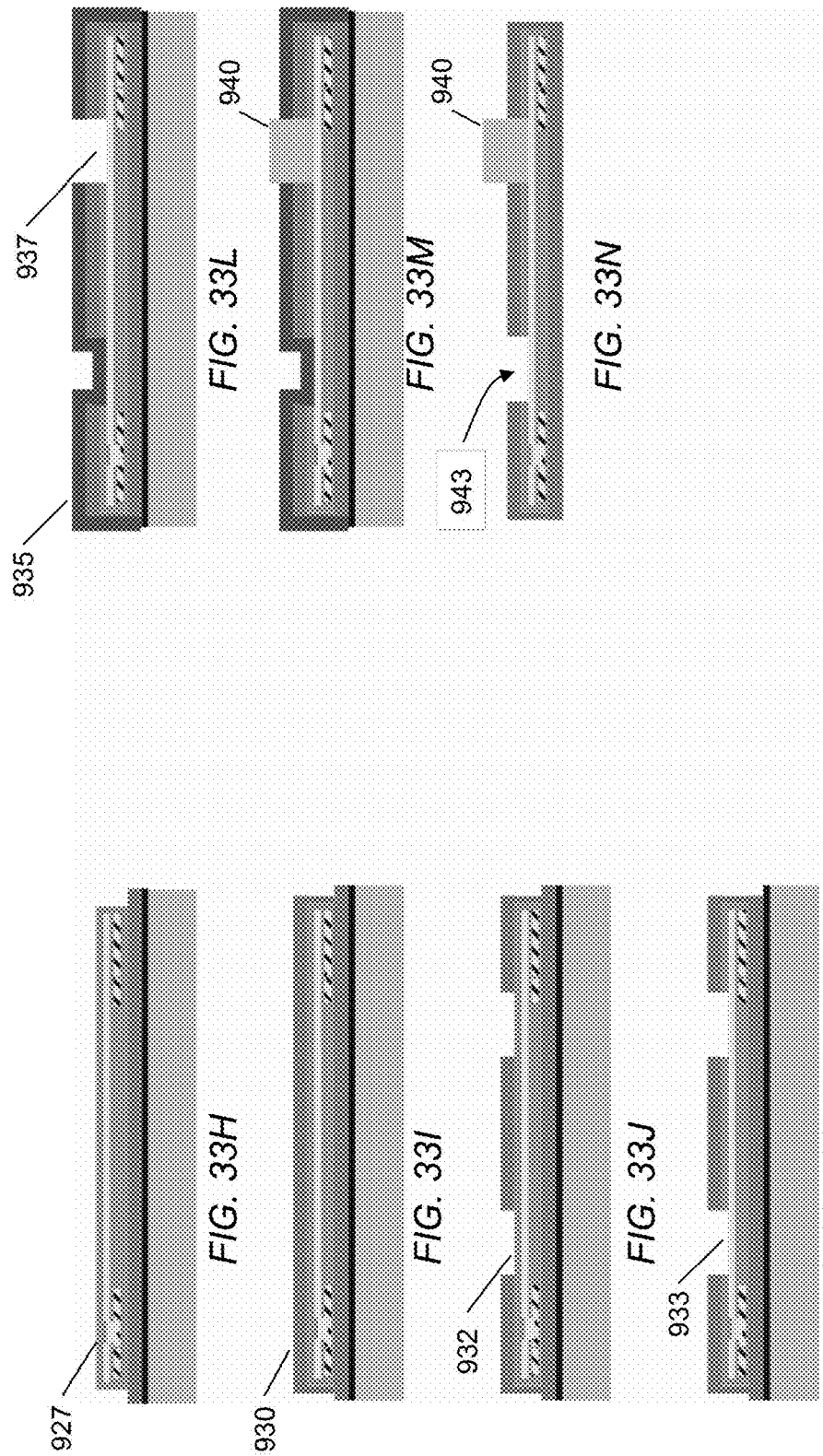

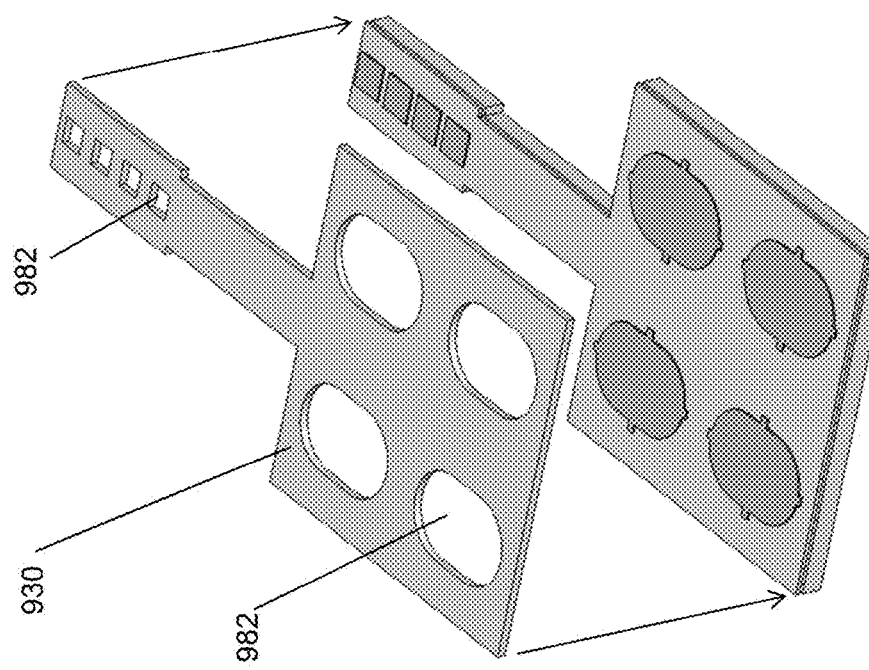
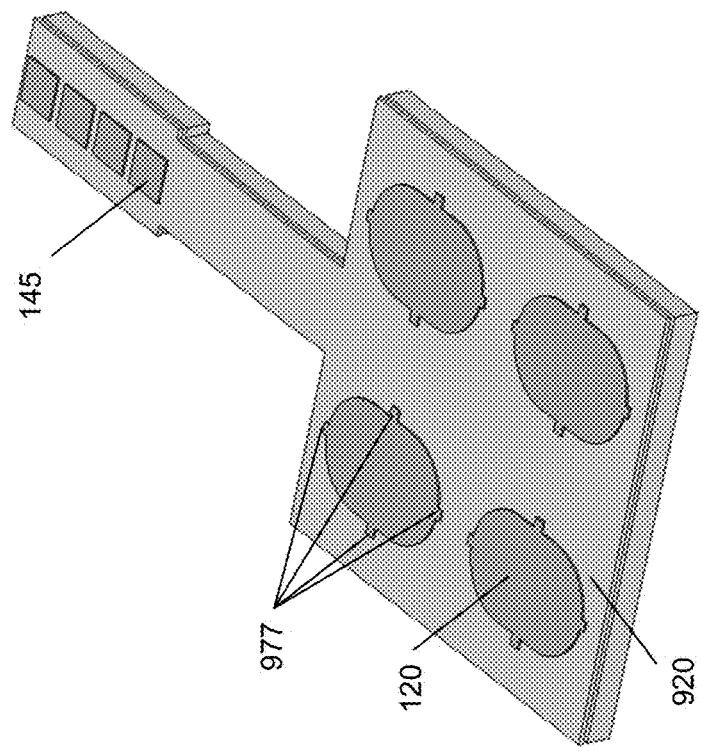

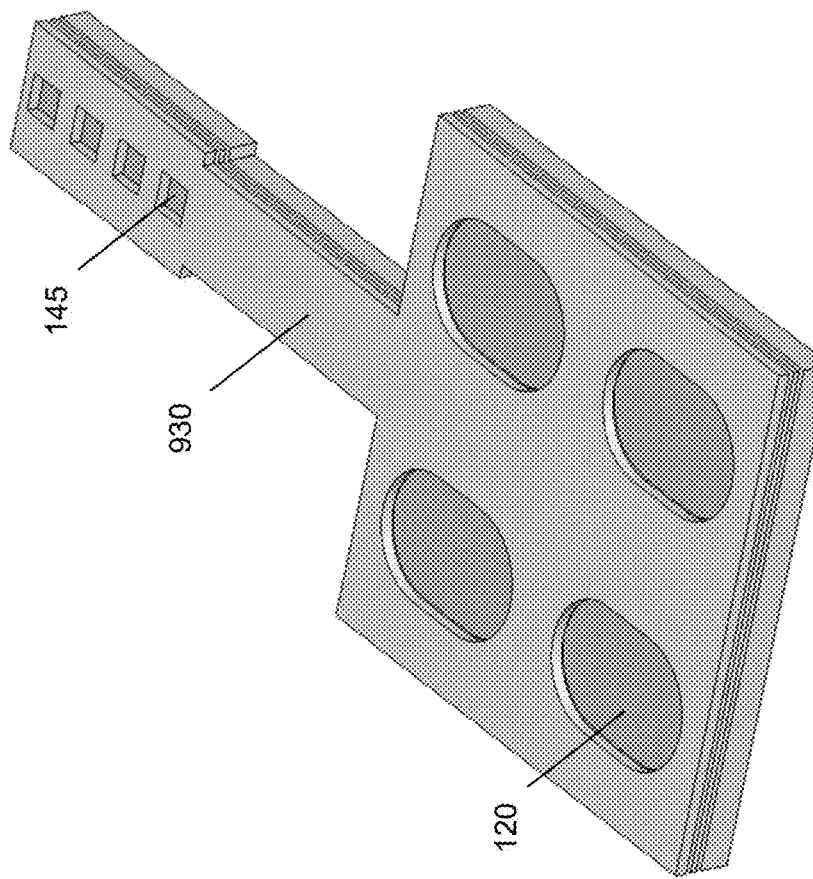

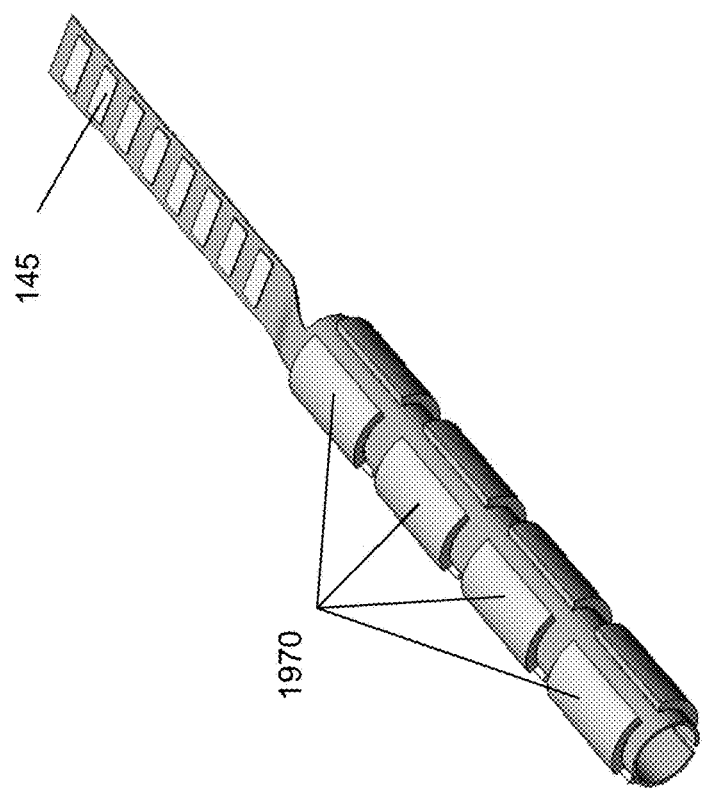
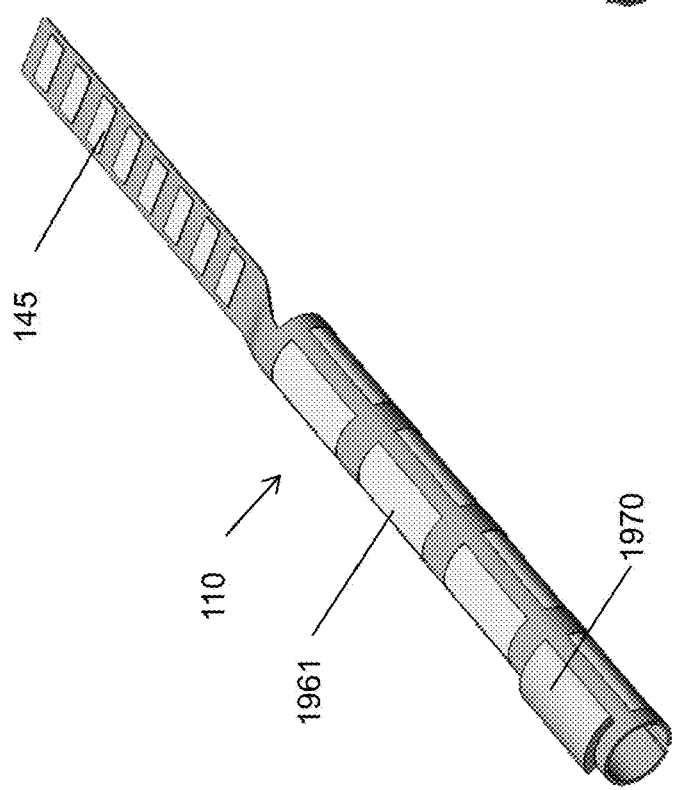
FIG. 38A
FIG. 38B

DEEP BRAIN STIMULATION LEAD

CROSS-REFERENCE TO RELATED APPLICATIONS

This application claims priority as a continuation application under 35 U.S.C. § 120 of U.S. patent application Ser. No. 14/470,423 filed on Aug. 27, 2014, now U.S. Pat. No. 9,474,894, and titled "DEEP BRAIN STIMULATION LEADS," which is herein incorporated by reference in its entirety.

BACKGROUND OF THE DISCLOSURE

Deep brain stimulation (DBS) is a neurostimulation therapy which involves electrical stimulation systems that stimulate the human brain and body. DBS can be used to treat a number of neurological disorders. Typically DBS involves electrically stimulating a target area of the brain.

SUMMARY OF THE DISCLOSURE

According to one aspect of the disclosure, a neurological lead includes a planar formed, cylindrical film that defines a lumen. The planar formed, cylindrical film includes a distal end, a proximal end, and a plurality of electrodes. The planar formed, cylindrical film can also include a ribbon cable extending from the distal end of the planar formed, cylindrical film into the lumen. The film can include a plurality of layers that can include a first polymeric layer, a first silicon based barrier layer at least partially disposed over the first polymeric layer, and a first metal layer at least partially disposed over the first silicon based barrier layer. Other layers can include a second silicon based barrier layer at least partially disposed over the first metal layer or the first silicon based barrier layer. The second silicon based barrier layer can define a first plurality of through-holes. Another layer can be a second polymeric layer that is at least partially disposed over the second silicon based barrier layer. The second polymeric layer can define a second plurality of through holes. The first plurality of through-holes is substantially aligned with the second plurality of through holes to define each of the plurality of electrodes. The film can also include a second metal layer disposed on the first metal layer.

In some implementations, the first metal layer can form the plurality of electrodes and a plurality of traces. The first metal layer can also form a plurality of contact pads disposed on the ribbon cable. Each of the plurality of contact pads are electrically coupled with at least one of the plurality of electrodes by a trace formed in the first metal layer. The second metal layer can include gold and the first metal layer can include one of platinum and titanium.

The first and second silicon based barrier layers can include at least one of Silicon Nitride, Silicon Oxide, Silicon Carbide, Polysilicon, Amorphous Silicon, Titanium Dioxide, and Titanium III Oxide. A thickness of the first and second silicon based barrier layers can be between about 100 nm and about 2 µm thick.

According to another aspect of the disclosure, a method of forming a neurological lead can include forming a planar film that includes a plurality of electrodes and a ribbon cable extending from a distal end thereof. Forming the film can include depositing a first silicon based barrier layer at least partially over a first polymeric layer and depositing a first metal layer at least partially over the first silicon based barrier layer. The method can also include depositing a second silicon based barrier layer partially over the first metal layer and the first silicon based barrier layer, and then depositing a second polymeric layer at least partially over the second silicon based barrier layer. Forming the film can also include depositing a second metal layer on the first metal layer. The method to form the lead can also include heating the formed planar film and molding the heated planar film into a cylinder, which defines a lumen. The method can also include extending the ribbon cable into the lumen defined by the cylinder.

In some implementations, the method also includes forming the plurality of electrodes and contact pads in the first metal layer. A plurality of traces can electrically couple each of the plurality of contact pads to at least one of the plurality of electrodes. The method can also include depositing the second metal layer on the plurality of contact pads. Each of the plurality of electrodes can be defined by etching a plurality of through holes in the second silicon based barrier layer and the second polymeric layer. The first and second silicon based barrier layers can include at least one of silicon nitride, silicon oxide, silicon carbide, polysilicon, amorphous silicon, titanium dioxide, and titanium III oxide.

According to another aspect of the disclosure a neurological lead can include a planar formed, cylindrical film defining a lumen. The planar formed, cylindrical film can include a distal end and a proximal end. The planar formed, cylindrical film may also include a plurality of electrodes disposed on an outer surface of the formed cylinder and a ribbon cable extending from the distal end of the planar formed, cylindrical film. The ribbon cable can extend into the lumen toward the proximal end of the planar formed, cylindrical film. The lumen of the planar formed, cylindrical film can be filled with an encapsulating polymer, and a tube body can be coupled with the proximal end of the planar formed, cylindrical film.

The lead can also include a plurality of contact pads disposed on the ribbon cable. Each of the plurality of contact pads can be electrically coupled to at least one of the plurality of electrodes. The lead can also include a gold layer disposed on each of the plurality of contact pads. The gold layer can be between about 5 µm and about 50 µm thick. The lead can also include a peripheral trace partially surrounding each of the plurality of electrodes and coupled with each of the plurality of electrodes at two or more locations.

In some implementations, the lead can include one or more orientation marks that are aligned with a directional electrode or the ribbon cable. The one or more orientation marks can be radiopaque.

In some implementations, the at least one of the plurality of electrodes includes a mesh configuration. One of the plurality of electrodes can include rounded corners.

According to another aspect of the disclosure, a method of manufacturing a neurological lead can include providing a planar film comprising a distal end, a proximal end, a plurality of electrodes, and a ribbon cable extending from the distal end of the planar film. The method can include forming the planar film into a cylinder that defines a lumen. The ribbon cable can be extended into the lumen defined by the cylinder, and then the lumen is filled with an encapsulating polymer.

The method can also include heating the planar film. In some implementations, the proximal end of the planar film is coupled with a catheter. The ribbon cable can be coupled with the stylet in some implementations. The method can also include disposing a radiopaque dye on the planar film.

BRIEF DESCRIPTION OF THE DRAWINGS

The figures described herein are for illustration purposes. In some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings. The systems and methods may be better understood from the following illustrative description with reference to the following drawings in which:

FIGS. 5A-5M illustrate an example method for manufacturing the MEMS film.

FIGS. 6A-6B illustrate the MEMS film being molded into a cylinder.

FIG. 7A illustrates the formed MEMS film coupled to a stylet.

FIG. 7B illustrates the lead wires coupling with the ribbon cable of the MEMS film.

FIGS. 8A and 8B illustrates the extension of the ribbon cable into the lumen of the molded MEMS film.

FIGS. 11A-11I illustrate MEMS film configurations that include different electrode designs.

FIG. 23A illustrates a MEMS film with gradient electrodes turned perpendicular to the length of the stimulation lead.

FIGS. 25A-25C illustrate a MEMS film without a ribbon cable coupled to a style and coupled with a lead body.

FIGS. 26A-26H illustrate methods for maintaining the cylindrical shape of the planar formed, cylindrical MEMS film.

FIG. 28A illustrates a MEMS film coupled to an existing stimulation lead.

FIG. 28B illustrates the MEMS film of FIG. 28A in a planar configuration.

FIGS. 29A-29D illustrate the distal end of a stimulation lead configured with electrodes distributed longitudinally along the axis of the stimulation lead.

FIGS. 29E and 29F illustrate the MEMS film in a planar configuration before being disposed on the external tube.

FIG. 31 illustrates the process of electro-galvanically thickening electrodes.

FIG. 32A illustrates a cross section of a stimulation lead with no platinum growth.

FIG. 32B illustrates a cross section of a stimulation lead with platinum growth.

FIGS. 33A-33N illustrate the method of manufacturing a MEMS film with a second, encapsulated metal layer.

FIGS. 34A-34E illustrate an example of a MEMS film with two metal layers.

FIGS. 38A and 38B illustrate the coupling of the contacts with the MEMS film.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Figure 1:
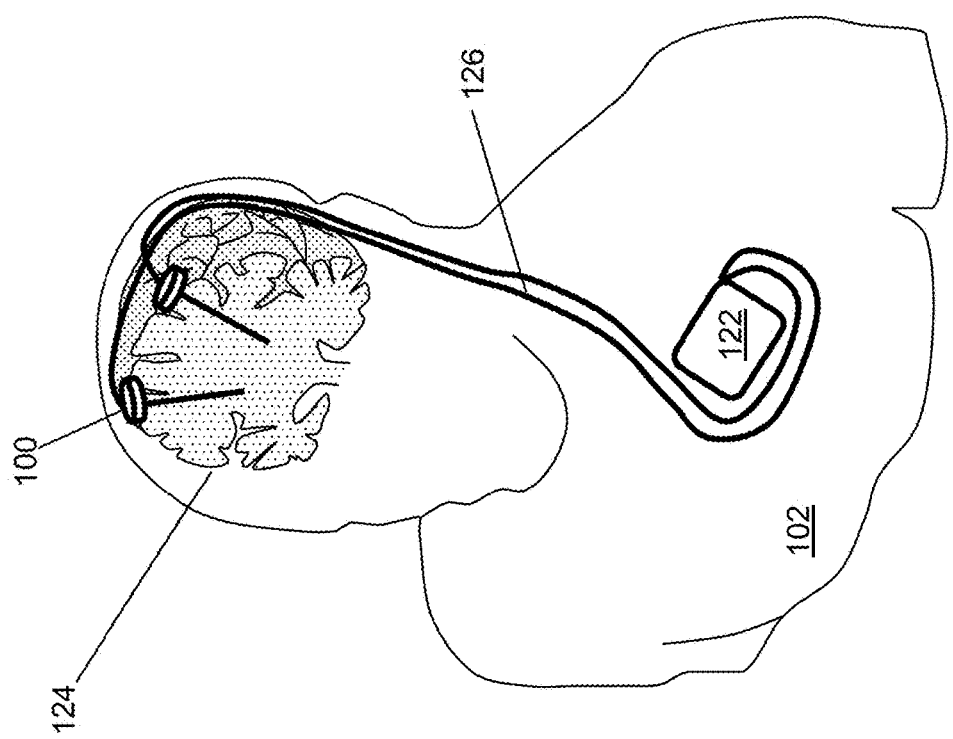
FIG. 1 illustrates an example system for performing neurostimulation.

FIG. 1 illustrates an example system 50 for performing neurostimulation. The system 50 includes a stimulation lead 100 implanted into the brain 124 of a patient 102. The stimulation lead 100 is coupled with a stimulator 122 through cables 126. The stimulator 122 generates therapeutic, electrical stimulations that can be delivered to the patient's brain 124 by the stimulation lead 100.

Figure 2:
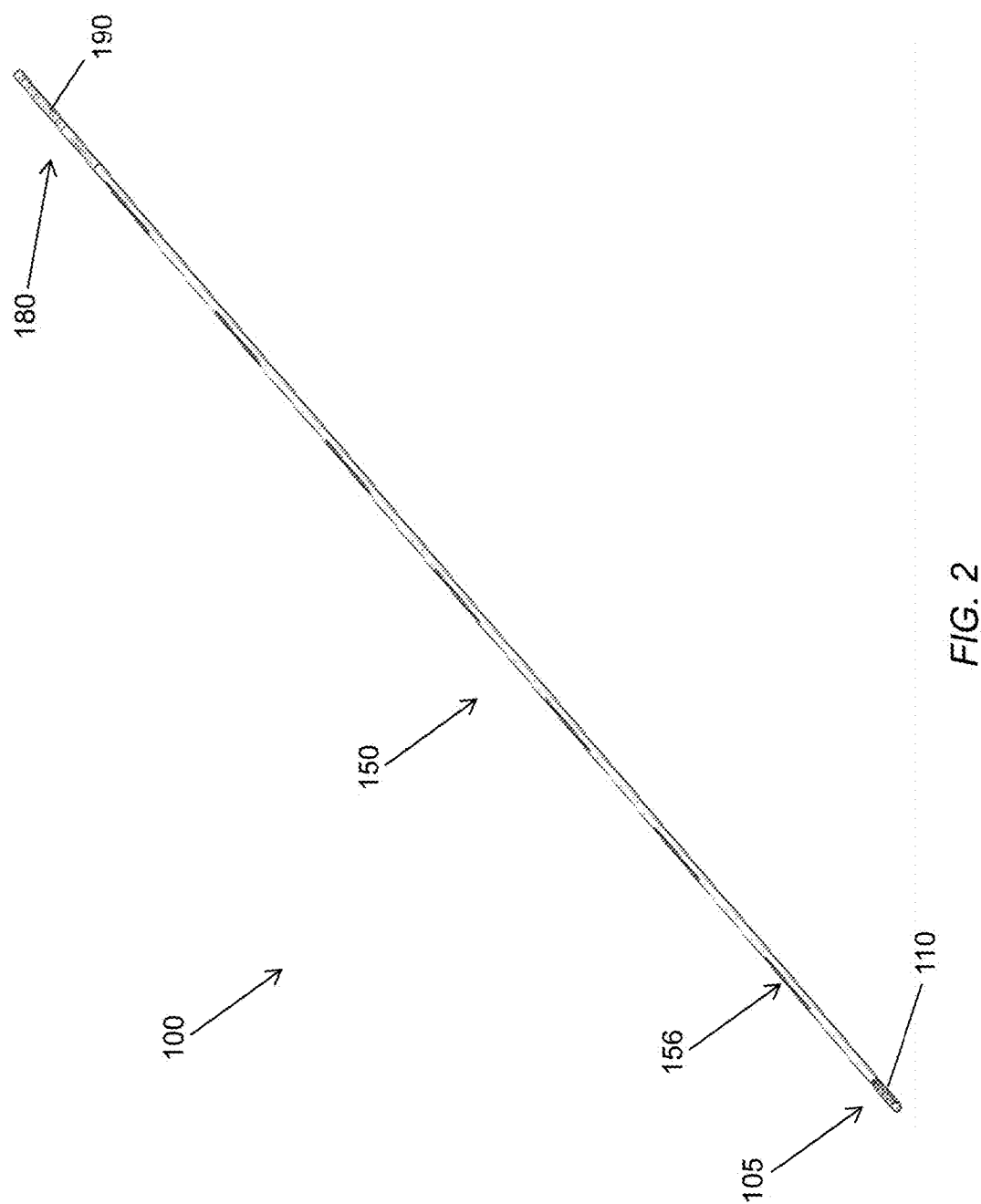
FIG. 2 illustrates an example stimulation lead for use in neurostimulation.

FIG. 2 illustrates an example stimulation lead 100. The stimulation lead 100 includes a body 150. The body 150 may also be referred to as a tube body, tube, or catheter. The body 150 includes a number of orientation marks 156. At a distal end 105, the stimulation lead 100 includes a MEMS film 110. At a proximal end 180, the stimulation lead 100 includes a plurality of contacts 190.

At the proximal end 180 of the stimulation lead 100, the stimulation lead 100 includes one or more contacts 190. The contacts 190 can be used to establish an electrical connection between the electrodes of the MEMS film 110 and the implanted stimulator 122. For example, each of the contacts 190 can be coupled with one or more electrodes of the MEMS film 110. The stimulator 122 may then couple with the contacts 190 through a plurality of cables 126 to stimulate tissue or record physiological signals.

Figure 3A:
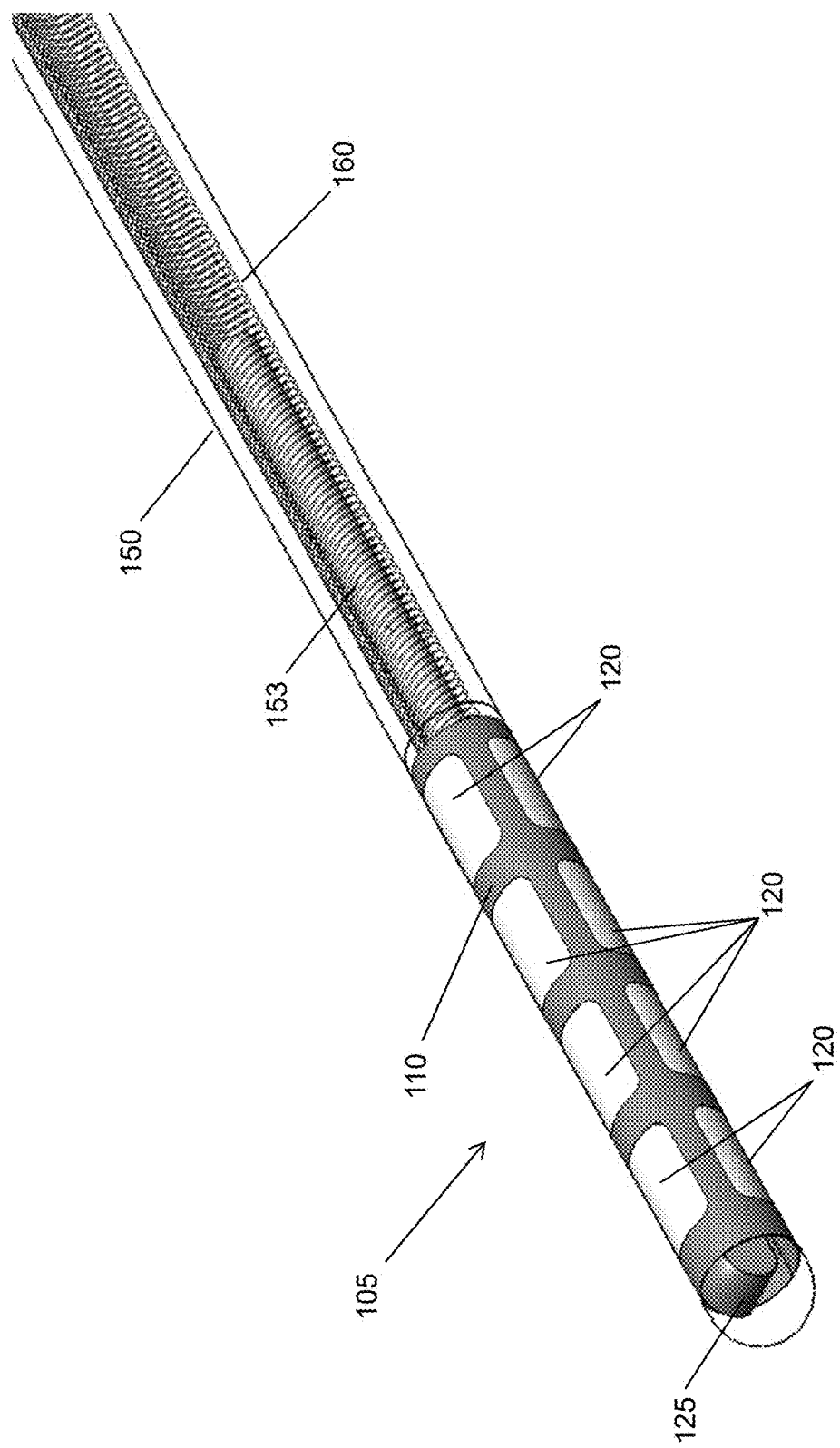
FIGS. 3A and 3B illustrate the distal end and example stimulation lead in greater detail.

The distal end 105 of the stimulation lead 100 can include a MEMS film 110. FIG. 3A illustrates the distal end 105 and example MEMS film 110 in greater detail. The MEMS film 110 can be wrapped or assembled around the distal end 105 of the body 150 or formed into a semi-rigid cylinder that is coupled to the end of the body 150. The MEMS film 110 includes a plurality of electrodes 120. The MEMS film 110 can also include a ribbon cable 125 that wraps over the most distal end of the MEMS film 110 and extends into a lumen defined by the MEMS film 110. As described below, the ribbon cable 125 is coupled with one or more lead wires 160. A portion of the length of the lead wires 160 are wrapped around a stylet 153.

The MEMS film 110 can include one or more electrodes 120. As illustrated, the MEMS film 110 includes 12 electrodes. In some implementations, the MEMS film 110 can include between about 6 and about 64 electrodes, between about 8 and about 32, between about 8 and about 24, or between about 8 and about 12 electrodes. The electrodes 120 can be configured as directional or omnidirectional electrodes. Omnidirectional electrodes may wrap substantially around (e.g., at least 80%, or at least 90%) the circumference MEMS film 110 when the MEMS film 110 is formed into a cylinder, and the directional electrodes may wrap only around a portion of the circumference (e.g., less than 80%) the planar formed, cylindrical MEMS film 110. One or more directional electrodes can electrically couple to form an omnidirectional electrode. For example, the three distal most electrodes 120 may be electrically coupled together to form an omnidirectional electrode at the tip of the stimulation lead 100. In some implementations, the MEMS film 110 can include a plurality of omnidirectional electrodes and a plurality of directional electrodes. For example, the electrodes 120 may be configured as two omnidirectional electrodes and six directional electrodes.

Electrical traces can couple each of the electrodes 120 with one or more of the lead wires 160. For example, the traces may run under an insulative layer of the MEMS film 110 to the ribbon cable 125, where the traces terminate and are coupled with the one or more lead wires 160. In some implementations, the stimulation lead 100 includes one lead wire 160 for each of the electrodes 120. In other implementations, the stimulation lead 100 includes fewer lead wires 160 than electrodes 120 because one or more of the lead wires 160 are electrically coupled with more than one of the electrodes 120. For example, when the MEMS film 110 includes two omnidirectional electrodes and six directional electrodes, the stimulation lead 100 may include eight lead wires 160. The lead wires 160 can run along the length of the body 150 toward the proximal end 180 of the body 150. The lead wires 160 may traverse the length of the body 150 in the lumen of the body 150. At the proximal end 180 of the MEMS film 110, the lead wires 160 may be electrically coupled with the contacts 190.

Figure 3B:
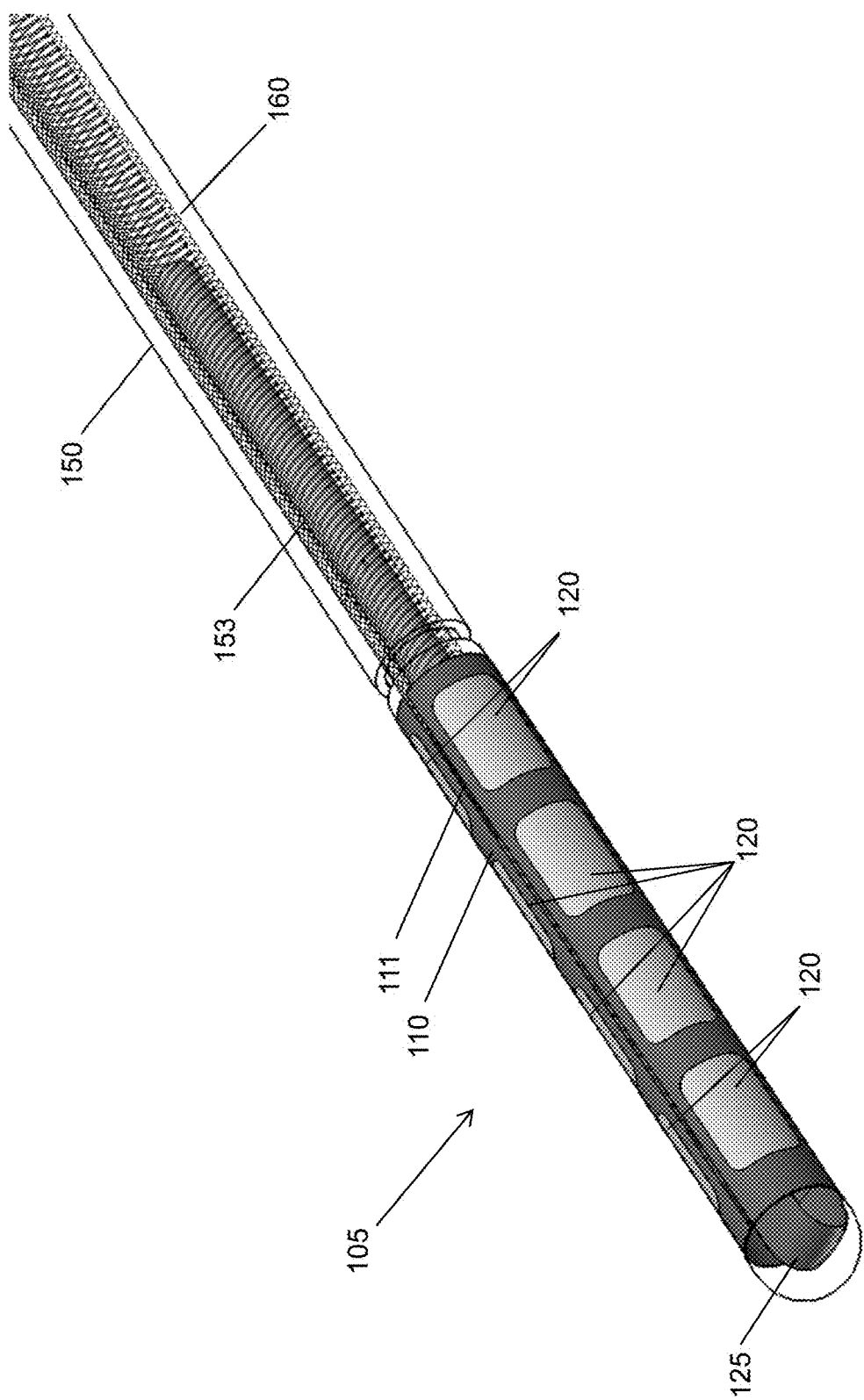

FIG. 3B illustrates the underside of the distal end 105 of the stimulation lead 100. In some implementations, the MEMS film 110 can be initially formed as a planar film that is formed into a cylinder. This method of forming the MEMS film 110 can create a connecting seam 111.

The MEMS film can include a plurality of layers. In some implementations, the MEMS film includes five layers. The five layers can include a first polymeric layer and a first silicon based barrier layer that is at least partially deposited (or otherwise disposed) over the first polymeric layer. The MEMS film 110 can also include a first metal layer that is at least partially deposited (or otherwise disposed) over the first silicon based barrier layer. Other layers can include a second silicon based barrier layer at least partially deposited (or otherwise disposed) over the first metal layer and the first silicon based barrier layer. The second silicon based barrier layer can define a first plurality of through-holes over portions of the first metal layer. Another layer of the MEMS film 110 can be a second polymeric layer that is at least partially deposited (or otherwise disposed) over the second silicon based barrier layer. The second polymeric layer can also define a plurality of through holes. The plurality of through-holes of the second silicon based barrier layer and the second polymeric layer are substantially aligned to define each of the plurality of electrodes 120 and contact pads 145 of the MEMS film 110.

Figure 4:
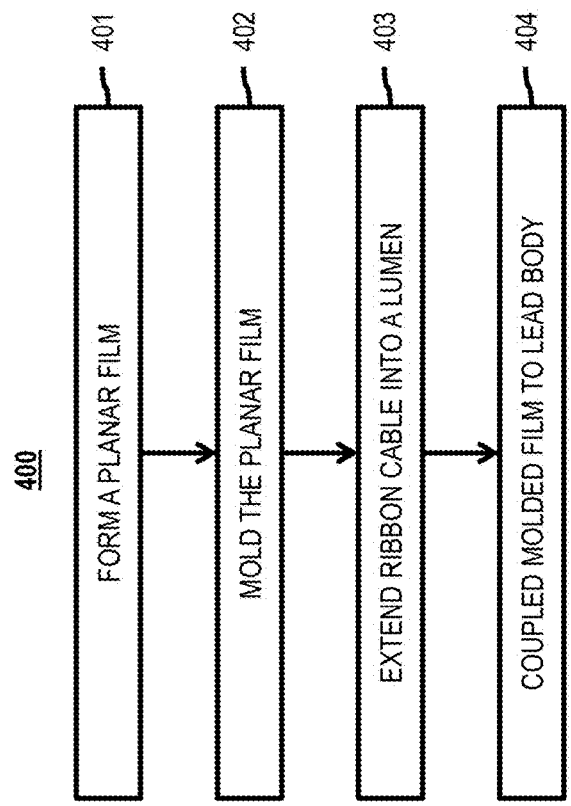
FIG. 4 illustrates a flow chart of an example method for manufacturing a stimulation lead.

FIG. 4 illustrates a flow chart of an example method 400 for manufacturing a stimulation lead. The method 400 can include forming a planar MEMS film (step 401). The planar MEMS film can then be molded into a cylinder (step 402). A ribbon cable of the MEMS film may then be extended into a lumen of the molded cylinder (step 403). The molded MEMS film may then be coupled with a lead body (step 404).

As set forth above, the method 400 can begin with the forming of a planar MEMS film (step 401). The planar MEMS film may be a planar version of the MEMS film 110. The planar MEMS film can be referred to generically as the MEMS film 110. In some implementations, the MEMS film 110 includes a plurality of layers. The MEMS film 110 can include one or more polymeric layers, one or more silicon based barrier layers, and one or more metal layers. For example, the MEMS film 110 can include a first polymeric layer, a first silicon based barrier layer, a first metal layer, a second silicon based barrier layer, a second polymeric layer, and a second metal layer. The silicon based barrier layers can improve adhesion of the layers, improve scratch resistance of the metal layers, and impede the flow of ions and humidity between the layers. Ions and humidity can traverse a polymeric layer and cause electrical short circuits in the metal layer of a MEMS device. The silicon based barrier layers can prevent or reduce the flow of ions and the introduction of humidity into or between the layers. Accordingly, the reduction of ion flow and humidity between the layers by the silicon based barrier layers can improve the performance and durability of the MEMS film 110.

FIGS. 5A-5M illustrate an example method for manufacturing the MEMS film 110. More particularly, FIGS. 5A-5M illustrate a cross-sectional view of an example thin-film micro-fabrication method for fabricating the MEMS film 110. The MEMS film 110 can be fabricated using a plurality of techniques and the below describe method illustrates one possible method for fabricating the MEMS film 110. The fabrication procedure can include a series of procedural steps in which various layers are deposited or removed (e.g., etched) to achieve a final form. The cross sections in FIG. 5A through FIG. 5M demonstrate the process steps to build a MEMS film 110.

In a first step illustrated in FIG. 5A, a carrier substrate 201 is provided, such as a wafer composed of a crystalline material, such as silicon, or an amorphous material, such as a thermal shock resistant borosilicate glass or other suitable smooth supportive material. A first layer 202, which can include one or more sub-layers, is applied to a surface of the wafer 201. One of the sub-layers can be a sacrificial layer deposited on the wafer 201, which is removed in a subsequent electrochemical etching step. In some implementations, the sacrificial sub-layer is preceded by another sub-layer, referred to as an underlayer, which can serve to form the electrochemical cell required to etch the sacrificial layer. The sacrificial sub-layer can be aluminum, or an alloy of aluminum such as AlSi, which has a smaller granularity, whereas the underlayer can be a TiW alloy such as Chrome or similar metal. In some implementations, when the sacrificial sub-layer is not implemented, the removal of the resulting device from the substrate is difficult and could result in damage to the finished device.

Referring to FIG. 5B, the next step in the fabrication process can include depositing a first polymeric layer 205. The first polymeric layer 205 can be deposited upon the sacrificial layer 202 by MEMS processes such as, but not limited to, (i) spin coating a liquid polymer precursor such as Polyimide or Silicone precursor; (ii) depositing a polymer through chemical vapor deposition as is done with parylene-C; or (iii) laminating a polymer sheet onto the wafer. In some embodiments, the polymer layer 205 is heated, or baked, to polymerize. In some implementations, the first polymeric layer 205 includes polyamic-acid dissolved in NMP and spun onto the sacrificial layer 202 in liquid form. The polymeric layer 205 is heated into a imidized polyimide. The polymer in its cured form is between about 5 µm and about 15 µm thick. The polymer layers of the MEMS film can serve as a barrier to water, humidity, and isolate the components of the MEMS film.

FIG. 5C illustrates the deposition of a silicon based barrier layer. The silicon based barrier layer can serve both as a layer to aid the adhesion and durability of subsequent layers. The silicon based barrier layer can also serve as an ionic barrier, and limit ions from reaching the metal layers, which could compromise electrical performance. The silicon based barrier layer can also block humidity from reaching the interlayers and the metal layer, which could create short circuits and compromise electrical isolation.

In some implementations, the silicon based barrier layer is deposited onto the first polymeric layer 205 by vapor deposition techniques such as chemical vapor deposition (CV) and plasma enhanced chemical vapor deposition (PECVD), or by sputtering techniques such as direct current (DC) or RF (Radio Frequency) sputtering. The silicon based barrier layer can include Silicon Nitride, Silicon Oxide, Silicon Carbide, Poly-Silicon, or Amorphous-Silicon. The silicon based barrier layer can also include other non-conductive materials, such as Titanium Dioxide or Titanium (III) Oxide. The final thickness of the silicon based barrier layer can range from about 20 nm to about 2 µm. In some implementations, the silicon based barrier layer is about 400 nm to about 600 nm, which can permit the silicon based barrier layer to be flexible enough to bend during subsequent assembly techniques.

Now referring to FIG. 5D, a metal layer 215 can be deposited over the entire wafer on the surface of the silicon based barrier layer 210. Subsequently, a photoresist layer 217 can be deposited. The photoresist layer 217 can be defined by exposing areas of the photoresist layer 217 to ultra-violet light and developing those areas in a solvent. Thus, the exposed areas of the photoresist layer 217 will be selectively removed and areas of the metal layer 215 will be exposed. The areas of the metal layer 215 covered by the photoresist layer 217 can form the electrodes, traces, and other components of the final product that are within the metal layer.

The metal layer 215 can include a variety of metals such as titanium, platinum, gold, and others metals used in neuromodulation. To improve adhesion of a metal layer 215, the metal layer 215 can be applied in layers. For example, the metal layer 215 can be applied as a first layer, such as titanium, then a middle layer, such as platinum, and finally an upper layer, such as titanium. This tri-layer metal structure can improve adhesion below and above the platinum layer by using the titanium as an adhesion layer to the silicon based barrier layer. The typical thicknesses for the adhesion layer of titanium can be between about 20 nm and about 100 nm or between about 25 nm and about 75 nm. Typical thicknesses for the platinum layer can be between about 200 nm and about 7 µm, between about 400 nm and about 5 µm, between about 400 nm about 3 µm, between about 400 nm and about 1 µm, or between about 400 nm and about 700 nm. In some implementations platinum can be replaced by another, high charge transfer capable material such as iridium oxide.

FIG. 5E illustrates the process after the etching of the metal layer 215. As illustrated, the metal layer 215 can be locally removed in the areas that were not covered by the photoresist 217. In some implementations, etching of the metal layer is performed in a plasma etcher such as a Reactive Ion Etcher. In some implementations, titanium and platinum can be etched with chlorine gas. After the etching process is finished, the photoresist layer 217 can be removed using a solvent.

Another method to deposit and define the metal layer is using the so-called "lift off" technique. In this method the photoresist layer can be deposited onto the silicon based barrier layer 210 first. The photoresist layer can be defined using photolithography. The metal layer 215 can then be deposited through this "lift off" mask, and the remaining photoresist removed in a solvent. In this method the metal layer is transferred onto the silicon based barrier layer without the need of plasma etching and may have some process costs and speed advantages.

Referring next to FIG. 5F, a deposition of a second barrier layer 220 is performed. The second barrier layer can be deposited using the same techniques as the first silicon based barrier layer 210. The second barrier layer 220 can be the same thickness, or a different thickness as the first silicon based barrier layer. In some implementations, the second silicon based barrier layer is optional. The second silicon based barrier layer 220 and the first silicon based barrier layer 210 can substantially surround (e.g., at least 80%) the metal layer 215, rendering it electrically isolated. In order to etch and define the first and second silicon based barrier layer 210 and 220, respectively, a second photoresist layer 227 is deposited and photolithographically defined with clean room techniques.

The two silicon based barrier layers are etched, as illustrated in FIG. 5G. The silicon based barrier layers can be etched using a plasma etch. An example of an etching process would be a reactive ion etching using a tetrafluoromethane gas, (CF4). The second photoresist layer 227 can be removed using a solvent dissolution.

FIG. 5G illustrates an example where the edges of the silicon based barrier layers 210 and 220 are defined, but the etch does not reach the metal layer 215. In some implementations the photolithography can include an opening above the metal layer 215, which would result in exposing the metal layer 215.

FIG. 5H illustrates the application of a second polymer layer 230. The second polymer layer 230 can be the same or a different polymer from the first polymer layer 205, and it can be the same or a different thickness.

FIG. 5I illustrates the deposition of a third photoresist 237, which can form the etching perimeter of the first and second polyimide layers 205 and 230, respectively. In some implementations, prior to the applying the third photoresist 237, a sacrificial layer, such as Silicon Dioxide or Silicon Nitride, is deposited in order to serve as an etch mask for the polyimide etch. For example, a silicon dioxide layer of thickness of about 500 nm can be deposited, which will serve as the etch mask for the process.

FIG. 5J illustrates the result of an oxygen plasma etching of the first and second polyimide layers 205 and 230, respectively. If applied, the silicon dioxide layer can be removed through an additional etch.

FIG. 5K illustrates the deposition of a fourth photoresist layer 247. In some implementations, the fourth photoresist layer 247 does not cover part of the metal layer 215. For example, the opening 232 can be maintained to create a region for a gold layer to grow.

FIG. 5L illustrates the galvanic growth of a thick gold layer 250 into the opening 232. In some implementations, the gold layer 250 is achieved by connecting the metal traces in the wafer to a perimetric metal band that allows an electrical connection between the edge of the wafer and the metal opening 232. When immersed in a galvanic bath and a current applied, the gold will grow on the metal layer 215 using the metal layer 215 as the seed layer for galvanic growth. In some implementations, the gold layer 250 is about 2 μm to about 20 μm thick. The fourth photoresist layer 247 can be removed using a solvent.

FIG. 5M illustrates the removal of the MEMS film from the wafer 201. The removal of the fourth photoresist layer 247 exposes the electrode opening 233. The MEMS film can be removed from the wafer 201 by the removal of the sacrificial layer 202 using electrochemically etching. Removal of the sacrificial layer 202 frees the underside of the MEMS film from the wafer 201. In some implementations, the sacrificial layer 202 is removed by placing the wafer in a saline bath with a high NaCl concentration. A platinum electrode also placed in the bath can be used as a reference, and a voltage can be applied to the aluminum layer with respect to the platinum electrode. The electrochemical cell created by the aluminum and TiW etches the aluminum—separating the MEMS film from the wafer 201.

In some implementations, when the MEMS wafer is completed, and the individual devices have been removed, further process steps can occur before to assemble the wafers into a cylindrical shape.

Referring again to FIG. 4, the method 400 can also include molding the MEMS film 110. In some implementations, the MEMS film 110 is molded into a cylinder shape that defines a lumen. FIGS. 6A-6B illustrate the MEMS film 110 being molded into a cylinder.

FIG. 6A illustrates a planar view of the MEMS Film 110. As illustrated, the MEMS film 110 includes twelve electrodes 120. The electrodes 120 can be generally rectangular in shape with rounded corners. The ribbon cable 125 extends from the distal end of the MEMS film 110. The ribbon cable 125 can include one or more traces that electrically couple the electrodes 120 to the contact pads 145. In some implementations, each of the contact pads 145 are electrically coupled with one or more electrodes 120.

FIG. 6B illustrates the molded MEMS film 110. In some implementations, the MEMS film 110 is heated to and then molded to form a cylinder. The MEMS film 110 can be heated and molded using a thermal reflow method. In some implementations, the MEMS film 110 is heated to about 300° C. when molded. The formed cylinder can have an internal diameter of between about 0.5 mm and about 2 mm, between about 1 mm and about 1.5 mm, or between about 1.3 mm and about 1.5 mm after formed into a cylinder. The cylinder shape of the MEMS film 110 can be formed by inserting the MEMS film 110 into a tube with the same diameter that is required for the final device. The MEMS film 110, within the tube, can be heated to a temperature which causes the polymer insulator to slightly reflow and take the new form of the tube.

The end of the ribbon cable 125 can be coupled to a stylet 153. FIG. 7A illustrates the formed MEMS film 110 coupled to the stylet 153. Coupling the MEMS film 110 to the stylet 153 can render the distal end of the ribbon cable 125 rigid and can simplify later assembly steps. For example, coupling the stylet 153 with the ribbon cable 125 can ease the coupling of the lead wires 160 to the contact pads 145. The stylet 153 can include a metallic material (e.g., stainless steel), a ceramic material, or a polymeric material. In some embodiments, the stylet 153 can be radio-opaque such that the surgeon can visualize the stimulation lead 100 in an x-ray or CT scan during the implantation process to control the final placement of the stimulation lead 100. The stylet 153 can also be used to determine the rotation of the stimulation lead because the stylet 153 is partly planar along its longitudinal axis.

FIG. 7B illustrates the lead wires 160 coupling with the ribbon cable 125 of the MEMS film 110. In some implementations, the lead wires 160 are coiled around the stylet 153. The lead wires 160 can be coupled with the contact pads 145 through laser welding, ultrasonic bonding, crimping, thermocompression bonding, or wire bonding. In some implementations, the lead wires 160 are locally flattened to increase the surface area of the lead wires 160 that comes into contact with the contact pads 145.

Figure 7C:
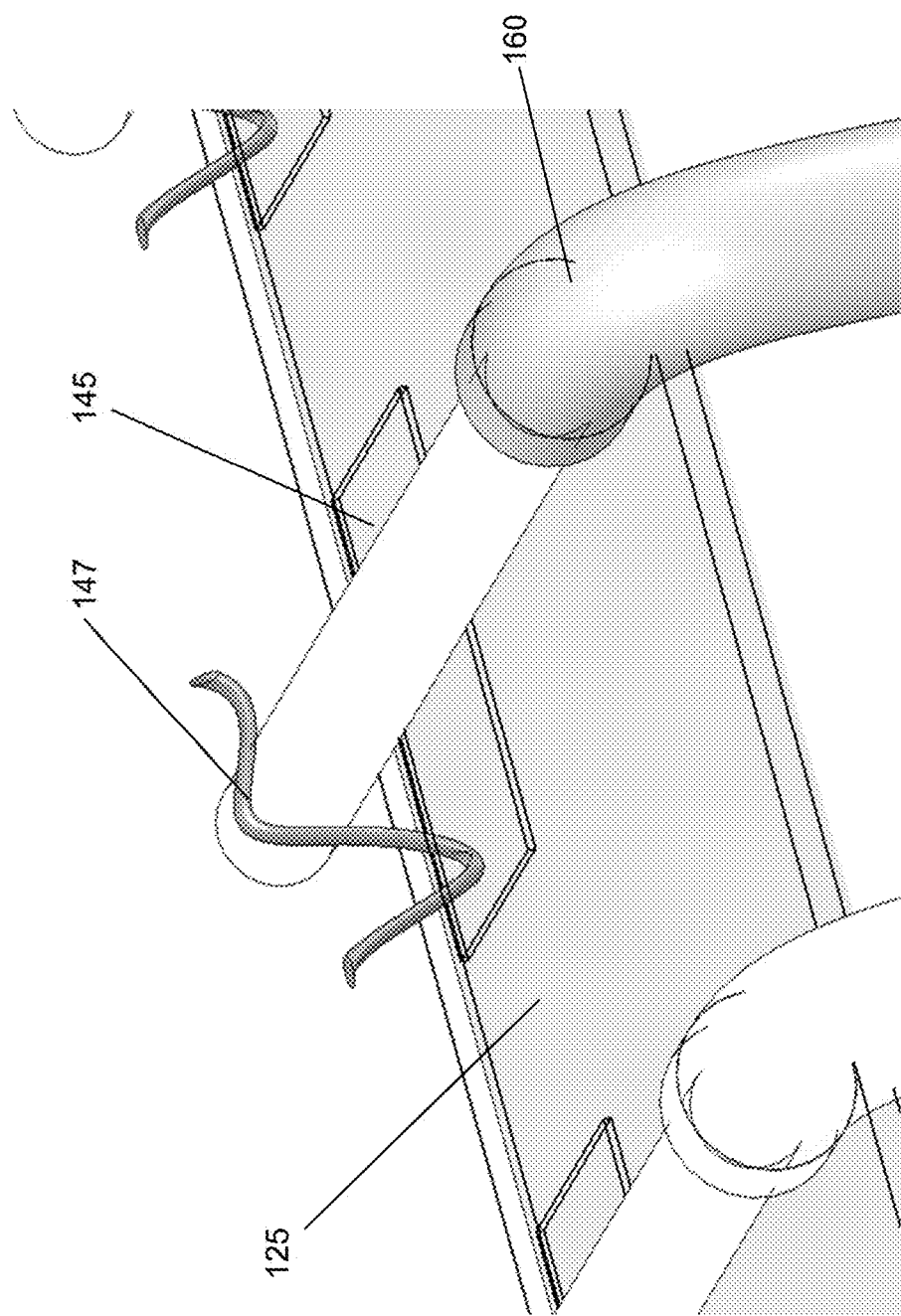
FIG. 7C illustrates the process of wire bonding the lead wire to a contact pad.

FIG. 7C illustrates the process of wire bonding a lead wire 160 to a contact pad 145. As illustrated, a lead wire 160 lies across the contact pad 145. The insulation at the end of the lead wire 160 can be removed so the conductor within the lead wire 160 can make contact with the contact pad 145. A wire bond 147 connects the contact pad 145 to the lead wire 160. A weld can be formed between the wire bond 147, the contact pad 145, and the lead wire 160 through the use of heat, pressure, ultrasonic energy, or combinations thereof.

Referring again to FIG. 4, the method 400 can also include extending the ribbon cable into the lumen formed by the molding of the MEMS film (step 403). The ribbon cable 125 can be folded such that a portion of the ribbon cable 125 and a portion of the stylet 153 are disposed within the lumen defined by the formed MEMS film 110. In some implementations, the lumen defined by the MEMS film 110 can be back filled with an encapsulating polymer, such as an epoxy. The MEMS film 110 can be placed in a cylindrical mold prior to the backfilling with the polymer. Backfilling the MEMS film 110 can serve to secure the lead wires 160 in place and electrically encapsulate the connections within the lumen. In some implementations, the backfilling process can also be used to form a cylindrical form to the distal end of the stimulation lead 100.

FIG. 8A illustrates the extension of the ribbon cable into the lumen of the molded MEMS film 110. The ribbon cable 125 can be folded such that a portion of the ribbon cable 125 and a portion of the stylet 153 is disposed within the lumen formed by the molded MEMS film 110. The portion of the ribbon cable 125 and the stylet 153 can be extended into the lumen by temporarily opening the cylinder along the seam 111.

FIG. 8B illustrates the MEMS film 110 after the backfilling process. The lumen defined by the MEMS film 110 can be backfilled, or co-molded, with a polymeric material. The backfilling process can seal the MEMS film 110 in place and electrically isolate the lead wires 160 connected to the contact pads 145 at the end of the ribbon cable 125. The backfilled polymer can fill the interior of the lumen and can also create a distal, hemispherical tip 151. In some implementations, an internal cylinder 161 is added proximal to the backfilling material over the lead wires 160. The internal cylinder 161 can reduce abrupt changes in compliance (e.g., flexibility) in the final device, when transitioning from the flexible lead wires 160 to the relatively rigid polymeric filling of the back filled MEMS film 110.

Referring again to FIG. 4 among others, the method 400 can also include coupling the molded film to a lead body (step 404). The body 150 can couple with the molded MEMS film 110 by glue or adhesive. In some implementations, the body 150 can be molded over a portion of the proximal end of the MEMS film 110. In addition to securing the body 150 to the MEMS film 110, molding the body 150 over the MEMS film 110 can help the MEMS film 110 maintain a cylindrical shape. The proximal end of the body 150 can include the one or more contacts 190.

Figure 9B:
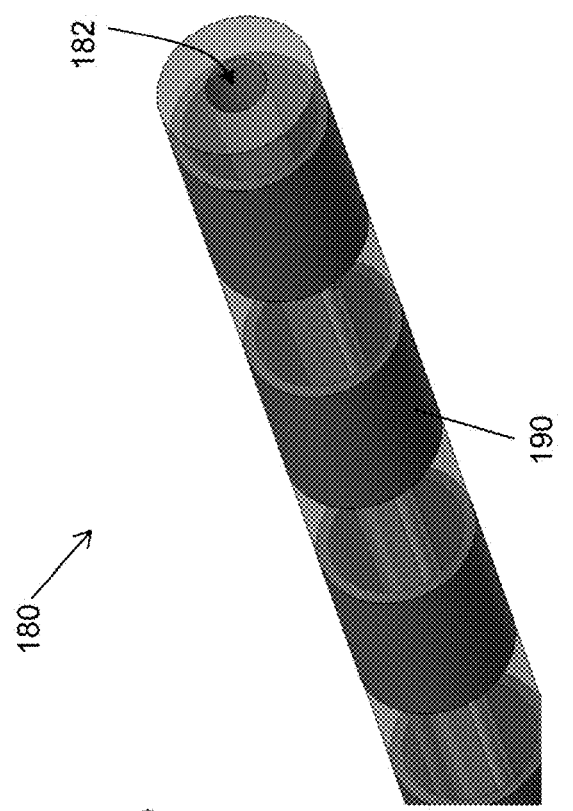
FIGS. 9A and 9B illustrate the proximal end of the stimulation lead.
Figure 9A:
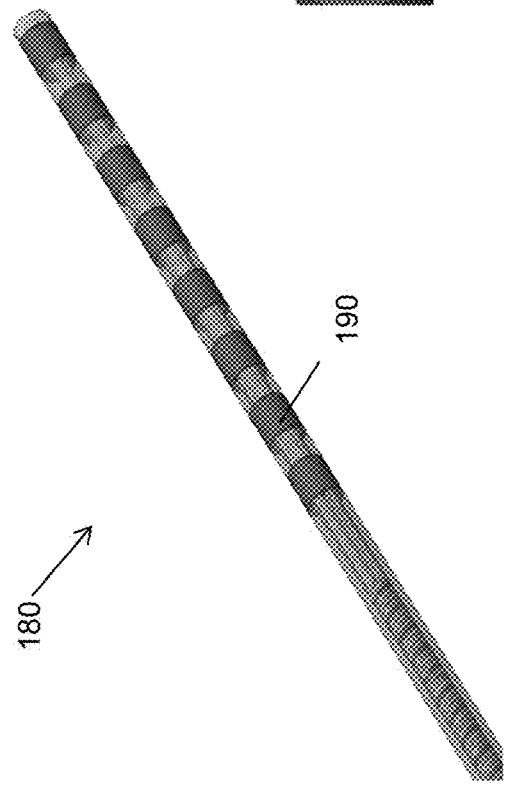

FIGS. 9A and 9B illustrate the proximal end 180 of the stimulation lead 100. The proximal end 180 of the stimulation lead 100 can include a plurality of contacts 190. As illustrate, the proximal end 180 of the stimulation lead 100 includes eight contacts 190. Each of the contacts 190 are electrically coupled with at least one of the lead wires 160. In some implementations, the proximal end 180 of the stimulation lead 100 is stiffer when compared to other portions of the stimulation lead 100. The added stiffness of the proximal end 180 can assist in the coupling of the proximal end 180 with a stimulator or an extension cable. The stimulation lead 100 can also include a lumen 182, which is illustrated in FIG. 9B. In some implementations, the lumen 182 runs the length of the stimulation lead 100.

Figure 10B:
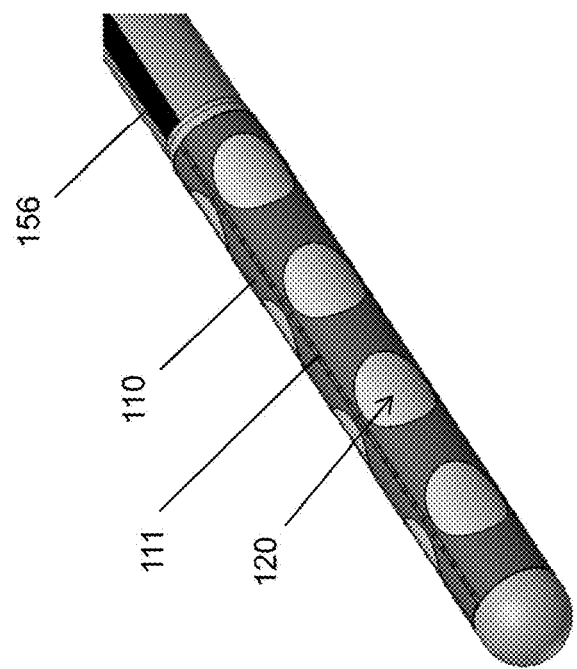
FIGS. 10A-10C illustrate the placement of the orientation mark along a portion of the body.
Figure 10A:
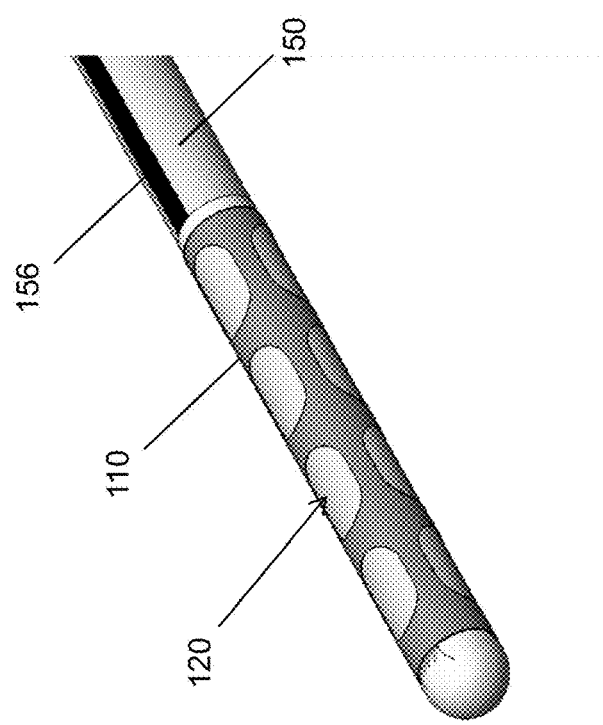
Figure 10C:
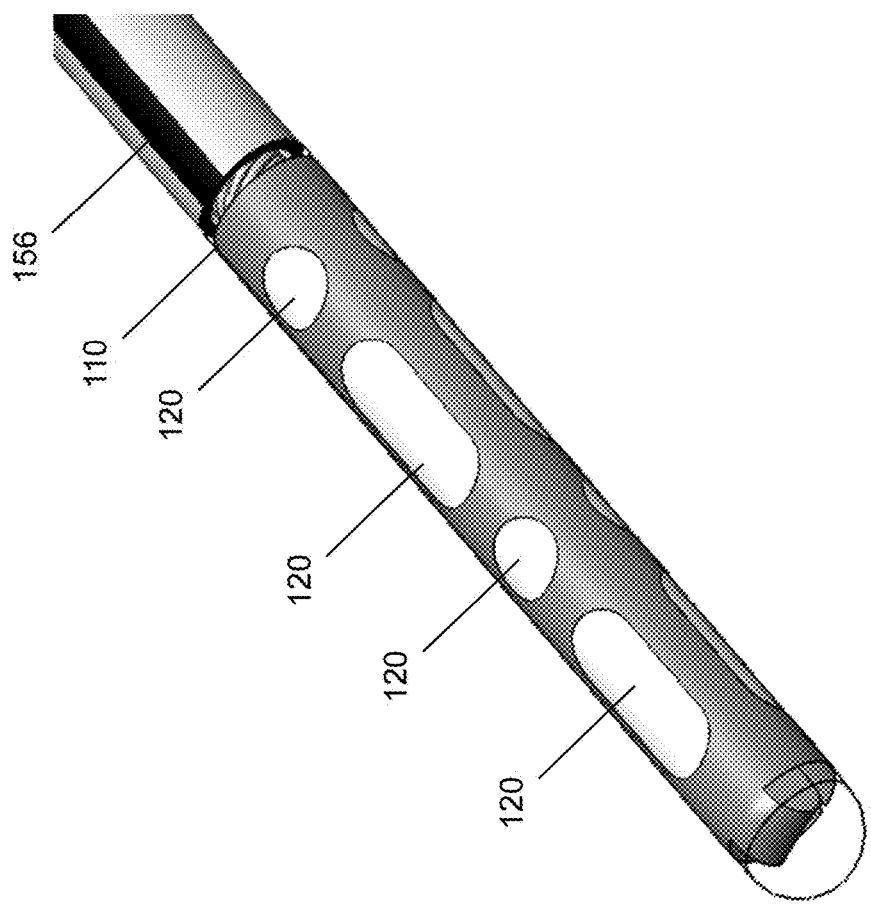

FIGS. 10A-10C illustrate the placement of the orientation mark 156 along a portion of the body 150. The orientation mark 156 can enable a neurosurgeon to determine the placement and rotation of the stimulation lead 100 when the stimulation lead 100 is implanted within the patient. For example, the orientation mark 156 may enable the neurosurgeon to determine the axial orientation (e.g., rotation) of the stimulation lead 100 and determine towards what anatomical structure the directional electrodes are facing. In some implementations, the orientation mark 156 can be a solid line extending the length of the stimulation lead 100. The orientation mark 156 can also include a dashed line or a series of dots.

The orientation mark 156 can be aligned with a specific feature (or landmark of the stimulation lead 100). For example, the orientation mark 156 can be aligned with a directional electrode 120, as illustrated in FIG. 10A. In another example, the orientation mark 156 can be aligned with the seam 111 of the MEMS film 110, as illustrated in FIG. 10B. The orientation mark 156 can also be aligned with a gap between two electrodes 120 or with the ribbon cable 125 (as illustrated, for example, in FIG. 10C).

The orientation mark 156 can be a stamped ink line or can be applied to the stimulation lead 100 during the extrusion body 150 as a dye, for example. The orientation mark 156 can alter the reflectivity of the body 150 and may be implemented as a radiopaque ink or dye in order to provide intra-operative and post-operative imaging. In some embodiments, laser marking can be used to locally change the texture, color, or reflectivity of the body 150 to serve as the orientation mark 156.

The MEMS film 110 can include a combination of stimulating electrodes and recording electrodes. In some implementations, an electrode 120 can be recording electrode or a stimulating electrode, or both. For example, to act as a stimulating electrode, the electrode 120 may be coupled with a stimulator, and to act as a recording electrode, the electrode 120 may be coupled with an analog-to-digital converter and an amplifier. In some implementations, the recording electrodes and the stimulating electrodes may be shaped or configured differently. For example, the recording electrodes may be smaller in size compared to the stimulating electrodes.

A neurosurgeon may record from one or more of the electrodes 120 during the implantation of the stimulation lead 100. For example, the neurosurgeon may record neurophysiological activity in the beta band (approximately 15-30 Hz) of neural activity because the beta band is closely associated with motor behavior.

FIGS. 11A-11I illustrate planar MEMS film 110 configurations that include different electrode designs. Each of the MEMS film 110 include three columns of electrode 120 and can therefore record electrical activity in three directions, labeled 0 degrees, 120 degrees, and 240 degrees. The MEMS film 110 may also include more than three columns of electrodes 120 to enable the stimulation lead 100 to record and stimulation in more than three directions. Each of the electrodes 120 of each of the different MEMS films 110 can be electrically isolated from one another to form directional electrodes or one or more of the electrodes 120 can be electrically coupled to one another to form omni-directional electrodes. For reference, when the MEMS films illustrated in FIGS. 11A-11I are molded into a cylinder, the end of the MEMS film toward the bottom of the page is coupled to the body 150.

Figure 11C:
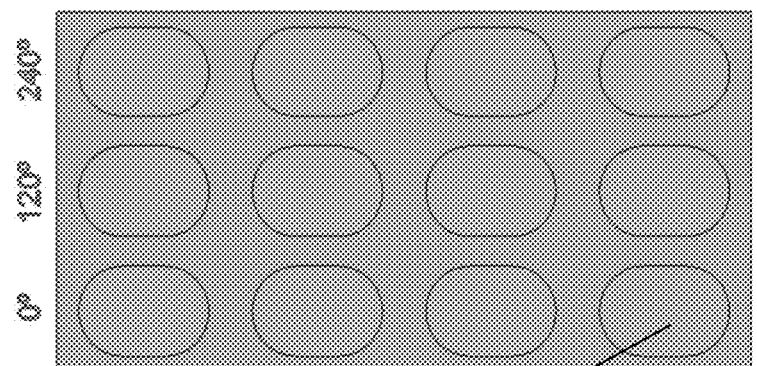
Figure 11B:
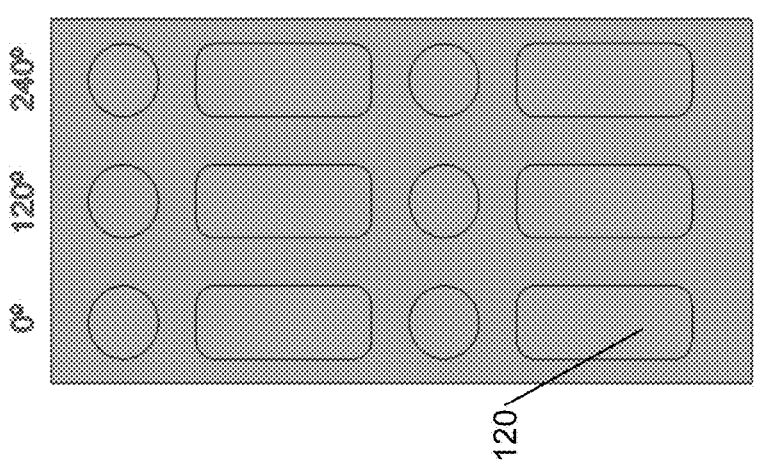
Figure 11A:
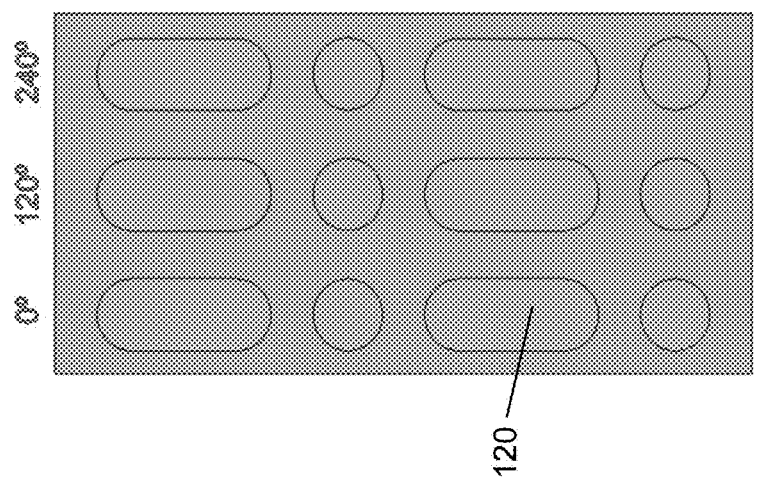

FIG. 11A illustrates the MEMS film 110 configured to have both elongated electrodes 120 and circular electrodes 120. The elongated electrodes can include semicircular ends. In some implementations, the circular electrode may be configured for use as recording electrodes and the elongated electrodes may be configured for stimulating neurological tissue. The recording electrodes can record neurological activity during the surgical descent of the stimulation lead 100 into the brain. By having recording electrodes close to the stimulation electrode, the electrical activity captured by the recording electrodes after stimulation from the stimulating electrodes can be clinically relevant to the stimulation lead 100 placement. In some implementations, recording data captured from any or all recording electrodes can be clinically relevant to determine which of the stimulating electrodes should be used to stimulate a specific target. FIG. 11B illustrates a similar implementation, but with electrodes that include rounded corners rather than semicircular ends.

FIG. 11C illustrates an implementation of a planar MEMS film where the electrodes 120 are of the same dimensions. In some implementations, the most proximal row of electrodes and most distal rows of electrodes are each electrically interconnected, and therefore each row can act as a circumferential electrode.

FIG. 11D illustrates a planar MEMS film with electrodes 120 configured as circular electrodes. The electrodes 120 configured as circular electrodes may improve charge density considerations around the edges of the electrode. FIG. 11E illustrates a planar MEMS film with electrodes 120 configured as circular electrodes of different sizes. The larger circular electrodes may be used for stimulation and the smaller circular electrodes may be used for recording. FIG. 11F illustrates a planar MEMS film with electrodes 120 configured as circular electrodes where the rows are placed closely together.

FIG. 11G illustrates a planar MEMS film with an electrode arrangement where the electrodes 120 are configured as elongated electrodes and circular electrodes. The elongated electrodes can be configured as recording electrodes and are interlaced along each row with the circular electrodes, which may be configured as stimulating electrodes. FIG. 11H illustrates a planar MEMS film with an electrode arrangement where each electrode 120 includes an inner portion 294 and an outer portion 292. In some implementations, the inner portion is a stimulation electrode and the outer portion 292 is a recording electrode. FIG. 11I illustrates a planar MEMS film where each electrode includes four bands 299. In some implementations, two or more of the bands 299 are electrically coupled together.

One or more of the electrodes 120 can include redundant traces that improve reliability of the stimulation lead 100. The electrodes 120 can be connected to the contact pads 145 on the end of the ribbon cable 125 via metal traces that are embedded in the MEMS film 110. The traces can have several redundancies around the periphery of the electrode 120 to reduce the likelihood that the electrode 120 will become disconnected from the contact pad 145 to which the electrode 120 is coupled. This design is demonstrated in FIG. 12, for example, with a simplified embodiment of a MEMS electrode film 300.

Figure 12:
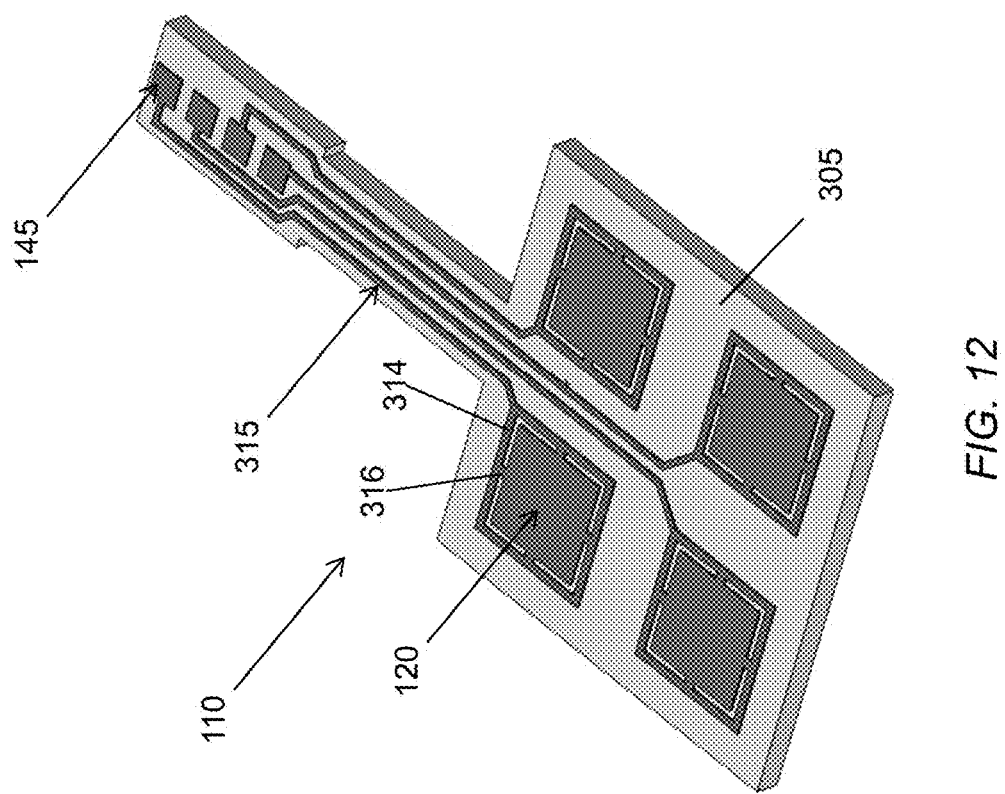
FIG. 12 illustrates an electrode with redundant periphery traces.

FIG. 12 illustrates a MEMS film with electrodes with redundant periphery traces. As illustrated a metal layer is deposited onto a polymeric layer 305. The metal layer can include the contact pads 145, the traces 315, the periphery traces 314, and the electrodes 120. Each periphery trace 314 can extend around the perimeter of an associated electrode 120. The periphery trace 314 can be coupled with an electrode 120 at a plurality of connection points 316. Each electrode 120 can include four connection points 316. In some implementations, each electrode 120 includes one or more connection points 316 per edge of the electrode 120. For example, the electrodes 120 illustrated in FIG. 12 are squares with four edges and one connection point 316 per edge. In some implementations, the contact pads 145 can also be surrounded by a periphery trace 314.

Figure 13B:
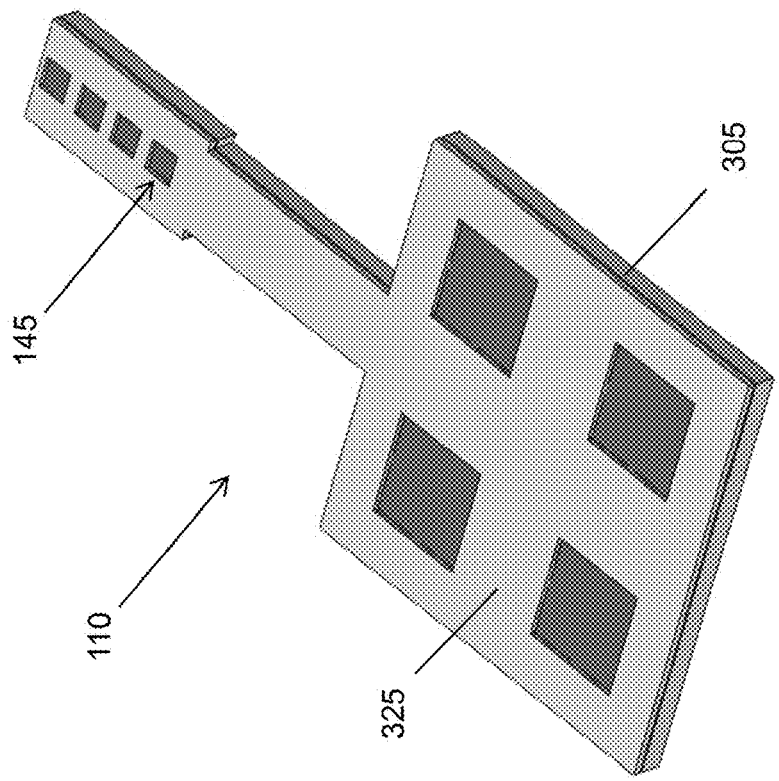
FIGS. 13A and 13B illustrate the application of a second polymeric layer to the first isolating layer illustrated in FIG. 12.
Figure 13A:
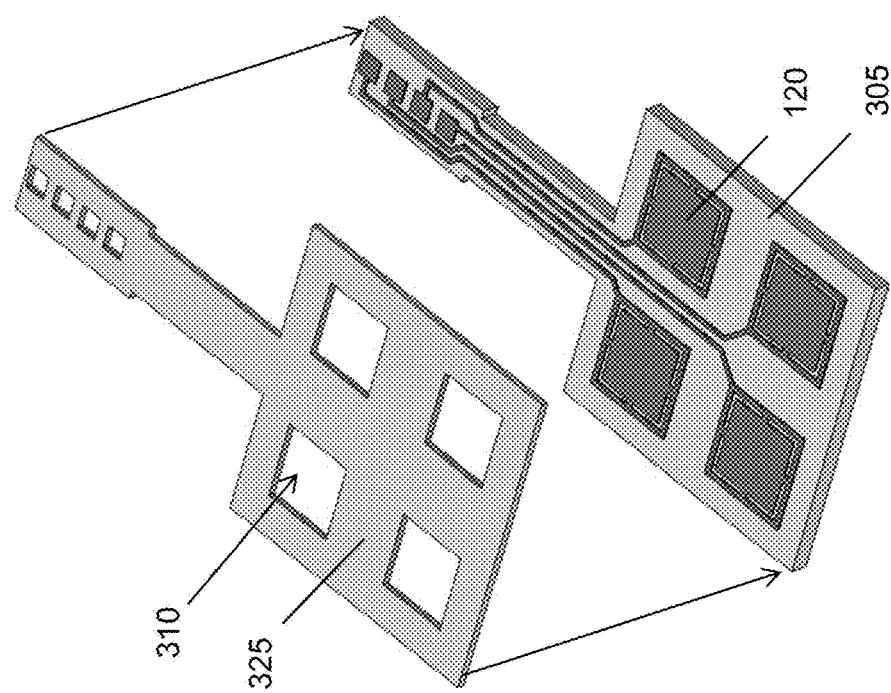

FIGS. 13A and 13B illustrate the application of a second polymeric 325 (or isolating layer) to the first isolating layer 305 illustrated in FIG. 12. The second polymeric layer 325 can include a plurality of through holes 310 that align with the electrodes 120 and the contact pads 145. The silicon based barrier layer that can be deposited over the metal layer can also include a plurality of through holes that align with the through holes 310 of the second polymeric layer. The second polymeric 325 can be bonded to the surface of the first polymeric layer 305 and the metal conductive layer. The second polymeric 325 can be photolithographically defined. The resulting stack of layers is demonstrated in FIG. 13B, where the electrodes 120 and corresponding contact pads 145 are apparent through the through holes 310, but the traces 315 and periphery traces 314 are hidden from view and electrically isolated from the outside environment.

Figure 14B:
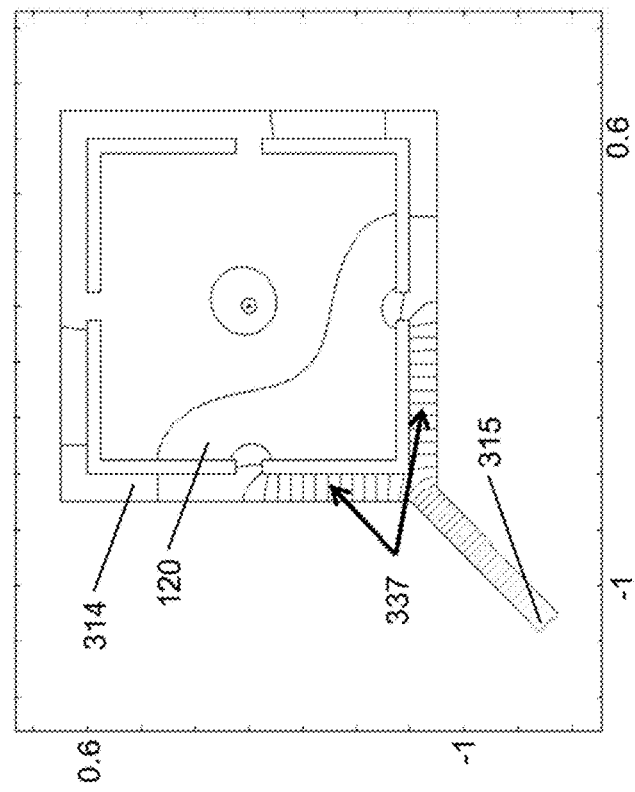
FIGS. 14A and 14B illustrate equipotential surfaces in an electrode when a voltage is applied at trace boundaries.
Figure 14A:
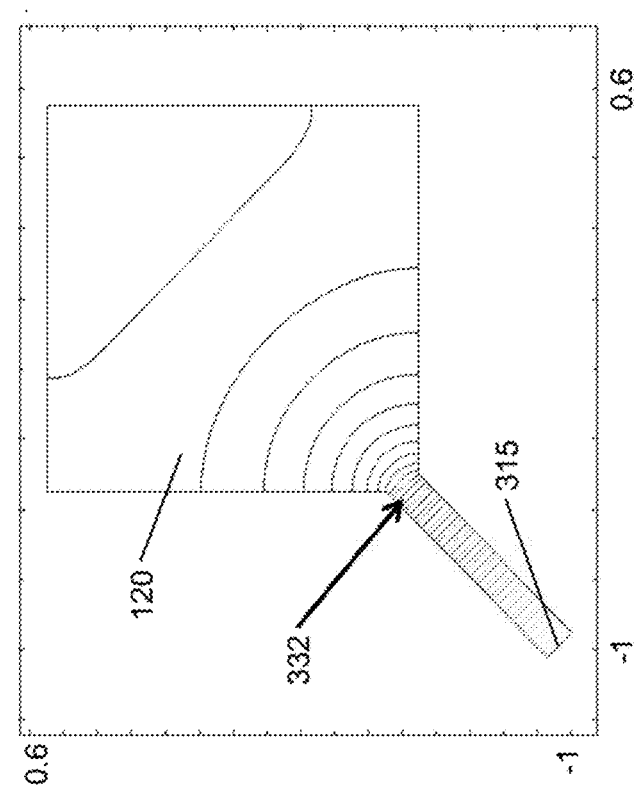

FIGS. 14A and 14B illustrate equipotential surfaces in an electrode when a voltage is applied at trace boundaries. In FIG. 14A, the electrode is only coupled to a single trace 315 and does not include a periphery trace 314. In some implementations, the junction between the trace 315 and the electrode 120 is an area where the applied voltage is highest.

FIG. 14A illustrates the equipotential surfaces 332 in an electrode 120 when a voltage is applied at trace 315. The potential is concentrated at a corner, near the junction between the trace 315 and the electrode 120. In some implementations, the concentrated potential can contribute to device reliability issues at the junction. FIG. 14B illustrates an electrode 120 with a peripheral trace 314. The peripheral trace 314, with four connection points to the electrode 120 better distributes the potential 337 throughout the electrode 120. The distribution of the potential can increase electrode health and provide redundancies if one of the connection points break.

Figures 15A, 15B:
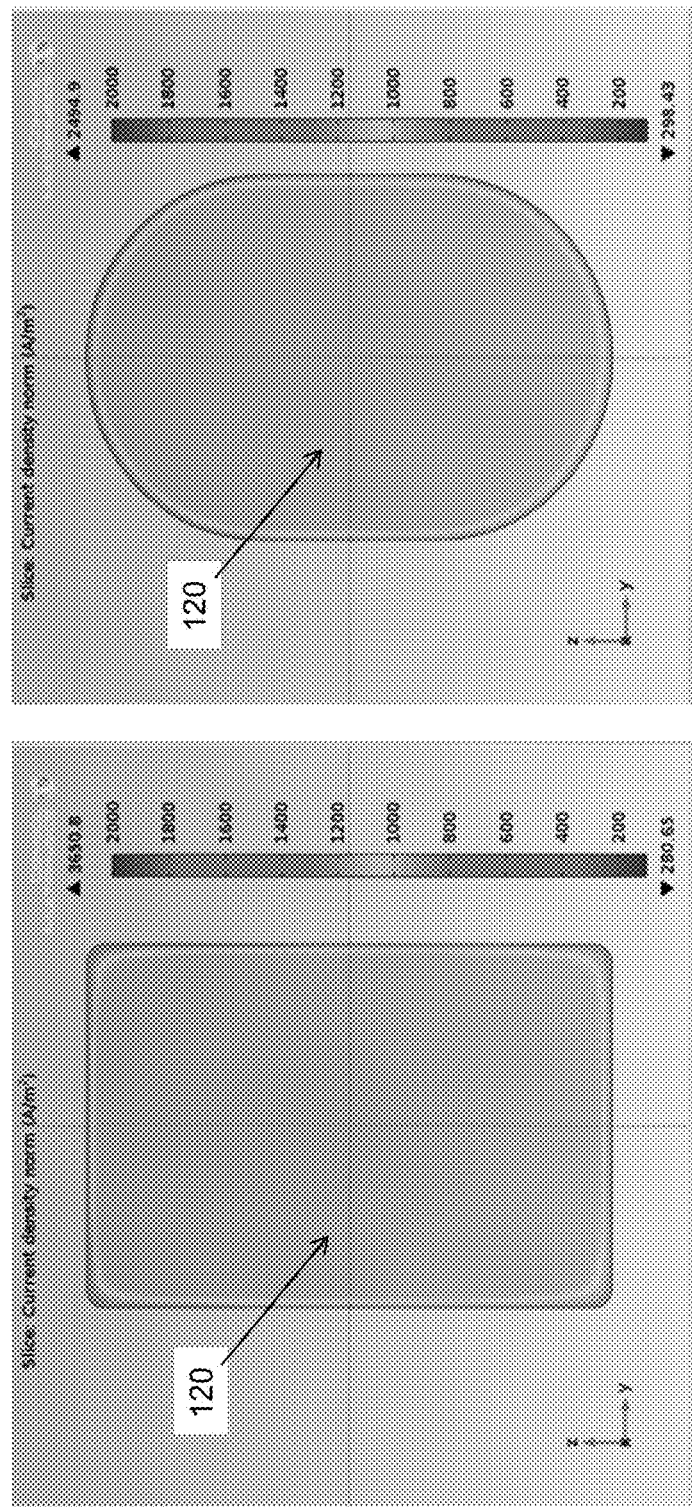
FIGS. 15A and 15B illustrate electrode current densities.

The electrodes 120 can include rounded electrode corners to decrease focal points of current density on each of the electrodes 120. FIG. 15A illustrates rectangular electrode 120 with a voltage applied to the electrode. High current densities can be generated at the corners of the electrode in this example. FIG. 15B illustrates an electrode 120 with rounded or semicircular ends, which can reduce the current density relative to rectangular corners. Reducing current density can protect the electrode from degradation.

Figures 16A, 16B:
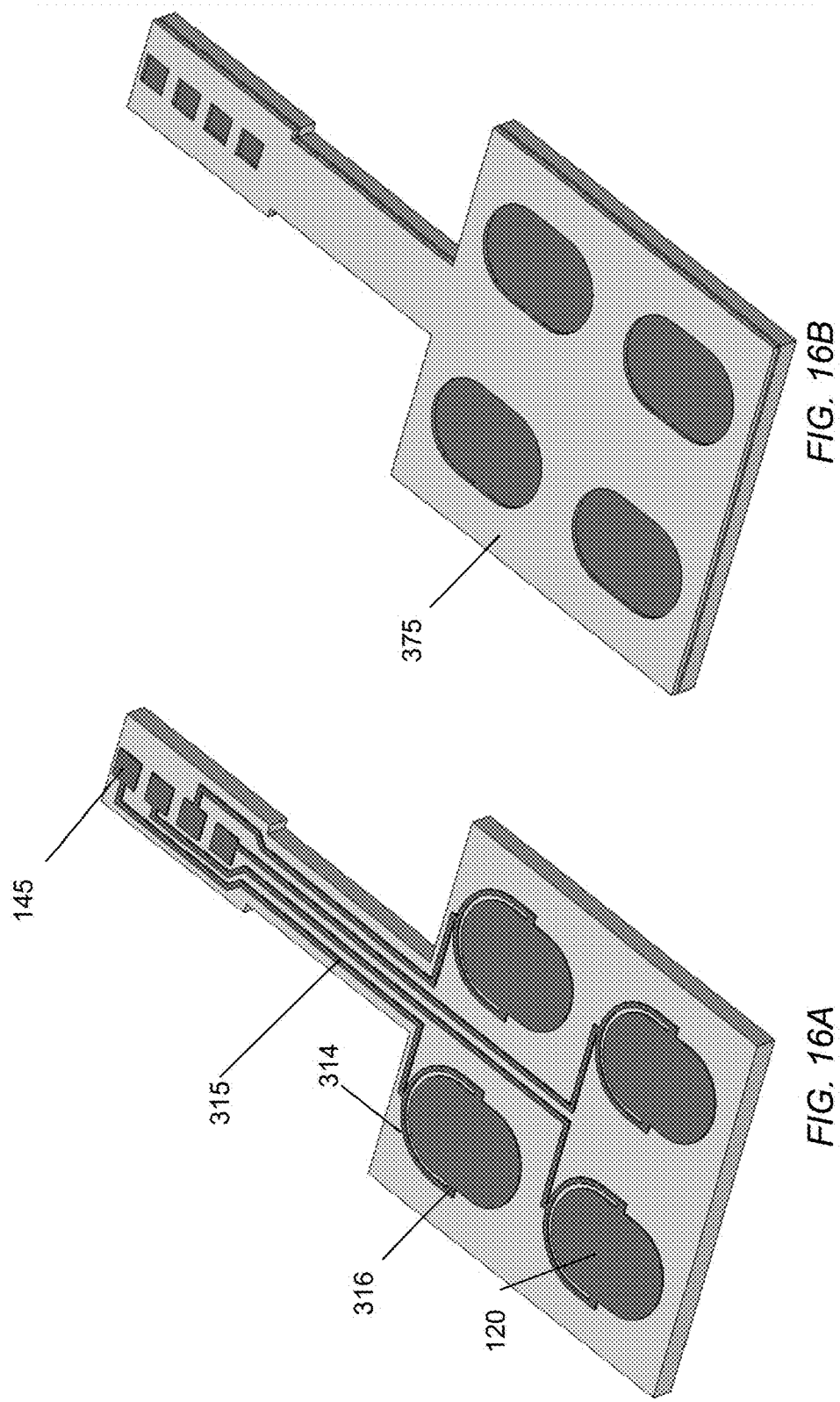
FIGS. 16A and 16B illustrate rounded corner electrodes with periphery traces.

FIGS. 16A and 16B illustrate example rounded corner electrodes with periphery traces. FIG. 16A illustrates a MEMS film with four rounded corners electrodes 120. The electrodes 120 are connected to contact pads 145 through the traces 315. The trace 315 are coupled with periphery traces 314 that enable voltage distribution to be equal at contact points 316, and thereby distributed the voltage more evenly across the electrode surface. As illustrated, the periphery traces 314 do not encircle the perimeter of the electrodes 120; however, in some implementations, the periphery traces 314 can fully encircle the perimeter of the electrodes 120. FIG. 16B illustrates the MEMS film with a second polymeric layer 375 in place, encapsulating the periphery traces 314 and the traces 315.

Figure 17:
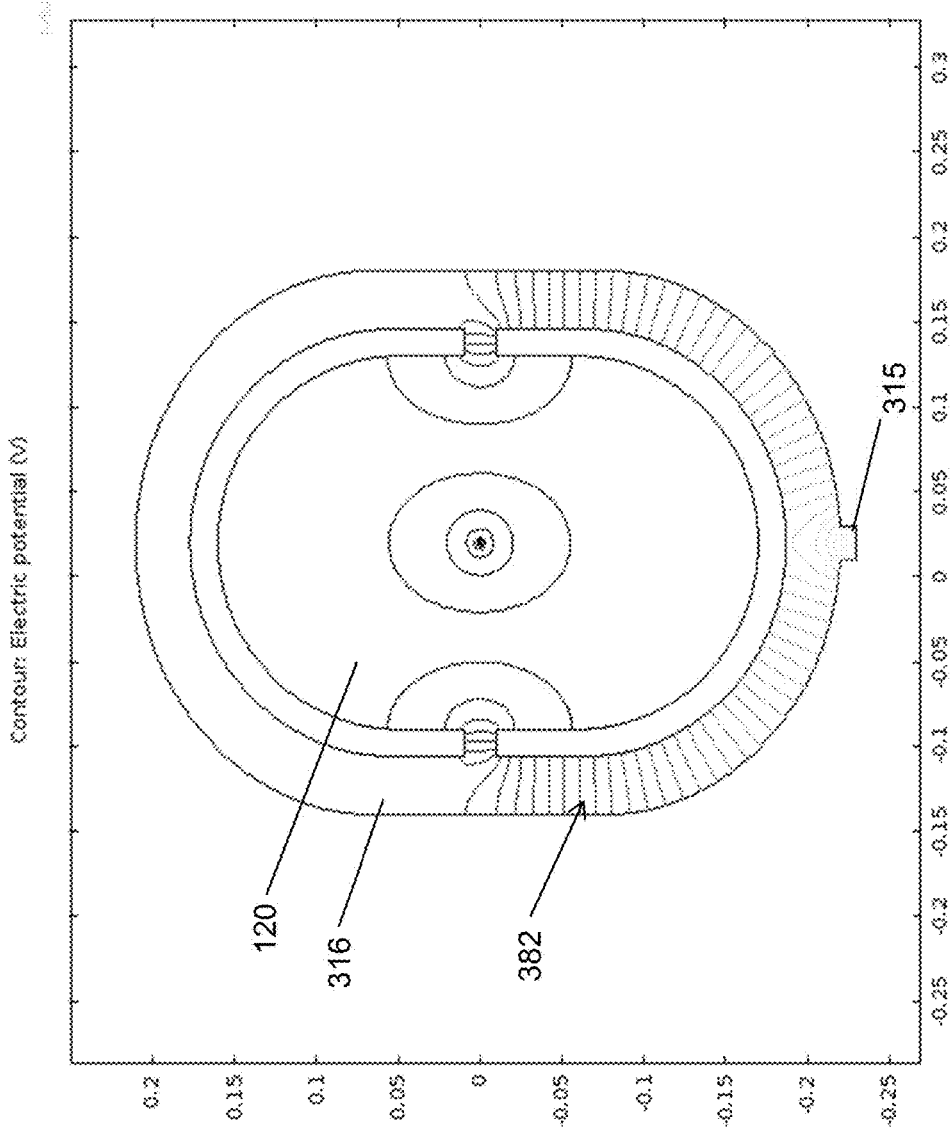
FIG. 17 illustrates a current density distribution in an electrode with rounded corners and coupled to a periphery trace.

FIG. 17 illustrates a current density distribution in an electrode with rounded corners and coupled to a periphery trace. A rounded corner electrode 120 is fully surrounded by a periphery trace 314. The periphery trace 316 makes two connections to the electrode 120. When a potential is applied to the trace 315, the equipotential regions 382 distribute around the periphery trace 316 and enter the electrode 120 at the two connection points. By applying the potential to multiple points of the electrode 120, the potential is more evenly distributed across the electrode 120.

Figure 19:
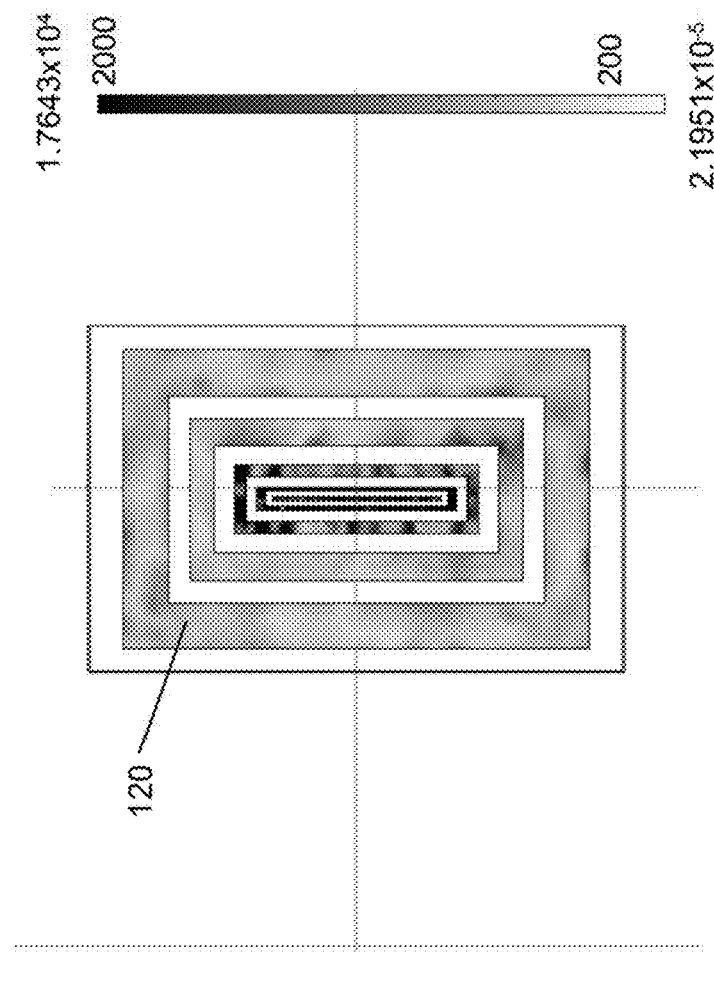
FIG. 19 illustrates a mesh configured electrode.
Figure 18:
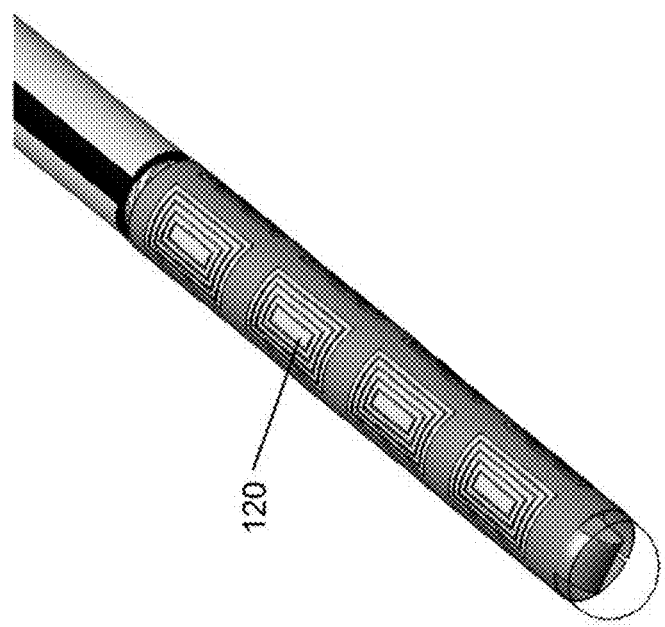
FIG. 18 illustrates a MEMS film with a plurality of electrodes configured as mesh electrodes.

The electrodes 120 can include meshes. FIG. 18 illustrates a MEMS film 110 with a plurality of electrodes 120 configured as mesh electrodes. A mesh electrode configuration can be used to concentrate current density in certain areas of the electrode surface—for example, the center. FIG. 19 illustrates an electrode 120 configured as a mesh electrode. A mesh electrode 120 can include a plurality of concentric bands. In some implementations, each of the bands are of the same thickness and in other implementations, as illustrated in FIG. 19, each of the bands may be narrower toward the center of the electrode 120. Narrowing each of the bands towards the center of the mesh electrode 120 can increase current density towards the center of the electrode 120, and thereby limit the spread of current from the electrode's perimeter. In some implementations, a mesh electrode has the effect of concentrating the volume of tissue being influenced by the electric current to the center of the electrode, therefore increasing the effect of directional stimulation in the patient.

Figure 21:
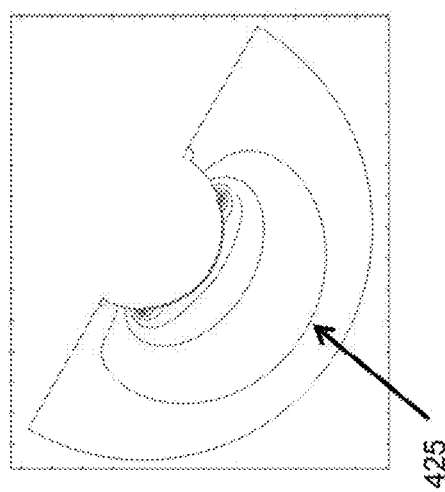
FIG. 21 illustrates a finite element analysis model of the current density around a mesh gradient electrode.
Figure 22:
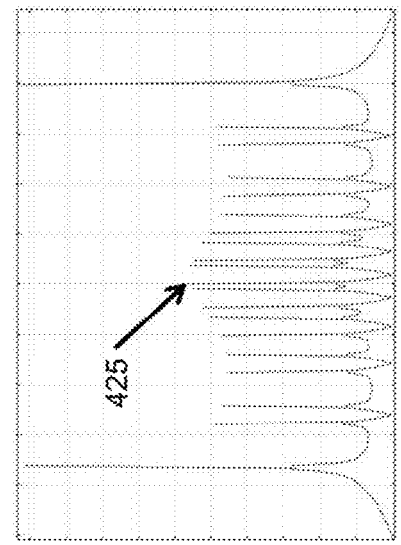
FIG. 22 illustrates the current density along an arc length circumferential to the electrode modelled in FIG. 21.
Figure 20:
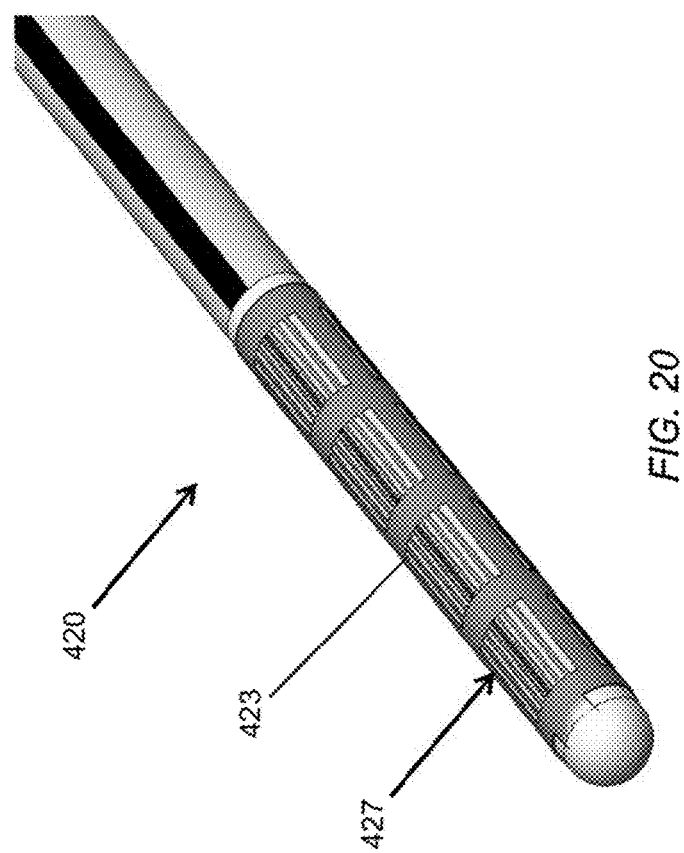
FIG. 20 illustrates a mesh electrode configuration with a plurality of bands.

FIG. 20 illustrates a mesh electrode configuration with a plurality of bands. The MEMS film 420 includes a plurality of mesh gradient electrodes 427. Each of the mesh gradient electrodes 427 includes a plurality of electrode bands 423. In some implementations, the bands are narrower toward the center of the mesh gradient electrode 427. The narrowing of the bands can concentrate current density towards the center of the electrode 427. FIG. 21 illustrates a finite element analysis model of the current density 425 around a mesh gradient electrode, which shows that current density is the highest toward the center of the mesh gradient electrode 423. FIG. 22 illustrates the current density 425 along an arc length circumferential to the electrode modelled in FIG. 21. The numerical analysis illustrated in FIGS. 21 and 22 shows that current density peaks can be shifted away from the periphery of the electrodes and into the center of the electrode using mesh electrodes.

Figure 23C:
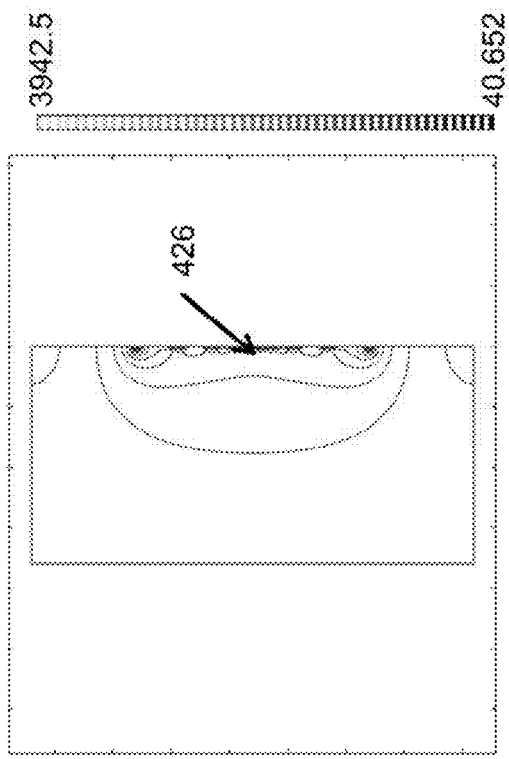
FIGS. 23B-23E illustrate a finite element analysis of a gradient mesh electrode.
Figure 23B:
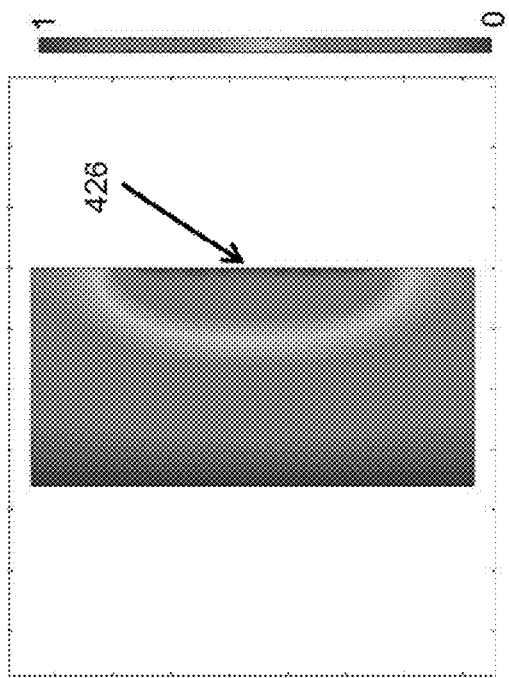
Figure 23E:
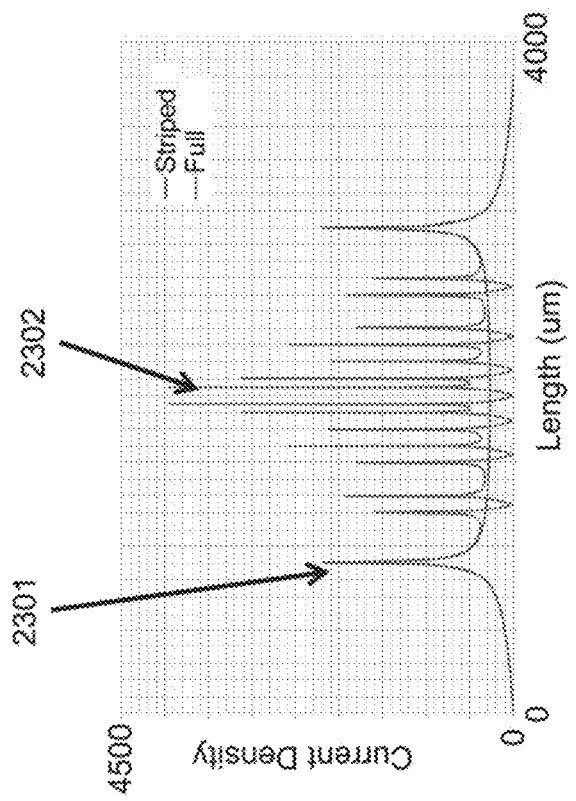
Figure 23D:
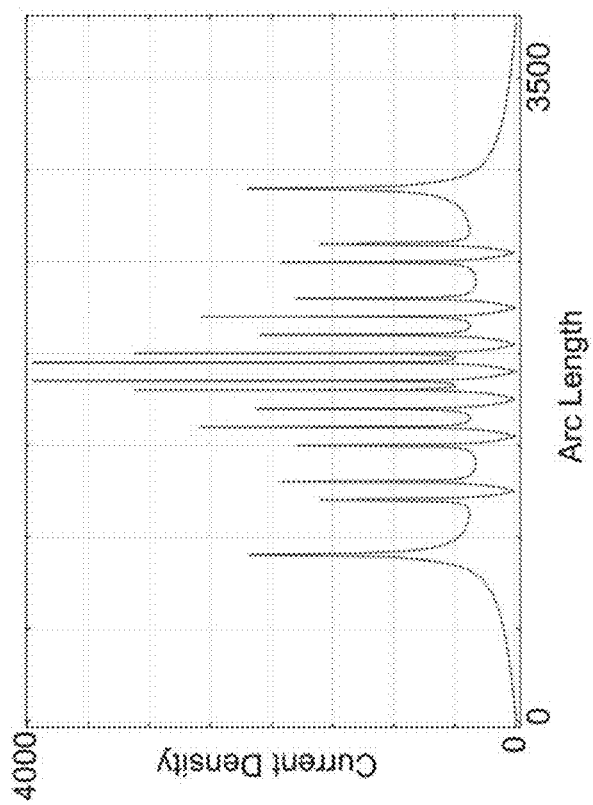

FIG. 23A illustrates a MEMS film with gradient electrodes turned perpendicular to the length of the stimulation lead 100. The gradient mesh electrode 427 is implemented on the MEMS film to concentrate a volume of the current longitudinally along the MEMS film. FIGS. 23B and 23C illustrate a finite element analysis model of the electric potential at the surface of the gradient mesh electrode 427 when in contact with conductive media. The numerical analysis demonstrates that the current density peaks 426 can be shifted away from the periphery of the electrodes and toward the center of the electrode 427 using a gradient mesh. FIG. 23D illustrates the peaks of current density 426 along the electrode longitude, and suggests that with proper gradient meshing the peaks of high current density can be driven away from the periphery toward the center of the electrode. FIG. 23E illustrates the difference between current density 2301 of a non-meshed electrode. The current density 2301 of the non-meshed electrode includes current density peaks at its periphery. The current density 2302 of the gradient mesh electrode includes a plurality of peaks toward the center of the electrode.

In some implementations, the gradient mesh configurations increase efficacy of electrical stimulation in human subjects by avoiding side effects and concentrating a stimulation signal on regions of intended targets.

Figure 24B:
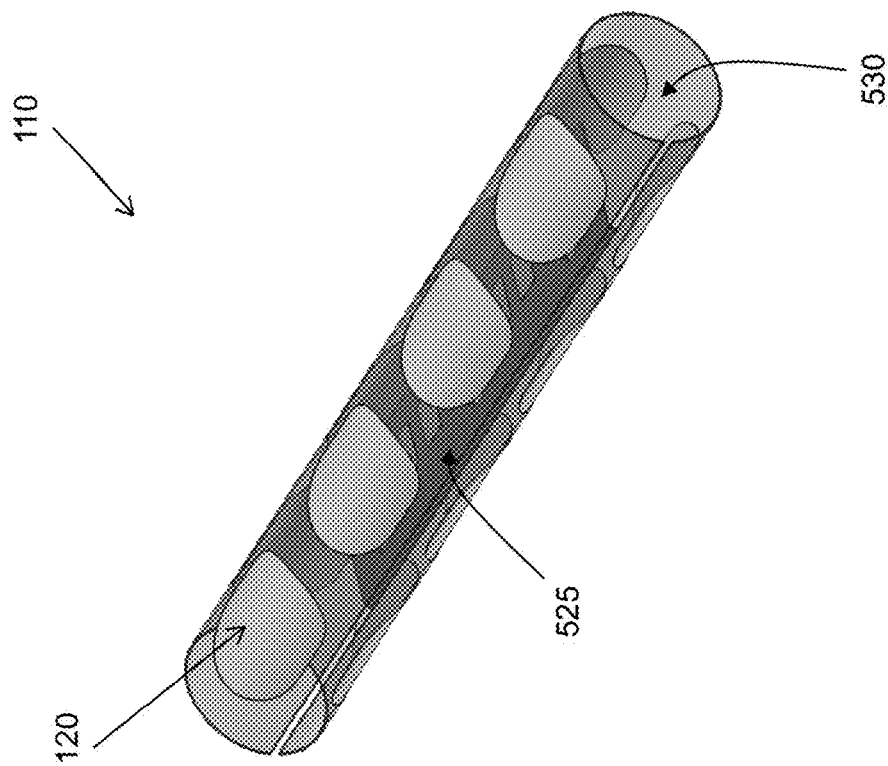
FIGS. 24A and 24B illustrate a MEMS film configuration without a ribbon cable.
Figure 24A:
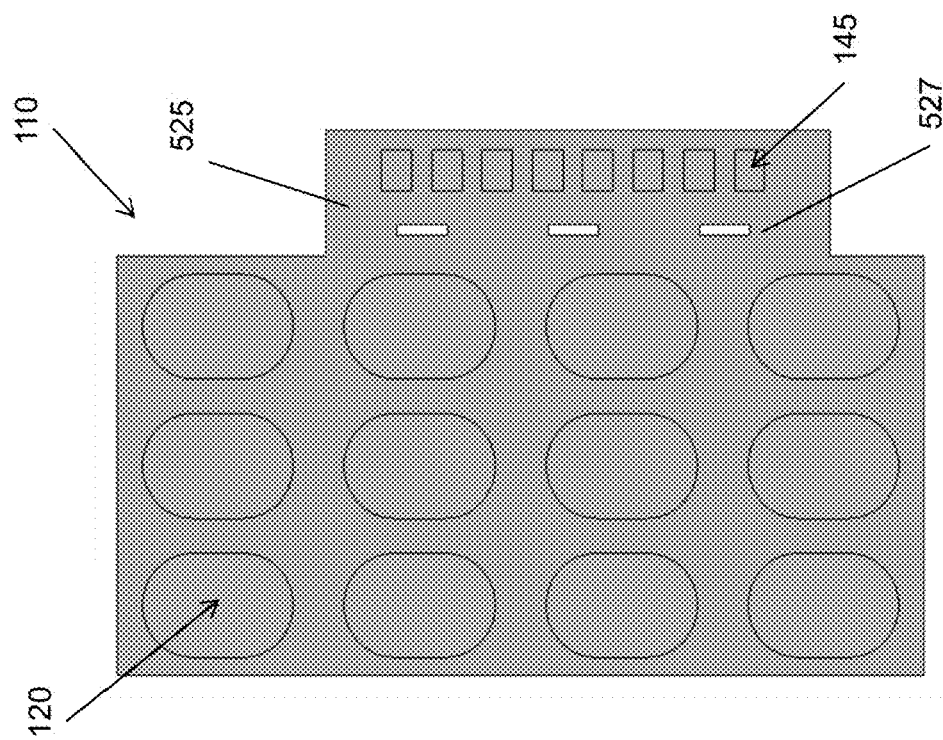

FIGS. 24A and 24B illustrate a MEMS film 110 configuration without a ribbon cable. FIG. 24A illustrates a MEMS film 110 without a ribbon cable in a planar configuration. A contact pad area 525 extends from the MEMS film 110. The contact pad area 525 a plurality of contact pad 145. The electrode 120 is electrically coupled with one or more contact pads 145 by traces. The MEMS film 110 can also include a plurality of vias 527 (or holes in the MEMS film 110). The vias 527 can aid in assembly, by enabling the encapsulating epoxy to flow around the contact pad area 525 and fully encapsulate the contact pad area 525. The vias 527 can also improve bending at the junction of the MEMS film 110 and the contact pad area 525.

FIG. 24B illustrates the MEMS Film 110 after thermal reforming into a cylindrical shape. The molded MEMS film 110 defines an inner lumen 530. The contact pad area 525 is folded into the lumen 530. In some implementations, the lumen 530 is backfilled with an encapsulating epoxy.

FIG. 25A illustrates MEMS film without a ribbon cable coupled to a style and coupled with a body 150. As illustrated the top portion of the MEMS film without a ribbon cable is removed to view the interior of the lumen defined by the molded MEMS film. The contact pad area 525 is coupled with a stylet 153 and lead wires 160 are coupled with the contact pads 145. FIG. 25B illustrates the same embodiment as illustrated in FIG. 25A, but from a different angle. In these and other examples, sections of the MEMS film are removed to illustrate the inner features.

FIG. 25C illustrates the MEMS Film 110 without a ribbon cable in an assembled and overmolded state. After the lead wires 160 are welded in place, MEMS Film 110 is backfilled with a polymer or epoxy solution to order to fortify the cylindrical shape. The polymer also encapsulates and isolates the lead wires 160 connections to the contact pads 145. In some implementations, the MEMS film without a ribbon cable is more reliable compared to a MEMS film with a ribbon cable. The contact pad area 525 can also provide more spacing between electrode sites 120 for traces leading to the contact pads 145.

Figure 26B:
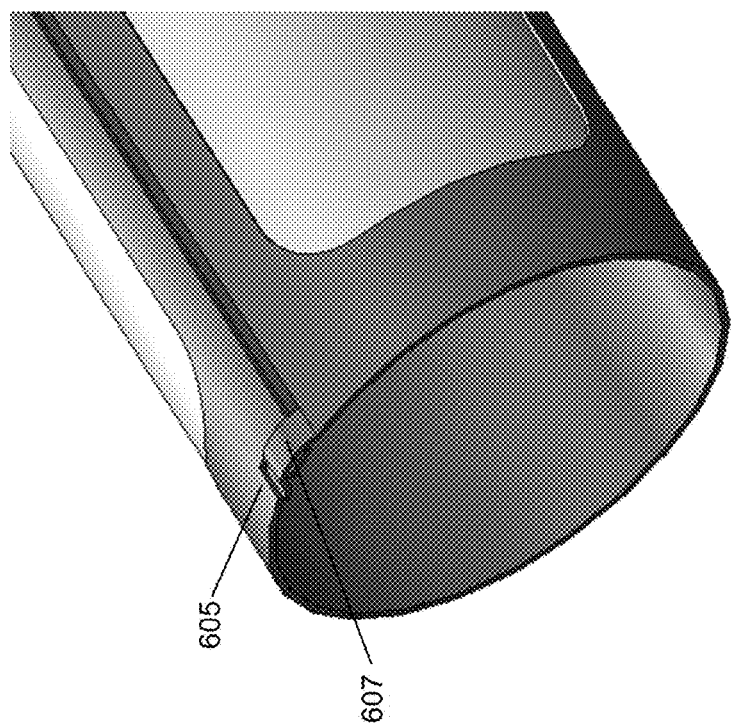
Figure 26A:
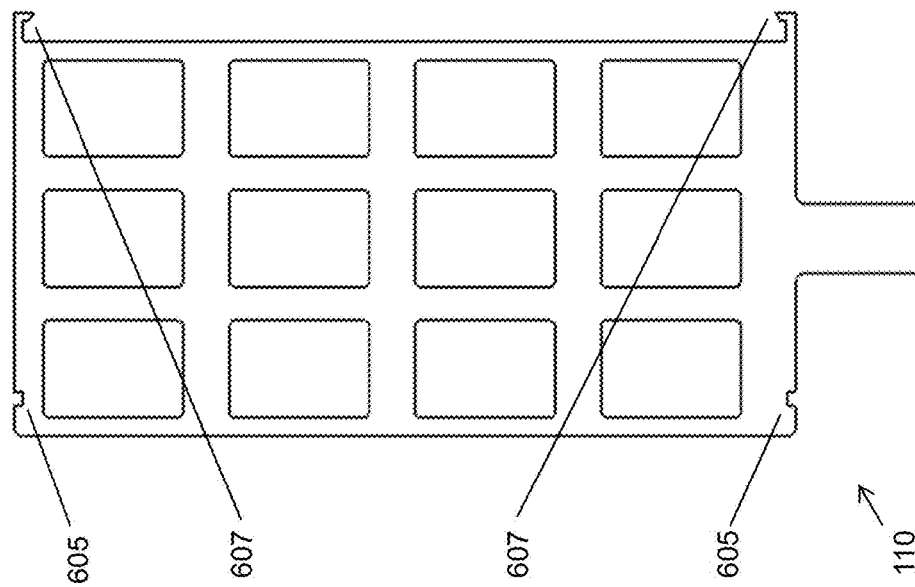

FIGS. 26A-26H illustrate methods for maintaining the cylindrical shape of the planar formed, cylindrical MEMS film. FIG. 26A illustrates a MEMS film 110 that can maintain the cylindrical shape with hooks and clips. The MEMS film 110 can include two hooks 607 and two notches 605, or other number of hooks or notches. FIG. 26B illustrates the planar formed, cylindrical MEMS film 110 with the hook 607 coupled with the notch 605. When the MEMS film 110 is formed into a cylinder, the hook 607 and notches 605 on opposite sides of the MEMS film 110 are aligned with one another. Each hook 607 can slide into the recess of its matching notch 607. In some implementations, the seam of the planar formed, cylindrical MEMS film 110 may also be glued in place.

Figure 26D:
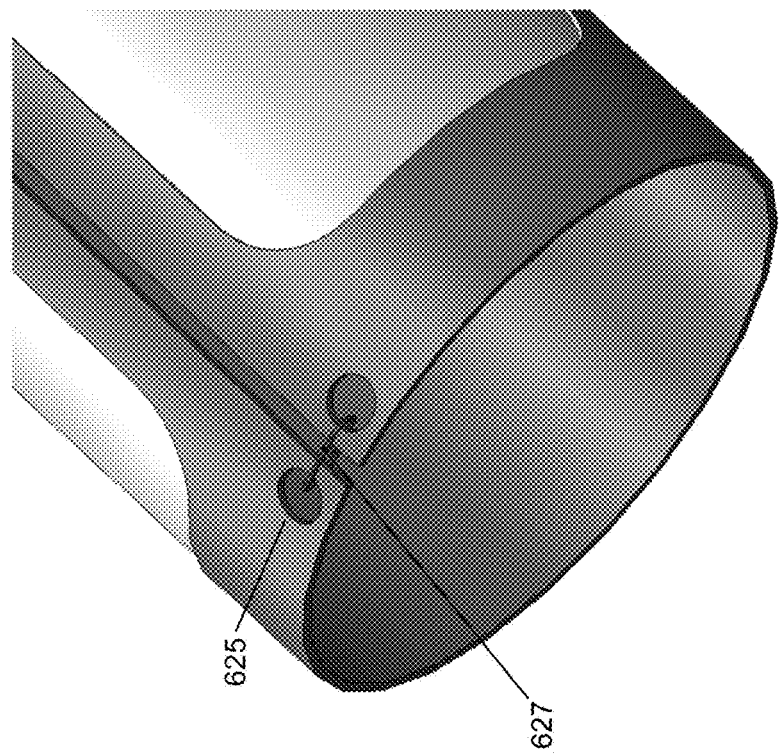
Figure 26C:
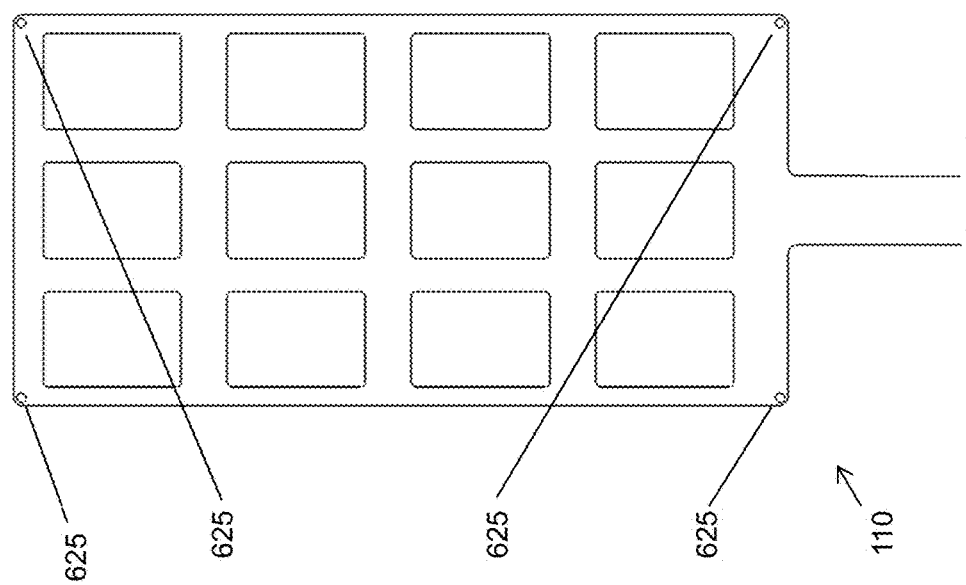

FIG. 26C illustrates the use of securing holes 625 to maintain the cylindrical shape of the planar formed, cylindrical MEMS film 110. The MEMS film 110 includes a hole 625 at each of the corners of the MEMS film 110. In some implementations, the MEMS film 110 can also include addition holes 625 along each long edge of the MEMS film 110. As illustrated in FIG. 26D, when the MEMS film 110 is formed into a cylinder, two holes 625 are aligned with one another. A wire 627 can be run through each of the holes 625 to secure the seam and maintain the cylindrical shape of the planar formed, cylindrical MEMS film 110. The wire 627 can be a metal or polymer wire, a staple, or a clip.

FIG. 26E illustrates the distal end of a planar formed, cylindrical MEMS film 110. The MEMS film 110 can include an under hang 634 that is positioned under the opposite edge 632 of the MEMS film 110. The under hang 634 can provide a platform for applying an adhesive. The under hang 634 and the opposite edge 632 can be mechanically pressed together to form a seal at the seam of the planar formed, cylindrical MEMS film 110. In some implementations, the under hang 634 can extend into the lumen defined by the planar formed, cylindrical MEMS Film 110. In these implementations, when the lumen is backfilled with epoxy, the under hang 634 can be trapped within the epoxy, preventing the unravelling of the planar formed, cylindrical MEMS Film 110. In some implementations, as illustrated in FIG. 26F, the under hang embodiment can include a plurality of holes 625. As in the above, illustrated example, the two edges of the MEMS film 110 can be bound together by a wire 627 that passes through each of the holes 625.

Figure 26G:
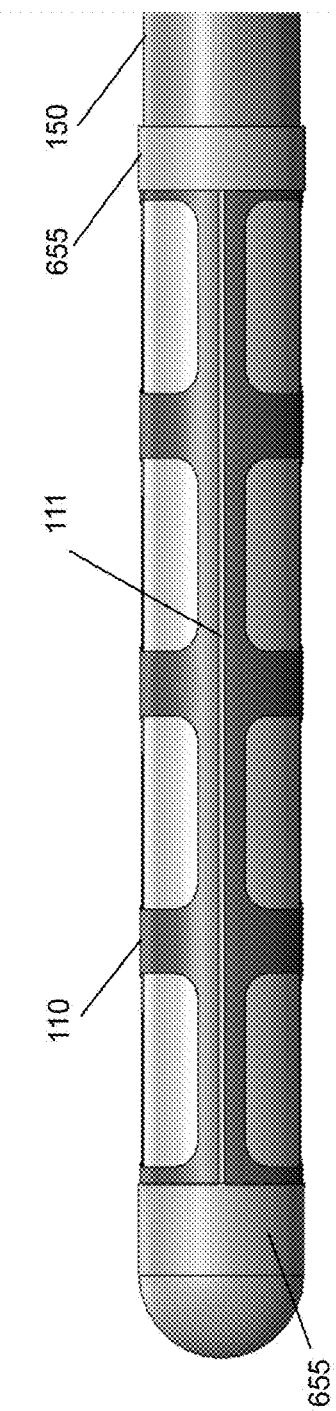
Figure 26H:
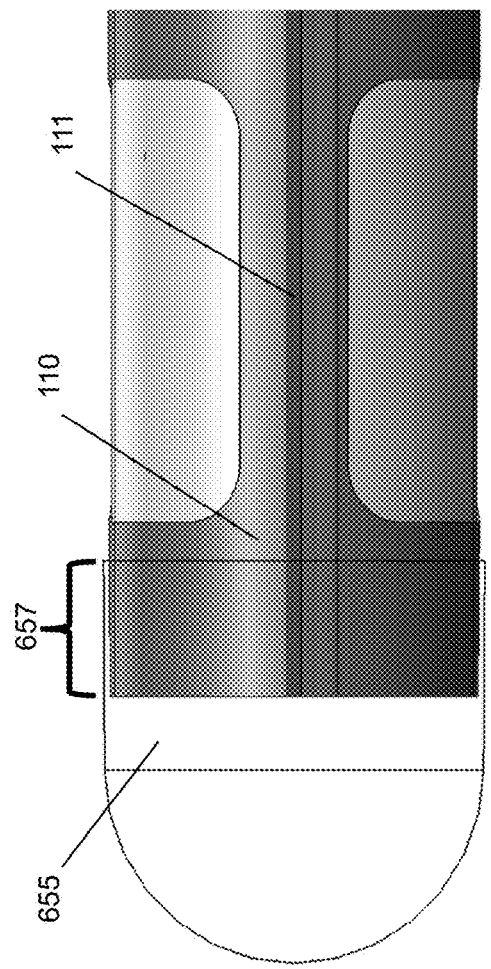

FIGS. 26G and 26H illustrate an over molding method for maintaining the cylindrical shape of the planar formed, cylindrical MEMS film 110. Once formed into a cylindrical shape, an end cap can form a collar 655 over the distal end of the MEMS film 110. The body 150 can form a collar 655 over the proximal end of the MEMS film 110. As illustrated by FIG. 26H, the collar 655 of the end cap (and the collar 655 of the body 150) overlaps the MEMS film 110 by a predetermined distance 657. In some instances, the collar 655 may extend longitudinally over the seam 111 in order to enclose the gap formed by the edges of the MEMS film 110 along the length of the cylinder shape.

Figure 27A:
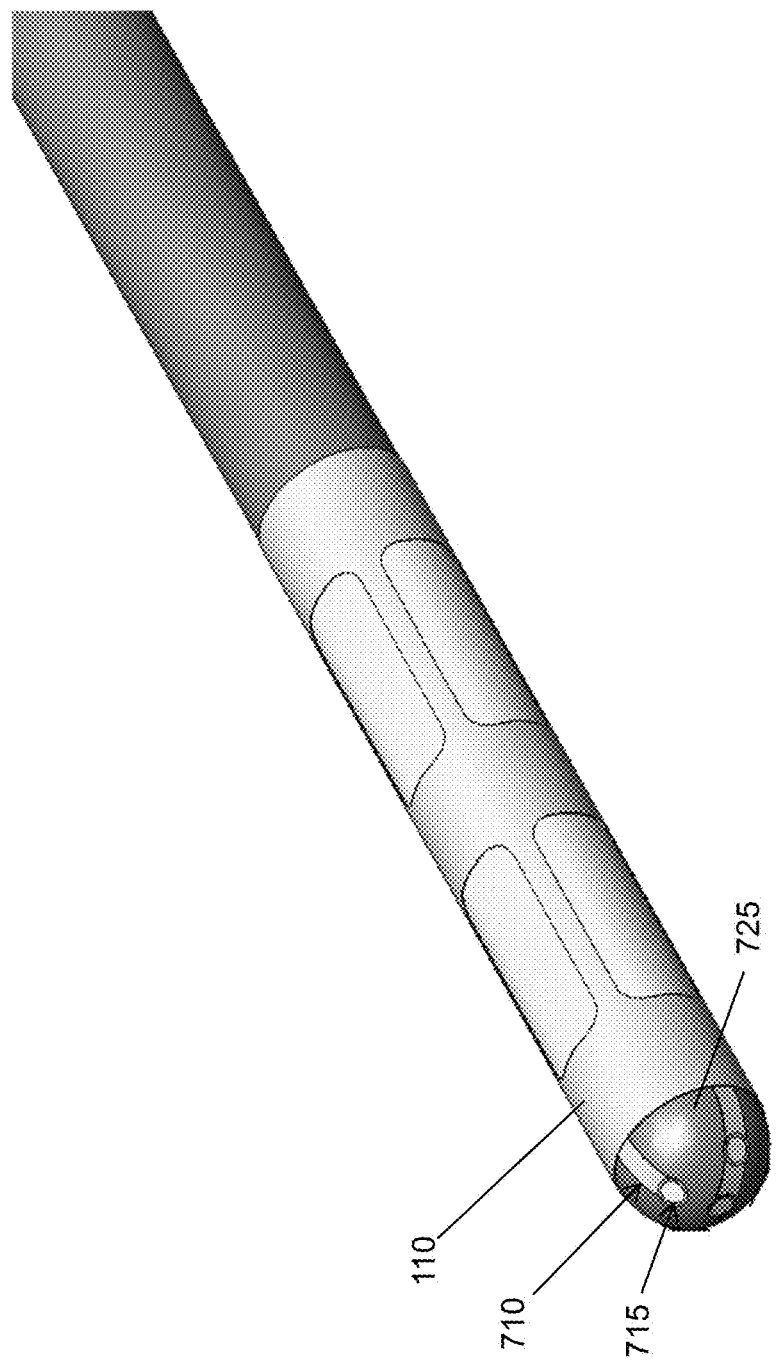
FIGS. 27A-27C illustrate example end cap electrodes.

The stimulation lead 100 can include distal recording sites on the end cap of the stimulation lead 100. FIG. 27A illustrates an example MEMS film 110 with end cap electrodes. The stimulation lead 100 can include a plurality of end cap electrodes 715 coupled with the end cap 725 of the stimulation lead 100. As illustrated in FIG. 27A, the stimulation lead 100 includes five end cap electrodes 715 disposed along four end tags 710. The end cap electrodes 715 can be used to identify neural activity during the implantation of the stimulation lead 100 into a patient's brain. The end tags 710 can be coupled with the end cap to ensure that the end cap electrodes 715 remain in in place during implantation.

Figure 27C:
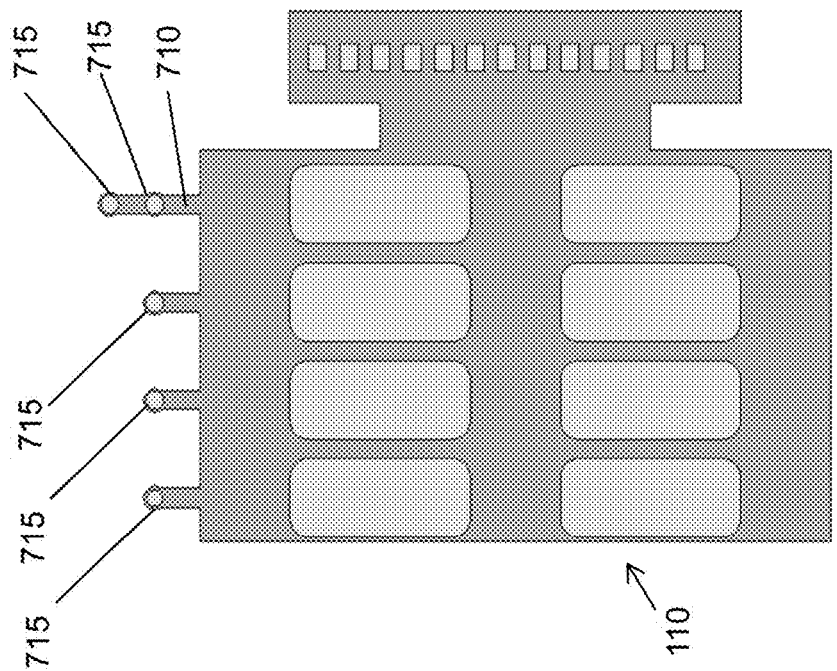
Figure 27B:
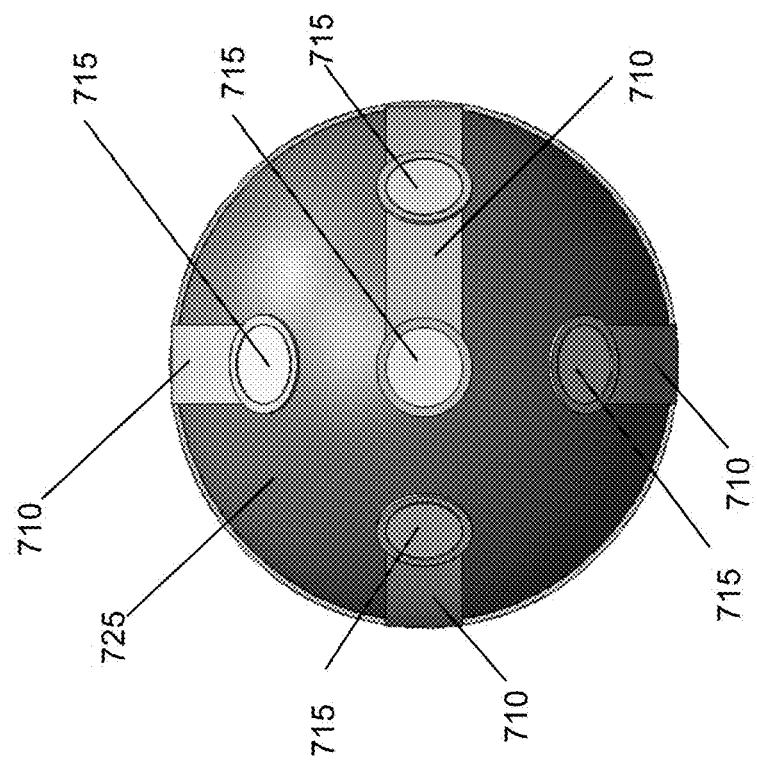

FIG. 27B illustrates an end view of the stimulation lead 100 configured to include distal recording sites. As described above, the stimulation lead 100 may include five end cap electrodes 715 disposed on the surface of the end cap 725. The stimulation lead 100 may include a central end cap electrode 715 and then a plurality of end cap electrodes 715 positioned slightly proximal to the central end cap electrode 715. In some implementations, one of the end cap electrodes 715 positioned slightly proximal to the central end cap electrode 715 is pointed in each of the anterior, posterior, lateral, and medial directions.

FIG. 27C illustrates the planar MEMS film 110 with end cap electrodes 715. Four end tags 710 extend from the distal end of the MEMS film 110. In some implementations, the MEMS film 110 may include more than four end tags 710. For example, the MEMS film 110 may include between 5 and 12 end tags 710. At least one end cap electrode 715 is disposed on each of the end tags 710. In some implementations, one of the end tags 710 is longer and includes an additional end cap electrode 715. The longer end tag 710 can extend to the apex of the end cap 725, and the end cap electrode 715 at the end of the loner end tag 710 is the central end cap electrode 715 when applied to the end cap 725.

A MEMS film can couple with an existing stimulation lead. FIG. 28A illustrates a MEMS film 730 coupled to an existing stimulation lead, such as a Medtronic 3389 DBS Lead (Medtronic Inc., Minn.). The MEMS film 730 can be positioned between or around existing ring electrodes 755. The MEMS film 730 can add additional electrodes 120 and end cap electrodes 715 to the existing stimulation lead. The addition of the MEMS film 730 can add the ability of recording or stimulating directionally to the existing stimulation lead. FIG. 28B illustrates the MEMS film 730 in a planar configuration. The MEMS film 730 includes four electrodes 120 disposed along a single arm 742 and one end cap electrode 715. In some implementations, the MEMS film 730 includes multiple rows of electrodes 120 disposed across one or more arms 742. Each of the arms 742 can be configured to fit between each of ring electrodes 755.

The stimulation lead can have electrodes distributed longitudinally along the axis of the stimulation lead. The electrodes can be distributed longitudinally along the axis of the stimulation lead to enable for flexion between electrode locations. A flexible stimulation lead can be used in spinal cord or pelvic floor stimulation, for example.

Figure 29A:
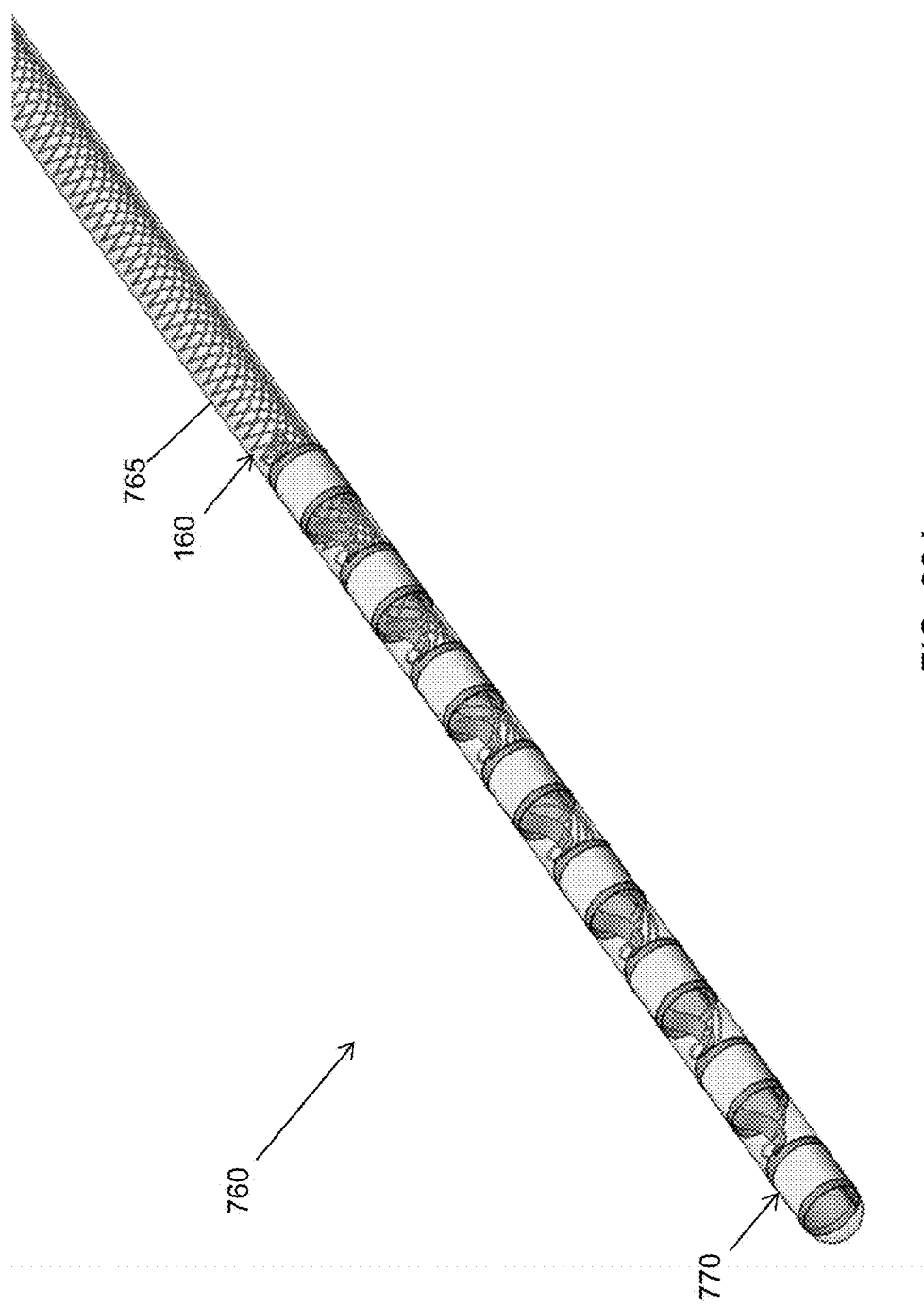

FIG. 29A illustrates the distal end of a stimulation lead 760 configured with electrodes distributed longitudinally along the axis of the stimulation lead 760. The stimulation lead 760 includes a MEMS film 770, which can enable flexion between electrode sites. The MEMS film 770 is connected to the lead wires 160 which are within the external tube 765 to which the MEMS film 770 is disposed.

FIGS. 29B-29D illustrates enlarged views of the distal end of the stimulation lead 760. The MEMS film 770 includes a plurality of electrodes 120 that wrap around the circumference of the external tube 765. Each electrode 120 is coupled with a contact pad 145 through traces embedded in a respective ribbon cable 125. A lead wire 160 is connected and bonded to each of the contact pads 145 through welding, bonding, or gluing to electrically coupled each of the electrodes 120 to the proximal end of the MEMS film 770. All subsequent electrode sites 775 on MEMS film 770 are assembled in the same manner. FIG. 29C and FIG. 29D provide additional planar perspectives of the same distal end of the Neurostimulation lead 760.

FIG. 29E illustrates the MEMS film 770 in a planar configuration before being disposed on the external tube 765. The MEMS film 770 includes a plurality of electrodes 120 disposed on tabs 780. The tabs 780 are connected together by the ribbon cable 125, which includes the contact pad 145 for at least one of the electrodes 120. FIG. 29F illustrates another configuration of the MEMS film 770 where more than one electrode 120 is disposed on each of the tabs 780. The number of contact pads 145 is increased on each ribbon cable 125 to match the number of electrodes 120 disposed on each of the tabs 780. In some implementations, between 2 and 12 electrodes can be disposed on each of the tabs 780.

Figures 30A, 30B:
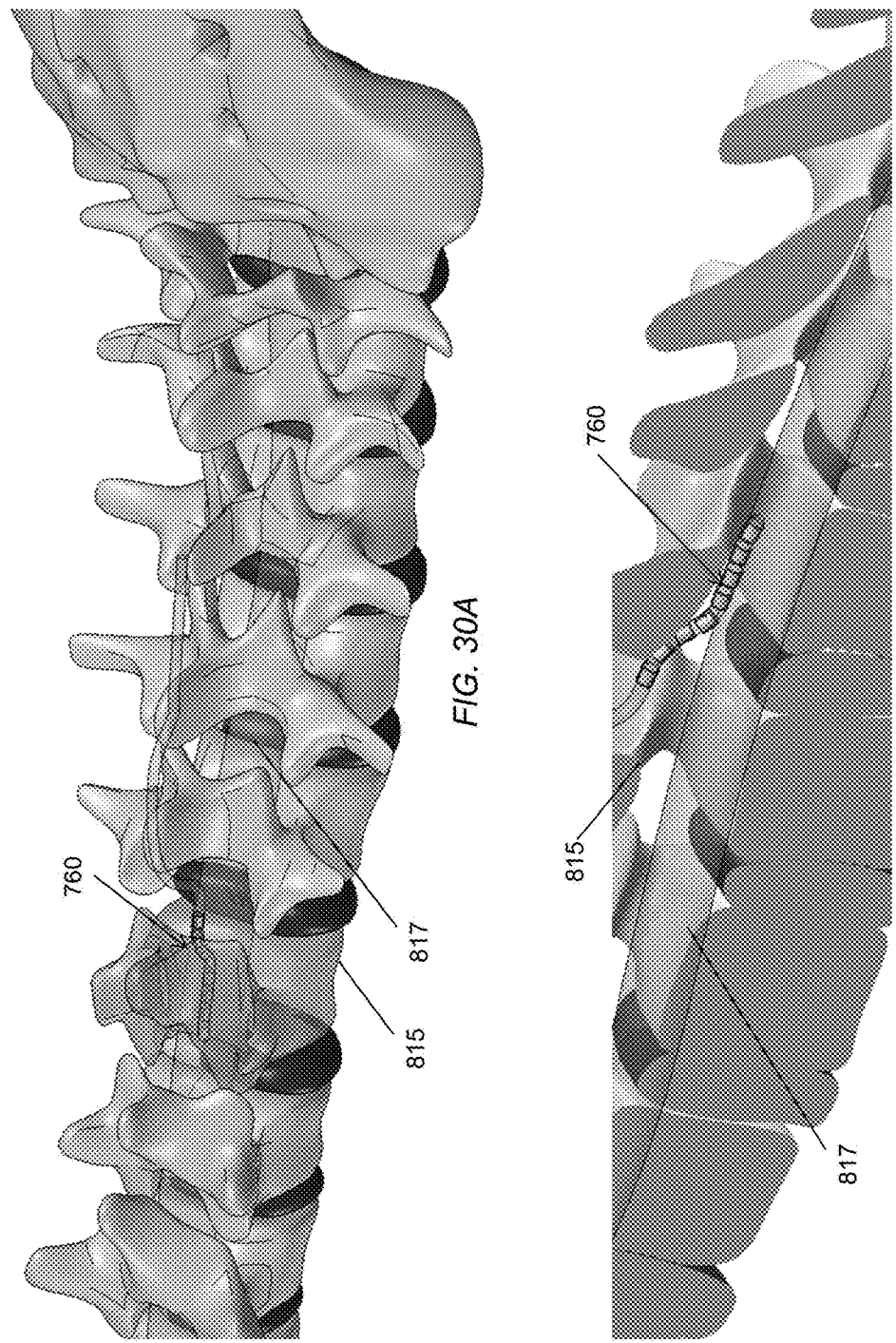
FIGS. 30A and 30B illustrate the stimulation lead implanted near a patient's spinal cord.

FIGS. 30A and 30B illustrate the stimulation lead 760 implanted near a patient's spinal column. The flexible nature of the stimulation lead 760 enables the stimulation lead 760 to be inserted between vertebrae 815 to be positioned near the spinal cord 817.

In some implementations, the platinum electrodes are thickened. The platinum of the electrodes can be electrogalvanically thickened past its native thickness. For example, one method is to insert the distal end of the stimulation lead into an electro-galvanic bath and apply current to the contacts in order to initiate the growth of a platinum layer. FIG. 31 illustrates the process of electrogalvanically thickening electrodes. A stimulation lead 100 is inserted into a bath 842 and a current is applied using a galvanic source 845. In some implementations, one advantage of growing the thickened layer on the molded stimulation lead 100, and not the planar stimulation lead 100 on its carrier wafer, is that the thickened layer may not be stressed when subsequently molded into the cylindrical shape. In these implementations, plasma deposition methods may be used to deposit additional platinum, or other materials such as iridium oxide, to thicknesses greater than the native thickness of the electrode.

FIG. 32A illustrates a cross section of a stimulation lead 100 with no platinum growth, and FIG. 32B illustrates a cross section of a stimulation lead 100 with platinum growth. FIGS. 32A and 32B illustrate that each stimulation lead 100 include a first polyimide layer 870, a first silicon based barrier layer 872, a first metal layer 878, a second silicon based barrier layer 874, and a second polyimide layer 876. As illustrated in FIG. 32B, a galvanically grown platinum layer 880 is deposited on regions where the metal seed layer 878 is exposed. The growth of a platinum layer 880 can be close to the superior surface of the second polyimide layer 876 (e.g., within a few microns), or the platinum layer 880 can provide a platinum thickness that is flush to the surface of the second polyimide layer 876.

In some implementations, the traces, or other metal components of the stimulation lead 100 are disposed in a second metal layer below the metal layer that includes the electrodes 120. Traces in a second metal layer enable the traces to connect to the contact pads and electrode as places other than the edge of the contact pad or electrode. This can enable a more uniform current density for the contact pads and electrodes. Also, each connection to the electrode can make contact with the same electrical potential—improving the uniformness of the current density. FIGS. 33A-33N illustrate the method of manufacturing a MEMS film with a second encapsulated metal layer.

FIG. 33A illustrates the first step of the process where a carrier substrate 901 is provided. A first layer 902 including at least two sub-layers can be applied to a surface of the substrate 901. One of the sub-layers of the first layer 902 can be a sacrificial layer which is later removed in a subsequent electrochemical etch step to separate the finished MEMS film from the carrier substrate 901. The sacrificial sub-layer can be preceded by another sub-layer, referred to as an underlayer, which can serve to form the electrochemical cell to etch the sacrificial layer.

Referring to FIG. 33B, the next step in the fabrication process can include depositing a first polymeric layer 905 upon the sacrificial layer 902. The first polymeric layer can be between about 2 μm and about 15 μm thick.

Referring to FIG. 33C, a silicon based barrier layer 910 can be deposited. The silicon based barrier layer 910 can be between about 500 nm and about 5 μm thick, which can enable the silicon based barrier layer 910 to be flexible enough to bend during subsequent assembly techniques.

FIG. 33D illustrates a first metal layer 915 deposited over the entire wafer on the surface of the silicon based barrier layer 910. The structures within the first metal layer 915, such as traces and contacts, can be structured using photolithographic techniques. The first metal layer 915 can be generally incorporated by depositing several metal layers, such as Titanium, Platinum, and again Titanium, to form a tri-layer which can improve adhesion. The tri-layer can be deposited with thicknesses of 50 nm, 300 nm, and 50 nm respectively.

Referring to FIG. 33E, a second silicon based barrier layer 920 can be deposited. The second silicon based barrier layer 920 can be deposited using the same techniques as the first silicon based barrier layer 910 and can be generally of a similar thickness. In some implementations, the second silicon based barrier layer 920 is slightly thinner than the first silicon based barrier layer 910. As illustrated by FIG. 33E, the second silicon based barrier layer 920 and the first silicon based barrier layer 910 completely surround the metal layer 915 rendering it electrically isolated.

FIG. 33F illustrates that a local etching of the second silicon based barrier layer 920 can be performed to create creates a silicon based barrier layer via (or through hole) 917 that exposes the first metal layer 915.

Referring to FIG. 33G, a second metal layer 925 is deposited on the surface of the second silicon based barrier layer. The second metal layer 925 includes similar metal to the first metal layer 915, and can be about the same or similar thickness to the first metal layer 915. The second metal layer 925 comes into electrical contact with the first metal layer 915 through the silicon based barrier layer via 917.

FIG. 33H illustrates the depositing of a third silicon based barrier layer 927. The third silicon based barrier layer 927 can be deposited in a method similar to the first silicon based barrier layer 910, and can be of the same or similar thickness as the first silicon based barrier layer 910.

FIG. 33H illustrates the etching of the layers. The silicon based barrier layers can be etched using a plasma etch. An example of an etching process includes a reactive ion etching using a tetrafluoromethane gas, (CF4). A photoresist layer can be used to define which areas are etched. Openings in the third silicon based barrier layer 927 can be created in order to expose the second or first metal layers.

FIG. 33I illustrates a second polymer layer 930 deposited on the substrate. The second polymer layer 930 can be the same or a different polymer from the first polymer layer 905, and the second polymer layer 930 can be the same or a different thickness. In some implementations, the second polymer layer 930 is polyimide and is between about 2 μm and about 15 μm thick.

FIG. 33J illustrates the result of an oxygen plasma etching of the first and second polyimide layers 905 and 930, respectively. The etching process creates openings 932 in the second polyimide layer 930 to expose the third silicon based barrier layer 927.

FIG. 33K illustrates the etching of the third silicon based barrier layer 925 to create metal openings 933 to expose the second metal layer 925. In some implementations, the openings 933 can also descend to regions of the first metal layer 915. The openings 933 can define the regions of the electrodes 120 that come into contact with the neural tissue or for define contact pads 145.

FIG. 33L illustrates the deposition of a photoresist layer 935 over the substrate. The photoresist layer 935 can maintain the exposed metal opening 933. The opening 937 in the photoresist layer 935 can create a region for a gold layer to grow.

FIG. 33M illustrates the galvanic growth of a thick gold layer 940 in the opening 937. The gold layer 940 can be grown by connecting all metal traces in the wafer to a perimetric metal band that allows electrical connection between the edge of the wafer and the metal opening 937. In some implementations, the gold growth layer 940 of about 5 μm to about 20 μm thick.

FIG. 33N illustrates that the photoresist layer 935 has been removed to expose the electrode opening 943. The MEMS film is now removed from the wafer 901 by the removal of the sacrificial layer 902 using electrochemically etching.

Figure 34B:
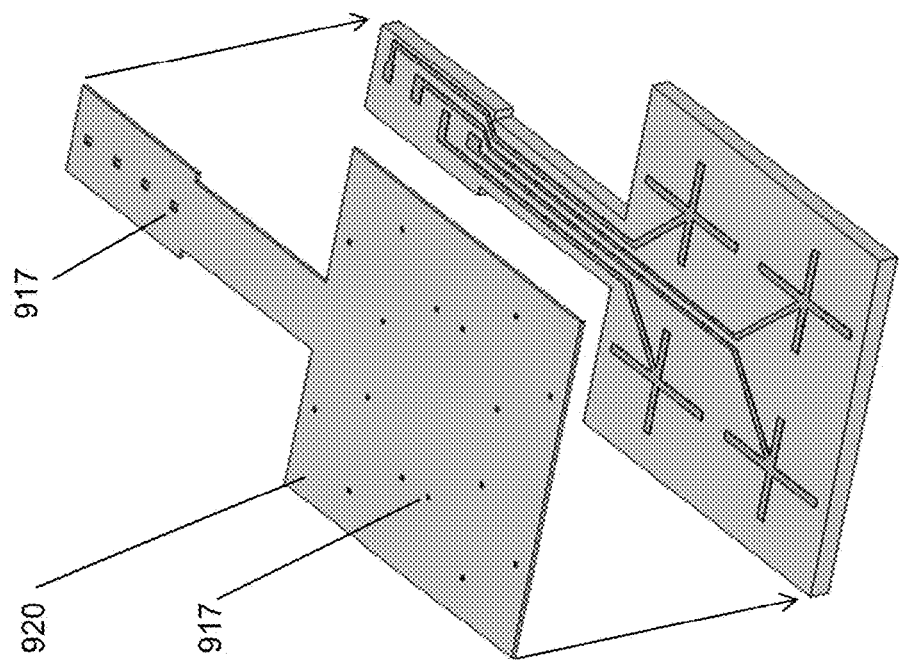
Figure 34A:
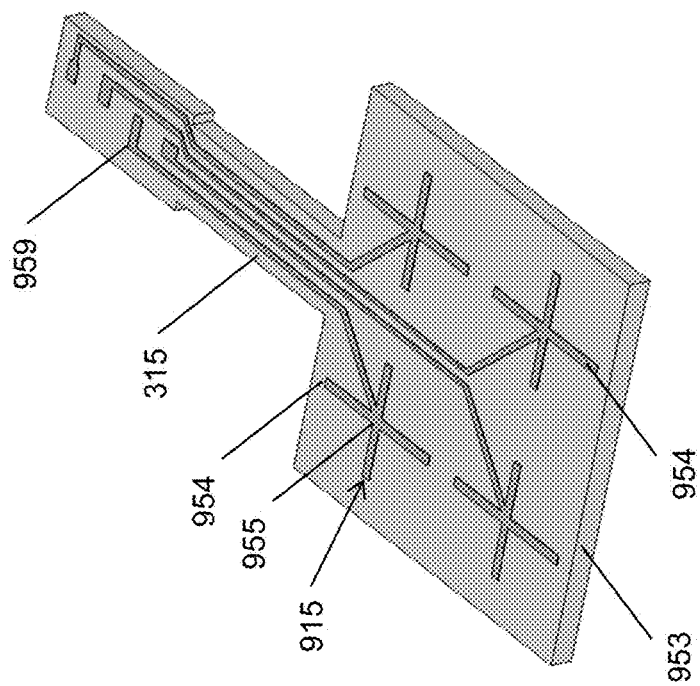

FIGS. 34A-34E illustrate an example of a MEMS film with two metal layers. FIG. 34A illustrates a first metal layer 915 deposited over a first polymeric layer and silicon based barrier layer 953. The placement of the traces in a different metal layer than the electrodes can improve the potential distribution on the surface of electrodes by dispatching traces from a central point of equivalent potential. For example, a potential or current can be applied to the pad 959, the current travels down the trace 315 toward an equipotential cross 955 at a given potential. From the equipotential cross 955, the current travels to each of the four extremities 954 at similar potentials to one another.

FIG. 34B illustrates the application of the second silicon based barrier layer 920. The second silicon based barrier layer 920 includes a number of vias 917 that are configured to align with the ends of the extremities 954 and the pads 959.

FIG. 34C illustrates the application of a second metal layer to the silicon based barrier layer 920. The second metal layer includes the electrodes 120 and the contact pads 145. Each of the electrodes 120 includes a plurality of contact points 977 that make contact with the first metal layer 915 through the vias 917. In other implementations, the electrodes 120 do not include contact points 977, and the electrodes 120 make contact with the first metal layer 915 through vias 917 that are positioned within the body of the electrodes 120.

FIG. 34D illustrates the application of the third silicon based barrier layer and the second polyimide layer 930. The third silicon based barrier layer and the second polyimide layer 930 include through holes 982 that define the electrodes 120 and the contact pads 145.

FIG. 34E illustrates the complete MEMS film. The second polyimide layer 930 defines the electrodes 120 and the contact pads 145. In some implementations, the use of a second metal layer improve the permissible electrode sizes, orientation, and quantity because moving the traces to a separate layer frees surface area within the electrode metal layer, enabling greater freedom to move and arrange electrodes.

Figures 35A, 35B:
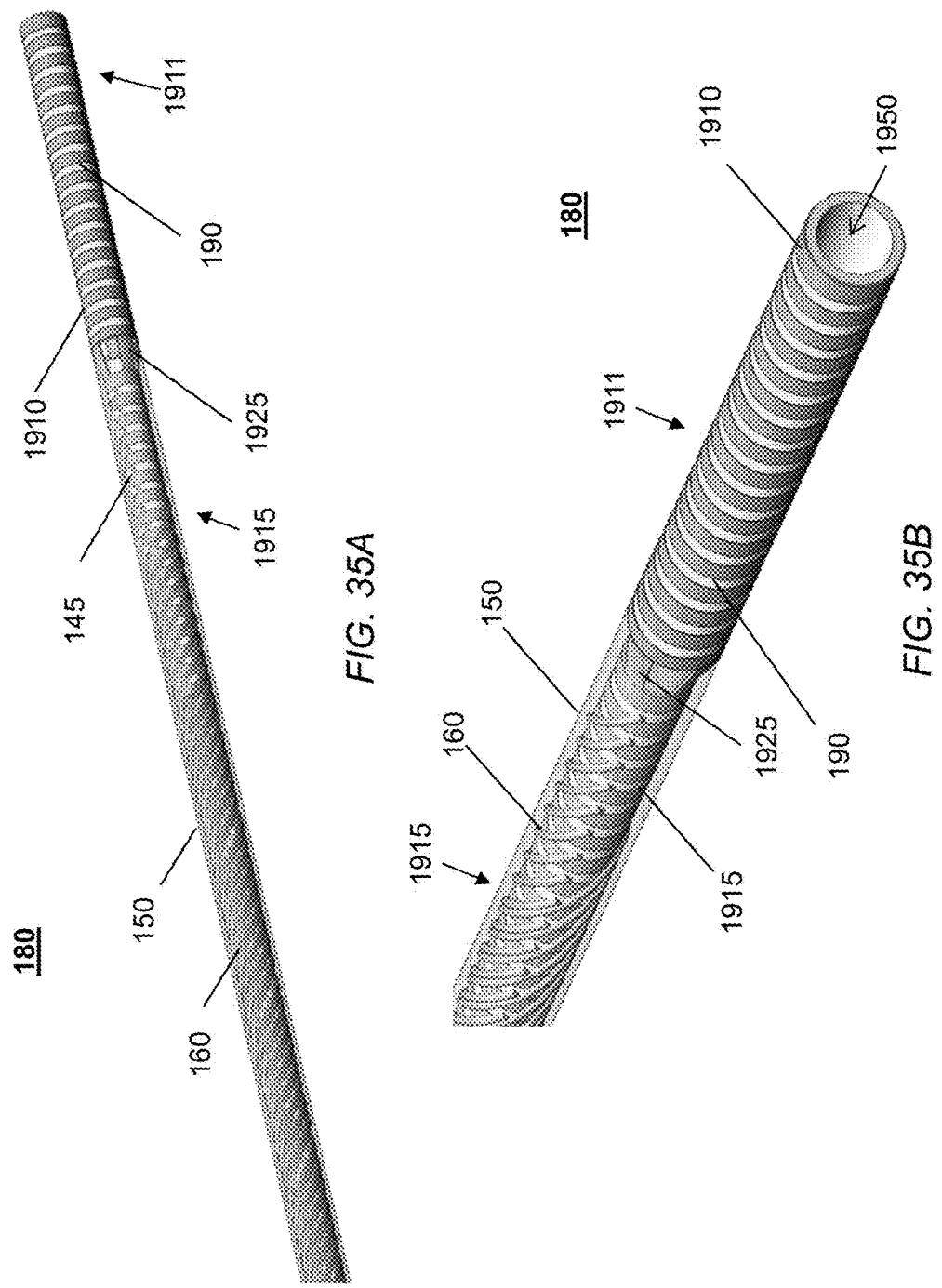
FIGS. 35A and 35B illustrate an example proximal end of the stimulation lead.

FIG. 35A illustrates an example proximal end 180 of the stimulation lead 100. In some implementations, the proximal end contacts 190 can be implemented as a MEMS film. Implementing the proximal end contacts 190 as a MEMS film can decrease the diameter of the proximal end 180 and improve the manufacturability of the proximal end contacts 190. The proximal end 180 can be configured to be compatible with existing extension cables such as the Medtronic 37081 cable. The extension cables can couple the stimulation lead 100 with the implantable stimulator 122, which can be, for example, a Medtronic Activa PC. In some implementations, the proximal end 180 can be configured to be compatible with extension cables that have a smaller pitch between the contacts than compared to the Medtronic 37081. The MEMS film 1910 of the proximal end 180 can be manufactured using the above described MEMS film manufacturing methods. For example, the proximal MEMS film 1910 can be formed as a planar film that is premolded into a cylindrical shape and backfilled with a polymer or epoxy. FIG. 35B illustrates the proximal end 180 from a different angle.

As illustrate in FIGS. 35A and 35B, the MEMS film 1910 includes a distal portion 1915, which incorporates a plurality of contact pads 145 that electrically couple the MEMS film 1910 to the lead wires 160, which run through the lead body 150 toward the distal end of the stimulation lead 100. A proximal portion 1915 of the MEMS film 1910, can include a plurality of proximal contacts 190. The proximal contacts 190 can be in electrical communication with one or more of the contact pads 145 on the distal portion 1915 of the MEMS film 1910. In some implementations, the contact pads 145 are ring electrodes. The proximal portion 1911 and distal portion 1915 of the MEMS film 1910 can be coupled with one another by one or more interconnects 1925. Traces electrically coupling the contacts 190 of the proximal portion 1911 with the contacts 145 of the distal portion 1915 can be housed within the interconnects 1925. In some implementations, redundant traces are included within the at least one of the interconnects 1925. Redundant traces can help guard against a device failure should one interconnect 1925 break. A lumen 1950 is defined through the proximal end 180 of the stimulation lead 100. The lumen 1950 can be configured to permit the passage of an implantation stylet, which can provide stiffness to the stimulation lead 10 during implantation.

In some implementations, the proximal end 180 can include a stiff region distal to the proximal end contacts 190. The stiff region can be between about 1 cm and about 5 cm or between about 1.5 cm and about 2.5 cm long, e.g., substantially 2 cm. The stiff region can help a neurosurgeon push the proximal end 180 into the female end of an extension cable.

In some implementations, the proximal contacts 190 can be thickened using the above described electro-galvanic deposition methods. Thickening the proximal contacts 190 can be advantageous for repeated coupling of an extension cable to the proximal end 180 because the thickened metal layer can improve the proximal contacts' resistances to scratches, making the proximal contacts 190 more reliable and durable. In some implementations, the MEMS film techniques described herein can also be used to implement the extension cable.

Figure 36:
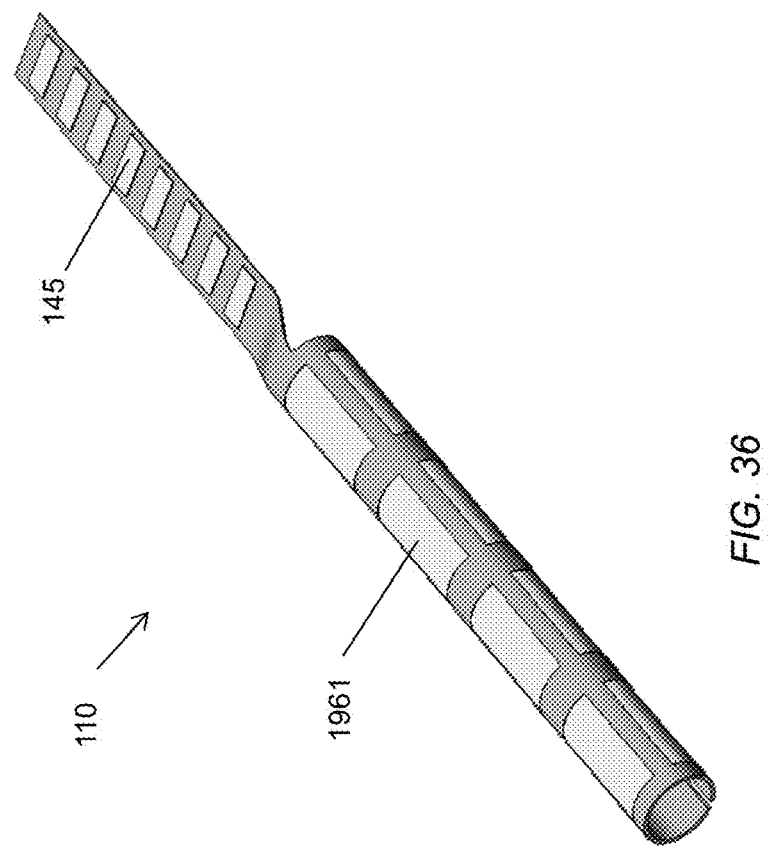
FIG. 36 illustrates an example MEMS film to be disposed within an encapsulating tube.

In some implementations, a MEMS film can be disposed within an encapsulating tube that is coupled with the body 150. FIG. 36 illustrates an example MEMS film 110 disposed within an encapsulating tube. The MEMS film 110 can include a plurality of bond pads 1961 onto which contacts can be coupled. In some implementations, the bond pads 1961 are metal surfaces similar to the electrodes 120. In some implementations, the internal MEMS film 110 can have a smaller diameter when formed into a cylinder than compared to, for example, the cylinder formed from the MEMS film 110 illustrated in FIG. 3A where the MEMS film 110 is not disposed in an encapsulating tube. The diameter of the tube encapsulated MEMS film 100 can be between about 0.5 mm and about 1.5 mm. The internal MEMS film 110 can also include a plurality of contact pads 145.

Figure 37A:
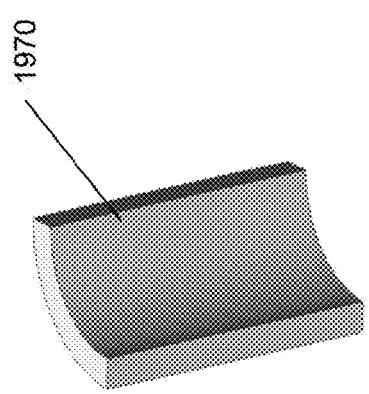
FIGS. 37A and 37B illustrate two views of a platinum contact.
Figure 37B:
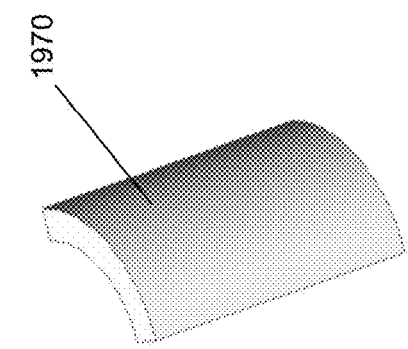

FIGS. 37A and 37B illustrate two views of a contact 1970. In some implementations, the contact 1970 can be relatively thicker when compared to an electrode 120. The contact 1970 can be formed by longitudinally splitting a platinum cylinder with a lumen into a plurality of sections. In some implementations, the platinum cylinder can have an internal diameter between about 0.5 mm and about 1.5 mm and an external diameter between about 0.7 mm and 1.7 mm. In some implementations, a wall of the platinum cylinder is about 0.2 mm thick. The platinum cylinder can be divided into contracts 1970 by laser micromachining the cylinder. In some implementations, the contacts 1970 include platinum, titanium, or other conductive materials with an iridium oxide coating.

FIGS. 38A and 38B illustrate the coupling of the contacts 1970 with the MEMS film 1955. As illustrated, a contact 1970 is coupled with each of the bond pads 1961. In some implementations, the contacts 1970 are coupled with the bond pads 1961 by, for example, laser welding, thermocompression bonding, ultrasonic bonding, conductive gluing, wire bonding, or brazing. FIG. 38B illustrates a contact 1970 coupled to each of the bonding pads 1961. In some implementations, each of the contacts 1970 is much thicker than the MEMS film 110. Once coupled with the MEMS film 110, the contacts 1970 are electrically coupled to the contacts 145 through traces embedded within the MEMS film 110. In some implementations, the contacts 1970 are coupled with the MEMS film 110 after the MEMS film 110 is formed into a cylinder and made rigid by, for example, backfilling the defined lumen with a polymer. In some implementations, the bonding pads 1961 are substantially the same size as the portion of the contacts 1970 that is coupled with the MEMS film 110. In other implementations, the bonding pads 1961 can be larger or smaller than the portion of the contacts 1970 that are coupled with the MEMS film 10. In some implementations, the contact bonding pads 1961 can be cylindrical contacts, or include different sizes and geometries, with some sizes dedicated to simulation, while others are dedicated to recording.

Figure 38D:
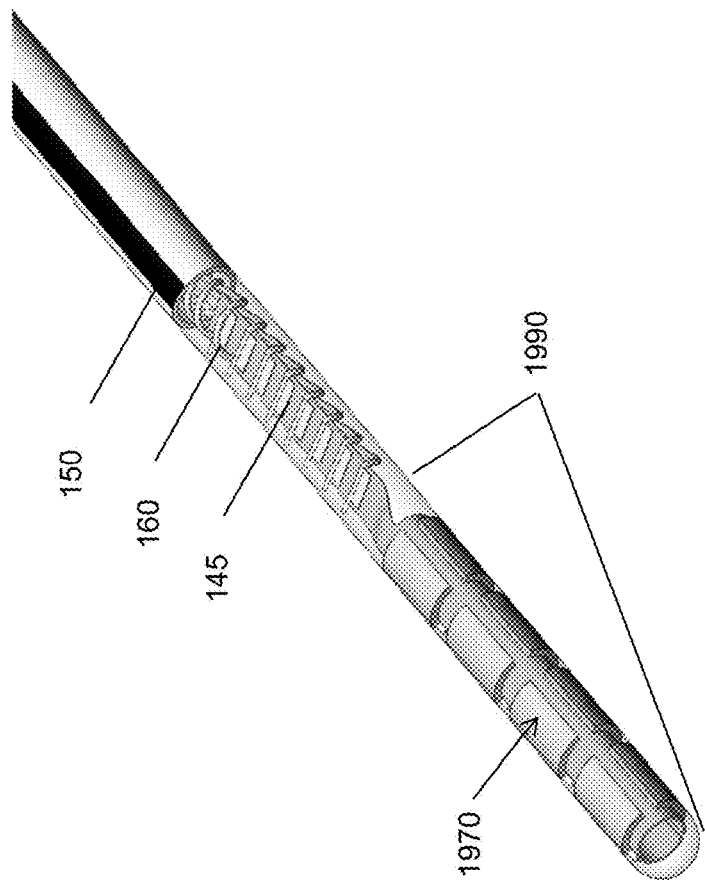
FIG. 38D illustrates an example stimulation lead with a MEMS film disposed within an encapsulating tube.
Figure 38C:
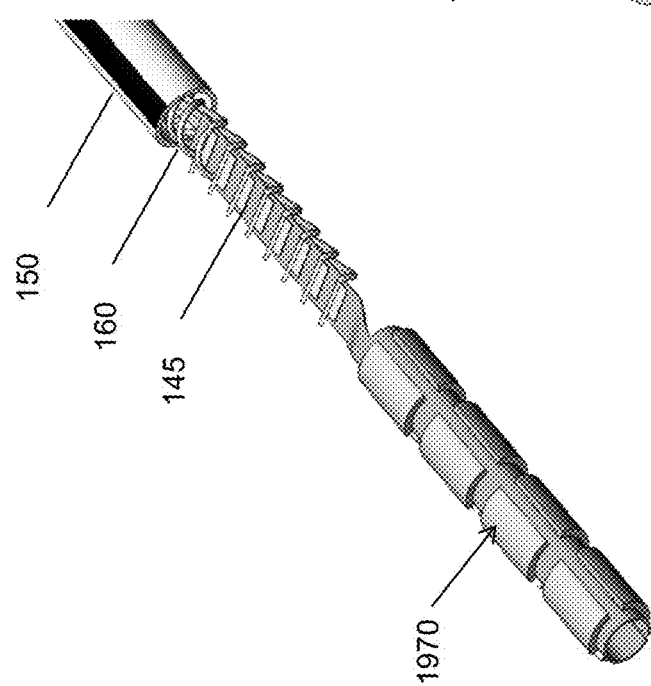
FIG. 38C illustrates the coupling of lead wires to the MEMS film with contacts.

FIG. 38C illustrates the coupling of lead wires 160 to the MEMS film 110 with contacts 1970. The lead wires 160 can be coiled as they run the length of the body 150. A lead wire 160 can be coupled with each of the contact pads 145. FIG. 38D illustrates an example stimulation lead with a MEMS film disposed within an encapsulating tube. The encapsulating tube 1990 encapsulates the MEMS film 110, including the contact pads 145 and the end of the lead wires 160. When encapsulated in the tube 1990, the contacts 1970 are exposed and can be flush with the outer surface of the tube 1990. The tube 1990 can be flush with the body 150. In some implementations, the tube 1990 is formed by overmolding the MEMS film 110 with an epoxy. The overmolding can secure the contracts 1970 to the MEMS film 110 while keeping the surface of the contacts 1970 exposed in order to conduct electrical current to the target site. The overmolding can also electrically isolate the contacts 145 and lead wires 160.

Various implementations of the microelectrode device have been described herein. These embodiments are giving by way of example and not to limit the scope of the present disclosure. The various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the disclosure.

Devices described herein as either acute or chronic may be used acutely or chronically. They may be implanted for such periods, such as during a surgery, and then removed. They may be implanted for extended periods, or indefinitely. Any devices described herein as being chronic may also be used acutely.

The present disclosure is not to be limited in terms of the particular embodiments described in this application, which are intended as illustrations of various aspects. Modifications and variations can be made without departing from its spirit and scope of this disclosure. Functionally equivalent methods and apparatuses may exist within the scope of this disclosure. Such modifications and variations are intended to fall within the scope of the appended claims. The subject matter of the present disclosure includes the full scope of equivalents to which it is entitled. This disclosure is not limited to particular methods, reagents, compounds compositions or biological systems, which can vary. The terminology used herein is for the purpose of describing particular embodiments, and is not intended to be limiting.

With respect to the use of substantially any plural or singular terms herein, the plural can include the singular or the singular can include the plural as is appropriate to the context or application.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Claims directed toward the described subject matter may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, such recitation can mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction would include but not be limited to systems that have A alone, B alone, C alone, A and B together, A and C together, B and C together, and/or A, B, and C together, etc.). Any disjunctive word or phrase presenting two or more alternative terms, whether in the description, claims, or drawings, can contemplate the possibilities of including one of the terms, either of the terms, or both terms. For example, the phrase "A or B" includes the possibilities of "A" or "B" or "A and B."

In addition, where features or aspects of the disclosure are described in terms of Markush groups, the disclosure is also described in terms of any individual member or subgroup of members of the Markush group.

Any ranges disclosed herein also encompass any and all possible subranges and combinations of subranges thereof Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. Language such as "up to," "at least," "greater than," "less than," and the like include the number recited and refer to ranges which can be subsequently broken down into subranges as discussed above. Finally, a range includes each individual member.

One or more or any part thereof of the techniques described herein can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program can be stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis, preprocessing, and other methods described herein can also be implemented as a computer-readable storage medium, configured with a computer program, where the storage medium so configured causes a computer to operate in a specific and predefined manner to perform the functions described herein. In some embodiments, the computer readable media is tangible and substantially non-transitory in nature, e.g., such that the recorded information is recorded in a form other than solely as a propagating signal.

In some embodiments, a program product may include a signal bearing medium. The signal bearing medium may include one or more instructions that, when executed by, for example, a processor, may provide the functionality described above. In some implementations, signal bearing medium may encompass a computer-readable medium, such as, but not limited to, a hard disk drive, a Compact Disc (CD), a Digital Video Disk (DVD), a digital tape, memory, etc. In some implementations, the signal bearing medium may encompass a recordable medium, such as, but not limited to, memory, read/write (R/W) CDs, R/W DVDs, etc. In some implementations, signal bearing medium may encompass a communications medium such as, but not limited to, a digital or an analog communication medium (e.g., a fiber optic cable, a waveguide, a wired communications link, a wireless communication link, etc.). Thus, for example, the program product may be conveyed by an RF signal bearing medium, where the signal bearing medium is conveyed by a wireless communications medium (e.g., a wireless communications medium conforming with the IEEE 802.11 standard).

Any of the signals and signal processing techniques may be digital or analog in nature, or combinations thereof.

While certain embodiments of this disclosure have been particularly shown and described with references to preferred embodiments thereof, various changes in form and details may be made therein without departing from the scope of the disclosure.

What is claimed is:

1. A neurological lead, comprising:
   a first polymeric layer;
   a metal layer disposed on the first polymeric layer, the metal layer comprising:
   a plurality of electrodes;
   a plurality of periphery traces, each of the plurality of periphery traces at least partially encircling a perimeter of a respective one of the plurality of electrodes; and
   at least two connection points coupling each of the plurality of periphery traces to a respective one of the plurality of electrodes; and
   a second polymeric layer disposed on the plurality of periphery traces.

2. The neurological lead of claim 1, comprising:
   a plurality of traces, each of the plurality of traces coupling a respective one of the plurality of periphery traces to a respective one of a plurality of contact pads.

3. The neurological lead of claim 1, comprising:
   a planar formed, cylindrical film comprising a distal end and a proximal end.

4. The neurological lead of claim 3, comprising:
   a ribbon cable extending from the distal end of the planar formed, cylindrical film into a lumen defined by the planar formed, cylindrical film.

5. The neurological lead of claim 1, comprising:
   a second metal layer at least partially disposed over a surface of each of the plurality of electrodes.

6. The neurological lead of claim 5, wherein the second metal layer comprises gold and the metal layer comprises at least one of one of platinum, iridium oxide, and titanium.

7. The neurological lead of claim 1, comprising:
   a first silicon based barrier layer at least partially disposed over the first polymeric layer; and
   a second silicon based barrier layer at least partially disposed over the metal layer and the first silicon based barrier layer, the second silicon based barrier layer defining a first plurality of through-holes.

8. The neurological lead of claim 7, wherein the first and second silicon based barrier layers comprise at least one of Silicon Nitride, Silicon Oxide, Silicon Carbide, Polysilicon, Amorphous-Silicon, Titanium Dioxide, and Titanium III Oxide.

9. The neurological lead of claim 1, wherein the at least two connection points are coupled to opposite edges of the respective one of the plurality of electrodes.

10. The neurological lead of claim 1, comprising:
    a plurality of connection points coupled to an edge of the respective one of the plurality of electrodes.

11. A method, comprising:
    disposing a metal layer on a first polymeric layer;
    forming, in the metal layer, a plurality of electrodes, a plurality of periphery traces, wherein each of the plurality of periphery traces at least partially encircling a perimeter of a respective one of the plurality of electrodes, and at least two connection points coupling each of the plurality of periphery traces to a respective one of the plurality of electrodes; and
    disposing a second polymeric layer on the plurality of periphery traces.

12. The method of claim 11, comprising:
    forming, in the metal layer, a plurality of traces, each of the plurality of traces coupling a respective one of the plurality of periphery traces to a respective one of a plurality of contact pads.

13. The method of claim 11, comprising:
    rolling a film comprising the first polymeric layer, the metal layer, and the second polymeric layer.

14. The method of claim 13, comprising:
    etching a ribbon cable in the film; and
    extending the ribbon cable into a lumen defined by the rolled film.

15. The method of claim 11, comprising:
    disposing a second metal layer at least partially over a surface of each of the plurality of electrodes.

16. The method of claim 15, wherein the second metal layer comprises gold and the metal layer comprises at least one of one of platinum, iridium oxide, and titanium.

17. The method of claim 11, comprising:
    disposing a first silicon based barrier layer at least partially over the first polymeric layer; and
    disposing a second silicon based barrier layer at least partially over the metal layer and the first silicon based barrier layer, the second silicon based barrier layer defining a first plurality of through-holes.

18. The method of claim 17, wherein the first and second silicon based barrier layers comprise at least one of Silicon Nitride, Silicon Oxide, Silicon Carbide, Polysilicon, Amorphous-Silicon, Titanium Dioxide, and Titanium III Oxide.

19. The method of claim 11, wherein the at least two connection points are coupled to opposite edges of the respective one of the plurality of electrodes.

* * * * *